United States Patent
Kim et al.

(10) Patent No.: US 7,682,816 B2
(45) Date of Patent: Mar. 23, 2010

(54) THIN FILM COATED MICROWELL ARRAYS AND METHODS OF USING SAME

(75) Inventors: Jong-Bum Kim, Branford, CT (US); Steven Martin Lefkowitz, Branford, CT (US); John Nobile, Fairfield, CT (US); George Thomas Roth, Fairfield, CT (US); Pengguang Yu, Branford, CT (US)

(73) Assignee: 454 Life Sciences Corporation, Branford, CT (US)

(*) Notice: Subject to any disclaimer, the term of this patent is extended or adjusted under 35 U.S.C. 154(b) by 216 days.

(21) Appl. No.: 11/215,458

(22) Filed: Aug. 30, 2005

(65) Prior Publication Data

US 2006/0228722 A1 Oct. 12, 2006

Related U.S. Application Data

(63) Continuation-in-part of application No. 11/102,075, filed on Apr. 7, 2005.

(51) Int. Cl.
  C12M 1/36 (2006.01)
  G01N 15/06 (2006.01)
  H05H 3/04 (2006.01)

(52) U.S. Cl. .......... 435/283.1; 435/287.2; 422/68.1; 422/82.05; 977/702; 977/707; 977/712; 250/251

(58) Field of Classification Search .......... None
  See application file for complete search history.

(56) References Cited

U.S. PATENT DOCUMENTS

| 5,632,957 | A | 5/1997 | Heller et al. ............ 422/68.1 |
| 5,751,390 | A * | 5/1998 | Crawford et al. ........ 349/120 |
| 6,377,721 | B1 | 4/2002 | Walt et al. ................ 385/12 |
| 6,395,483 | B1 | 5/2002 | Patil et al. ................ 435/6 |
| 6,440,645 | B1 | 8/2002 | Yon-Hin et al. .......... 430/322 |
| 6,448,089 | B1 | 9/2002 | Vuong ..................... 436/164 |
| 7,170,050 | B2 * | 1/2007 | Turner et al. .............. 250/251 |
| 2002/0045272 | A1 * | 4/2002 | McDevitt et al. ......... 436/518 |
| 2003/0068629 | A1 | 4/2003 | Rothberg et al. ......... 435/6 |
| 2003/0091475 | A1 | 5/2003 | Yu et al. ................... 422/99 |
| 2003/0092171 | A1 | 5/2003 | Henck .................... 435/287.2 |
| 2004/0191924 | A1 | 9/2004 | Hunter et al. ............ 436/180 |
| 2004/0240819 | A1 * | 12/2004 | Shima et al. .............. 385/126 |
| 2004/0248161 | A1 | 12/2004 | Rothberg et al. ......... 435/6 |

FOREIGN PATENT DOCUMENTS

| WO | WO 99/28504 | 6/1999 |
| WO | WO 99/30823 | 6/1999 |
| WO | WO 01/18524 A2 | 3/2001 |
| WO | WO 01/20039 A2 | 3/2001 |
| WO | WO 02/077287 A1 | 10/2002 |
| WO | WO 02/078834 A2 | 10/2002 |
| WO | WO 2004/011912 A1 | 2/2004 |

OTHER PUBLICATIONS

Michael et al. "Randomly Ordered Addressable High-Density Optical Sensor Arrays" 1998, 70: 1242-1248.*
Levene et al. "Zero-mode waveguides for single-molecule analysis at high concentrations" Science, Jan. 31, 2003 vol. 200: 682-686 and supplemental materials and methods.*
Guenther et al. *Ron Willey, Opto Mechanik, Inc.*, "Reactive Ion Plating—A Novel Deposition Technique for Improved Optical Coating", pp. 186-191 (1988).
Leamon et al. *Electrophoresis*, 24:3769-3777 (2003).
Schmidt et al. *The Sol-Gel Gateway*, http://www.solgel.com/articles/Nov00/coating.htm, (2000).
Karabacak et al., "Enhanced step coverage by oblique angle physical vapor deposition", *J. Appl. Physics*, 97:124504-1—124504-5 (2005).

* cited by examiner

*Primary Examiner*—BJ Forman
(74) *Attorney, Agent, or Firm*—Ivor R. Elrifi; Jennifer L. Loebach; Mintz, Levin, Cohn, Ferris, Glovsky and Popeo, P.C.

(57) ABSTRACT

This invention relates to microwell array compositions which are coated with one or more thin film coatings. The invention includes the process of fabricating and using thin film coated microwell arrays.

20 Claims, 37 Drawing Sheets

SEMs of Coated FOFs

Cross-Section SEMs of Coated FOFs

Schematic Diagram
Of Ion-Plating Process

PCR-Induced Sequencing Background of SiO$_2$-Coated and Uncoated FOFs (error bars = 95% CL for 3 samples)

Sequencing Performance Metrics of SiO$_2$-Coated and Uncoated FOFs

Rotary and Angled Jig Assembly

A

B

THIN FILM COATED MICROWELL ARRAYS AND METHODS OF USING SAME

RELATED APPLICATIONS

This application is a continuation in part of U.S. Ser. No. 11/102,075 filed on Apr. 7, 2005, the entire contents of which is hereby incorporated by reference.

FIELD OF THE INVENTION

This invention relates to microwell array compositions comprised of a substrate coated with one or more thin film coatings. The invention includes the process of fabricating and using the thin film coated microwell array.

BACKGROUND OF THE INVENTION

The ability to perform parallel microanalysis on minute quantities of sample is important to the advancement of chemistry, biology, drug discovery and medicine. Today, the traditional 1536-well microtitre plate has been surpassed by microwell arrays which have an even greater number of reaction chambers and use lesser amounts of reagents due to efforts focused on maximizing time and cost efficiencies. Although there are several types of microwell arrays available, many microwell materials prove to be incompatible with the components of bioassays and chemical reactions and result in problems such as low sensitivity, high background signal, and lack of reproducibility. Thus, there continues to be a need for the development of improved microwell arrays.

One solution to the problem of incompatible materials is to apply a thin film coating of a compatible material to the microwell array to enhance its surface properties and function. Patil, et al. U.S. Pat. No. 6,395,483 has disclosed a method to coat polymeric substrates with mask layers comprised of metallic and metal-oxide for use in high-density microarray applications. Yon-Hin, et al. U.S. Pat. No. 6,440,645 has described a process to use a photoimageable thin film on a polymer substrate to form microwells or channels. Heller, et al. U.S. Pat. No. 5,632,957 describes the deposition of metal, insulator and passivation coatings of substrates to form microelectrode arrays, and to form microwells over the individual microelectrodes. Walt, et al. U.S. Pat. No. 6,377,721 has disclosed coating the interior surfaces of the microwells on fiber optic arrays with a thin film or a layer of biologically compatible material.

Certain fiber optic bundles have been used to create arrays. Several methods are known in the art for attaching functional groups (and detecting the attached functional groups) to reaction chambers etched in the ends of fiber optic bundles. See, e.g., Michael, et al., *Anal. Chem.* 70: 1242-1248 (1998); Ferguson, et al., *Nature Biotechnology* 14: 1681-1684 (1996); Healey and Walt, *Anal. Chem.* 69: 2213-2216 (1997). A pattern of reactive functional groups can also be created in the reaction chamber, using photolithographic techniques similar to those used in the generation of a pattern of reaction pads on a planar support. See, Healey, et al., Science 269: 1078-1080 (1995); Munkholm and Walt, *Anal. Chem.* 58: 1427-1430 (1986), and Bronk, et al., *Anal. Chem.* 67: 2750-2757 (1995).

An array of functional groups on a substrate can be constructed using lithographic techniques commonly used in the construction of electronic integrated circuits as described in, e.g., techniques for attachment described in U.S. Pat. Nos. 5,143,854, 5,445,934, 5,744,305, and 5,800,992; Chee et al., Science 274: 610-614 (1996); Fodor et al., Nature 364: 555-556 (1993); Fodor et al., Science 251: 767-773 (1991); Gushin, et al., *Anal. Biochem.* 250: 203-211 (1997); Kinosita et al., *Cell* 93: 21-24 (1998); Kato-Yamada et al., *J. Biol. Chem.* 273: 19375-19377 (1998); and Yasuda et al., *Cell* 93: 1117-1124 (1998). Photolithography and electron beam lithography sensitize the substrate with a functional group that allows attachment of a reactant (e.g., proteins or nucleic acids). See e.g., Service, Science 283: 27-28 (1999); Rai-Choudhury, HANDBOOK OF MICROLITHOGRAPHY, MICROMACHINING, AND MICROFABRICATION, VOLUME I: MICROLITHOGRAPHY, Volume PM39, SPIE Press (1997). Alternatively, an array of functional groups can be generated using thin film technology as described in Zasadzinski et al., *Science* 263: 1726-1733 (1994).

One major disadvantage of this type of fiber optic array is the constraint of the materials comprising the fiber optic bundle. To act as an efficient waveguide, each fiber element should include a high refractive index core surrounded by a low refractive index cladding. These fiber optic materials are often incompatible with many reaction conditions, particularly bioassays which are often conducted in aqueous solutions and contain sensitive enzymatic reagents. Two major sources of incompatibility are the dissolution of the fiber optic substrate into the solution contained in the reaction chamber and the actual chemical reaction of the fiber optic substrate with components contained in the chamber. For example, core components, such as barium and lanthanum oxides, can form hydroxides which are water soluble, particularly at elevated temperatures. Multivalent heavy metals, such as barium and lanthanum, can interact unfavorably with enzymes, especially those enzymes with metal ion co-factors. Heavy metal oxide surfaces tend to be positively charged at the solution interface and tend to non-specifically bind negatively charged species such as nucleic acids. All of these effects will tend to degrade the performance of assays and reactions conducted in the fiber optic reaction chambers. Increasing miniaturization also tends to exacerbate these unfavorable effects.

The fact that the fiber optic substrate is comprised of two materials (core and cladding) also can limit the effectiveness of any surface modification of the reaction chambers with a monolayer (e.g. functional groups). For example, a singly charged surface is modified by binding to the charged surface of functionalized polyelectrolytes which contain an opposite charge. The core and cladding materials of the fiber optic substrate each have different types of charges. Thus, any modification of the fiber optic substrate with a single polyelectrolyte is impossible since the substrate does not contain a single uniform charge.

The optical properties of a fiber optic substrate are also limited. During a photochemical reaction carried out in the reaction chamber of a fiber optic faceplate, photons are generated which run through the fiber core and eventually reach through the other end of the fiber. At the same time, photons can also penetrate through the cladding material and travel until they are trapped by another fiber of an adjoining reaction chamber. These photons which travel through the transparent cladding are often referred to as optical scattering and result in problems such as optical bleeding and physical interferences (e.g., cross-talk) between neighboring reaction chambers.

There is a clear need for microwell arrays which are compatible for any bioassay or reaction condition and which have superior optical properties.

SUMMARY OF THE INVENTION

One way to alleviate the problems associated with using fiber optic faceplates for chemical reactions and bioassays is to coat the array substrate with one or more thin film coatings using methods described herein. In general, the discussion herein is focused on fiber optic substrates, although other substrates as described below may be used in any embodiment described herein.

This invention relates to array compositions which include a substrate coated with one or more thin film coatings wherein at least one of the coatings is non-transparent. One aspect of the invention is an array which includes a substrate that is a fiber optic faceplate having a top surface with a plurality of reaction chambers and a bottom surface. Each reaction chamber of the array has a bottom and a sidewall. At least one of the bottom or sidewall of substantially all of the reaction chambers or the top surface of the array is coated with a non-transparent thin film coating, wherein the non-transparent coating is opaque, semi-opaque, shiny opaque, or translucent and at least one of the bottom or sidewall of substantially all of the reaction chambers or the top surface of the array is coated with a transparent thin film coating. The transparent coating differs from the non-transparent coating, and the non-transparent coating is optically transparent, 0.1-5.0 microns thick, and is impermeable to water.

In one embodiment, the transparent coating is silicon dioxide. In a further embodiment, when present, the thickness of the transparent coating is about 200-400 nm on the top surface of the array, 50-100 nm on the sidewall, and 100-300 nm on the bottom.

In another embodiment, the non-transparent coating is opaque. In another embodiment, the non-transparent coating is semi-opaque. In another embodiment, the non-transparent coating is shiny opaque. In another embodiment, the non-transparent coating is translucent. In one embodiment, when present, the thickness of the non-transparent coating is about 200-300 nm on the top surface of the array, 60-120 nm on the sidewall, and no less than 50 nm on the corner area, wherein the corner area is the comprised of the junction formed between the bottom and sidewall of the reaction chamber.

The non-transparent coating is selected from an organic compound, an inorganic compound, and a non-metal oxide. In one embodiment, the inorganic compound is a metal. In another embodiment, the non-transparent coating is selected from chromium, gold, silver, titanium, platinum and aluminum. In one embodiment, the non-transparent coating is conductive. In another embodiment, the non-transparent coating is dielectric.

In another embodiment, the sidewall of substantially all of the reaction chambers is coated with the transparent coating. In another embodiment, the top surface of the array is coated with the transparent coating. In another embodiment, the bottom of substantially all of the reaction chambers is coated with the transparent coating. In one embodiment, each one of the sidewall and bottom of substantially all of the reaction chambers and the top surface of the array is coated with the transparent coating.

In one embodiment, the bottom and sidewall of substantially all of the reaction chambers are partially coated with a transparent coating, such that the transparent coating is applied to the corner area formed at the junction between the bottom and sidewall of the reaction chamber, and the coating is absent from the center of the bottom of the reaction chamber and forms an aperture near the center of the bottom. In one embodiment, the diameter of the aperture is about 28 microns. In another embodiment, a ring of coating is formed around the aperture on the bottom of the reaction chamber when the coating is applied to the corner area and the ring of coating has a width of 8.5 microns.

In another embodiment, the sidewall of substantially all of the reaction chambers is coated with the non-transparent coating. In another embodiment, the top surface of the array is coated with the non-transparent coating. In another embodiment, the bottom of substantially all of the reaction chambers is coated with the non-transparent coating. In one embodiment, the bottom and sidewall of substantially all of the reaction chambers are partially coated with a non-transparent coating, such that the non-transparent coating is applied to the corner area formed at the junction between the bottom and sidewall of the reaction chamber, and the non-transparent is absent from the center of the bottom of the reaction chamber and forms an aperture near the center of the bottom. In a further embodiment, the transparent coating is applied to the array that is already partially coated with a non-transparent coating and the transparent coating is applied to at least one of the bottom or sidewall of substantially all of the reaction chambers or top surface of the array.

In one embodiment, the sidewall of substantially all of the reaction chambers and the top surface of the array are coated with the transparent coating, and the bottom is coated with the non-transparent coating. In one embodiment, the sidewall and bottom of substantially all of the reaction chambers are coated with the transparent coating, and the top surface of the array is coated with the non-transparent coating. In another embodiment, the top surface of the array and bottom of substantially all of the reaction chambers are coated with the transparent coating, and the sidewall of substantially all of the reaction chambers is coated with the non-transparent coating. In another embodiment, the bottom of substantially all of the reaction chambers is coated with the transparent coating, and the sidewall of substantially all of the reaction chambers and the top surface of the array are coated with the non-transparent coating. In another embodiment, the top surface of the array is coated with the transparent coating, and the sidewall and bottom of substantially all of the reaction chambers are coated with the non-transparent coating. In another embodiment, the sidewall of substantially all of the reaction chambers is coated with the transparent coating, and the bottom of substantially all of the reaction chambers and the top surface of the array are coated with the non-transparent coating. In another embodiment, the bottom of substantially all of the reaction chambers is coated with the transparent coating, the sidewall of substantially all of the reaction chambers is coated with the non-transparent coating, and the top surface of the array is not coated. In another embodiment, the transparent coating includes at least a first transparent coating. In another embodiment, the non-transparent coating includes at least a first non-transparent coating.

In another embodiment, the non-transparent coating is applied to the array before any transparent coating is applied. In one embodiment, at least one bottom or sidewall of substantially all of the reaction chambers or top surface of the array is coated with the non-transparent coating before any transparent coating is applied. In another embodiment, the transparent coating is applied to the array before any non-transparent coating is applied. In another embodiment, at least one bottom or sidewall of substantially all of the reaction chambers or top surface of the array is coated with the transparent coating before any non-transparent coating is applied.

In one embodiment, an enzyme is immobilized on the non-transparent coating. In another embodiment, an enzyme is immobilized on the transparent coating. In one embodiment, the reaction chambers of the array are arranged in a regular pattern. In another embodiment, the reaction chambers of the array are arranged in an irregular pattern. In another embodiment, the spacing between the center points of two adjoining reaction chambers on the array is between 5 μm to 200 μm, and each reaction chamber has a width in at least one dimension of between 4 μm and 190 μm. In one embodiment, the number of reaction chambers is 10,000 or less. In another embodiment, the number of reaction chambers is greater than 10,000. In one embodiment, the depth of substantially all of the reaction chambers is between 10-100 μm. In another embodiment, the depth of substantially all of the reaction chambers is between 50-55 μm.

In another embodiment, the array is comprised of a top surface comprising a plurality of reaction chambers and an opposed, planar, polished bottom surface without reaction chambers, wherein the polished bottom surface is optically transmissive such that optical signals from the reaction chambers are detected through the polished surface, wherein the distance between the top surface comprising the reaction chambers and the polished bottom surface is no greater than 5 mm in thickness.

In one embodiment, the array comprises an index feature. In another embodiment, the array substrate comprises one or more side edges beveled at an angle. In another embodiment, the angle is 45 degrees. In another embodiment, the substrate is marked with one or more identifier codes.

Another aspect of the invention is an array which includes a substrate that is a fiber optic faceplate having a top surface which includes a plurality of reaction chambers and a bottom surface. Each reaction chamber of the array has a bottom and sidewall. At least one of the bottom or sidewall of substantially all of the reaction chambers or top surface of the array is coated with a non-transparent, thin film coating. The non-transparent coating is opaque, semi-opaque, shiny opaque, or translucent.

In one embodiment, at least one of the bottom or sidewall of substantially all of the reaction chambers or top surface of the array is not coated. In one embodiment, the non-transparent coating is opaque. In another embodiment, the non-transparent coating is semi-opaque. In another embodiment, the non-transparent coating is shiny opaque. In another embodiment, the non-transparent coating is translucent.

In one embodiment, when present, the thickness of the non-transparent coating is about 200-300 nm on the top surface of the array, 60-120 nm on the sidewall, and no less than 50 nm on the corner area, wherein the corner area is the comprised of the junction between the bottom and sidewall of the reaction chamber. In another embodiment, the non-transparent coating is selected from an organic compound, an inorganic compound, and a non-metal oxide. In one embodiment, the inorganic compound is a metal. In another embodiment, the non-transparent coating is selected from chromium, gold, silver, titanium, platinum, and aluminum. In one embodiment, the non-transparent coating is conductive. In another embodiment, the non-transparent coating is dielectric.

In another embodiment, the sidewall of substantially all of the reaction chambers is coated. In another embodiment, the top surface of the array is coated. In another embodiment, the bottom of substantially all of the reaction chambers is coated. In another embodiment, the bottom and sidewall of substantially all of the reaction chambers are partially coated with a non-transparent coating, such that the non-transparent coating is applied to the corner area formed at the junction between the bottom and sidewall of the reaction chamber, and the non-transparent coating is absent from the center of the bottom of the reaction chamber and forms an aperture near the center of the bottom. In another embodiment, the diameter of the aperture is 28 microns. In another embodiment, a ring of coating is formed around the aperture when the coating is applied to the corner area and the ring of coating has a width of 8.5 microns.

In one embodiment, the sidewall of substantially all of the reaction chambers and the top surface of the array are coated. In another embodiment, the sidewall and bottom of substantially all of the reaction chambers are coated. In another embodiment, the bottom of substantially all of the reaction chambers and the top surface of the array are coated.

In one embodiment, the non-transparent coating comprises at least a first non-transparent coating. In another embodiment, the non-transparent coating comprises at least a first non-transparent coating and a second non-transparent coating, further wherein the first and second non-transparent coatings are not the same. In another embodiment, an enzyme is immobilized on the non-transparent coating. In one embodiment, the reaction chambers of the array are arranged in a regular pattern. In another embodiment, the reaction chambers of the array are arranged in an irregular pattern. In another embodiment, the spacing between the center points of two adjoining reaction chambers of the array is between 5 μm to 200 μm, and each reaction chamber has a width in at least one dimension of between 4 μm and 190 μm.

In one embodiment, the number of reaction chambers of the array is 10,000 or less. In another embodiment, the number of reaction chambers of the array is greater than 10,000. In one embodiment, the depth of substantially all of the reaction chambers of the array is between 10-100 μm. In another embodiment, the depth of substantially all of the reaction chambers of the array is between 50-55 μm. In another embodiment, the array includes a top surface which contains a plurality of reaction chambers and an opposed, planar, polished bottom surface without reaction chambers, wherein the polished bottom surface is optically transmissive such that optical signals from the reaction chambers are detected through the polished bottom surface, wherein the distance between the top surface comprising the reaction chambers and the polished bottom surface is no greater than 5 mm in thickness.

In one embodiment, the array includes an index feature. In another embodiment, the array substrate includes one or more side edges beveled at an angle. In another embodiment, the angle of the beveled side edge is 45 degrees.

Another aspect of the invention is a process for depositing a non-transparent thin film coating on a top surface of a substrate containing a plurality of reaction chambers, where each reaction chamber has a bottom and sidewall. The non-transparent coating is opaque, semi-opaque, shiny opaque, or translucent and is deposited on at least one bottom or sidewall of substantially all of the reaction chambers or top surface of the array. The steps of the process include: (a) mounting a substrate onto a substrate carrier at an angle, (b) spinning the mounted substrate in a vacuum chamber, (c) depositing the non-transparent coating onto at least one bottom or sidewall of substantially all of the reaction chambers or top surface of the array, (d) removing the substrate from the vacuum chamber, and (e) dismounting the substrate coated with the non-transparent coating from the substrate carrier. In one embodiment, the substrate is a fiber optic faceplate. In another embodiment, at least one bottom or sidewall of substantially all of the reaction chambers or top surface of the array is coated with a transparent coating before the non-transparent coating is applied. In another embodiment, at least one bottom or sidewall of substantially all of the reaction chambers or top surface of the substrate is coated with a non-transparent coating prior to the application of a transparent coating to at least one bottom or sidewall of substantially all of the reaction chambers or top surface of the substrate. In another embodiment, the transparent coating is optically transparent, 0.1-5.0 microns thick, and impermeable to water.

BRIEF DESCRIPTION OF THE FIGURES

FIG. 2a is a schematic of a deposition area in a reaction chamber. FIG. 2b is an image of coating applied by sputtering. FIG. 2c is an image of a coating applied by PECVD. FIG. 2d is an image of a coating applied by ion-platting;

DETAILED DESCRIPTION OF THE INVENTION

Figure 1:
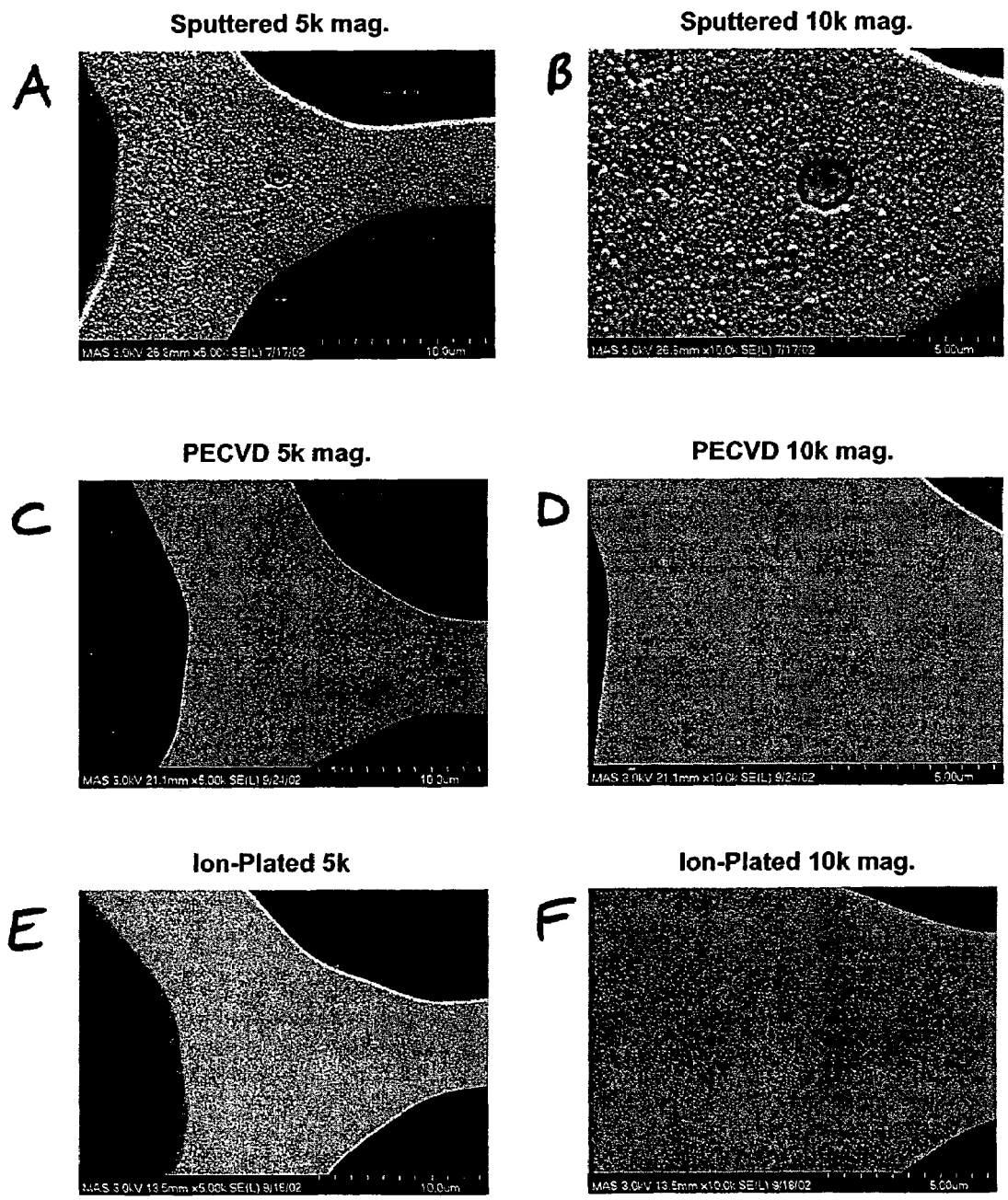
FIG. 1 is a series of SEM images at 5 k and 10 k magnification of etched fiber optic faceplates coated with $SiO_2$ using the sputtering (FIGS. 1a and 1b), PECVD (FIGS. 1c and 1d), and ion-plating (FIGS. 1e and 1f) vapor deposition methods.

Definitions:

Unless otherwise defined, all technical and scientific terms used herein have the same meaning as commonly understood by one of ordinary skill in the art to which this invention belongs. Methods and materials similar or equivalent to those described herein can be used in the practice of the present invention, and exemplified suitable methods and materials are described below. For example, methods may be described which comprise more than two steps. In such methods, not all steps may be required to achieve a defined goal and the invention envisions the use of isolated steps to achieve these discrete goals. The disclosures of all publications, patent applications, patents and other references are incorporated in toto herein by reference. In addition, the materials, methods, and examples are illustrative only and not intended to be limiting.

"Analyte" means a molecule, compound, composition or complex, either naturally occurring or synthesized, to be detected or measured in or separated from a sample of interest. Analytes include, without limitation, proteins, peptides, amino acids, fatty acids, nucleic acids, carbohydrates, hormones, steroids, compounds, lipids, vitamins, bacteria, viruses, pharmaceuticals, and metabolites.

"Clamped Sandwich" refers to a combination of two FOFs with a gasket positioned in between the two FOFs, wherein the corner notch of each FOF is properly aligned with the appropriate gasket corner barrier, such that the polished surface of each FOF is facing towards the gasket, wherein a seal is formed between the polished surface of the FOF and the gasket which is impermeable to liquid.

"Core material" refers to the inner component of a fiber optic fiber. The material is transparent and has a high refractive index.

"Cladding material" refers to the outer component of a fiber optic fiber. The material is transparent and has a low refractive index.

"Corner Area" refers to the inner surface of the reaction chamber where a junction is formed between the sidewall and bottom of the reaction chamber. (see FIG. 16a).

"Corner barrier" refers to a feature on a gasket, which includes a band that is placed at an angle in the corner of a gasket and provides a physical basis for orienting an FOF when the FOF is mounted in the gasket.

"Corner notch" refers to one corner of a fiber optic faceplate which is cut at angle and removed to provide a physical basis for orienting the fiber optic faceplate, for example when a fiber optic faceplate is mounted on a system for analysis or in a gasket for the etch process, the corner notch of the fiber optic faceplate is matched with a complementary feature located on the analysis system or gasket.

"Etch process" refers to a chemical process using acid to create reaction chambers in an array substrate.

"Fiber optic faceplate" or "FOF" refers to a bundle of fiber optic cables which are fused together to form a monolithic structure which is then "sliced" to form a "wafer" of required thickness.

"Functional groups" means any chemical or biological species capable of affixing a reactant, reaction substrate, or analyte to the inside surface of the reaction chamber.

"Gasket" refers to one component of the apparatus for the etch process. The gasket is aligned between two FOFs and protects one side of each FOF (e.g., the polished side) from exposure to acid by forming a fluid tight seal.

"Gasket Index Feature" refers to a band positioned in one corner of a gasket which creates a notch that is complementary to the corner notch of a FOF and that provides a physical basis for orienting a FOF.

"Index Feature" refers to a structure that provides a physical basis for orienting a FOF.

"FOF Index Feature" refers to a corner notch on the FOF which provides a physical basis for properly orienting a FOF.

"Ion-Plating" means a method of vapor deposition used for depositing a thin film coating on an array substrate where first, electrically charged and neutral atoms are used to remove contaminants from the substrate and second, the coating material is evaporated, enhanced by the interaction with energetic inert gas or reactive gas atoms and ions, and deposited on the substrate.

"Impermeable to Water" refers to the ability of a thin film coating to provide a barrier to an aqueous solution contained in the reaction chamber and to prevent leaching of the chamber solution into the sidewall components of the reaction chamber.

"Non-transparent Thin Film Coating" or "Non-transparent Coating" refers to a coating of material that modulates e.g., blocks, substantially blocks, or diffuses the passage of light through there through. For example, the non-transparent thin film coating or non-transparent coating is opaque, semi-opaque, shiny opaque, or translucent.

"Opaque" means that the passage of light is blocked such that less than 2 out of 1000 photons pass through a thin film material.

"Optically Transparent" refers to the ability of light to transmit through a thin film coating. "PEEK clamp" refers to a clamp made of poly ether ether ketone which is used to firmly hold two FOFs and a gasket together during the etch process.

"Partial Coating" means less than the entire surface is coated e.g., less than the entire surface of a bottom or sidewall of a reaction chamber is coated. "PicoTiter Plate™" or "PTP" means an array substrate which includes an etched FOF.

"Plasma-Enhanced Chemical Vapor Deposition" or "PECVD" means a method of vapor deposition used for depositing a thin film coating on an array substrate, where the thin film coating is produced from the chemical reaction of gases.

"Reactant" means any chemical or biological molecule, compound, composition or complex, either naturally occurring or synthesized, that is capable of binding, forming, or reacting with an analyte in a sample of interest either alone or in conjunction with another reactant. The reactants of the present invention are useful for chemical reaction or biochemical measurement, detection or separation. Examples of reactants include, without limitation, amino acids, nucleic acids, including oligonucleotides and cDNA, carbohydrates, and proteins such as enzymes and antibodies.

"Reaction Chamber" means a localized well or chamber comprised of a bottom and a sidewall (i.e. a hollowed-out space, having width and depth) that is found on a substrate.

"RCA cleaner" means a solution of ammonium hydroxide and hydrogen peroxide.

"RER cleaning process" refers to a process for cleaning an etched FOF using RCA cleaner, EDTA, and RCA cleaner.

"Sandwich" refers to a combination of two FOFs with a gasket positioned in between the two FOFs, wherein the corner notch of each FOF is properly aligned with the appropriate gasket index feature, such that the polished surface of each FOF is facing towards the gasket and the unpolished surface is exposed.

"Scanning Electron Microscopy" or "SEM" refers to a method for high resolution imaging.

"Semi-opaque" means that the passage of light is nearly blocked such that less than 10% of the light is passed through the thin film coating.

"Shiny Opaque" means the passage of light is blocked such that less than 2 out of 1000 photons pass through a thin film coating and the light is reflected off of the shiny opaque surface.

"Sputtering" means a method of vapor deposition used for depositing a thin film coating on an array substrate.

"Substrate" refers to a solid support or any material that can be modified to contain discrete individual reaction chambers and is amenable to at least one detection method.

"Thin Film" of "Thin Film Coating" refers to a coating of material deposited on the surface of the substrate.

"Transparent" means that light is permitted to pass through a thin film coating without appreciable scattering such that objects can be seen clearly.

"Transparent Thin Film Coating" or "Transparent Coating" refers to a coating of material deposited on the surface of the substrate wherein the coating is less than 5.0 microns thick, optically transparent, and impermeable to water.

"Translucent" means that light is permitted to pass through a thin film coating, but the light is diffuse such that objects can not be seen clearly.

"Vapor deposition" refers to a method for depositing a thin film coating on the array.

The present invention provides array compositions including a substrate which has individual reaction chambers and is coated with one or more thin film coatings. The invention includes the process of fabricating and using the coated array. By "array" herein is meant a plurality of reaction chambers, which are localized wells or chambers in an array format on the surface of a substrate. Each reaction chamber includes a bottom and sidewall. The size of the array and its reaction chambers will depend on the composition and end use of the array. In one embodiment, the array, including at least one bottom or sidewall of substantially all of the reaction chambers of the array or top surface of the array, is coated with one or more thin film coatings to enhance the properties and functions of the array and its reaction chambers. The thin film coating or coatings protect the contents of the solution in the reaction chamber from the deleterious effects of the array substrate, without compromising the utility or ease of fabrication of the array. The thin film coatings also provide a uniform surface composition allowing for uniform modification of the reaction chamber surface (e.g., with a monolayer). In one embodiment, the thin film coating produces an optical obstacle in order to eliminate optical scattering of light through the cladding materials into adjacent reaction chambers.

The invention described herein can be a component of a larger system and methods. Such system and methods can be used to process nucleic acids in a multitude of ways. For example, methods are performed to determine the identity of a sequence of nucleic acids, or for single nucleotide polymorphism (SNP) detection in nucleic acid fragments, for nucleic acid expression profiling (comparing the nucleic acid expression profile between two or more states e.g., comparing between diseased and normal tissue or comparing between untreated tissue and tissue treated with drug, enzymes, radiation or chemical treatment), for haplotying (comparing genes or variations in genes on each of the two alleles present in a human subject), for karyotyping (diagnostically comparing one or more genes in a test tissue, typically from an embryo or fetus prior to conception to detect birth defects, with the same genes from "normal" karyotyped subjects), and for genotyping (comparing one or more genes in a first individual of a species with the same genes in other individuals of the same species).

A typical analytical system has a number of components. These include, for example, (1) a nucleic acid template that is to be processed, (2) a delivery chamber, wherein the chamber comprises a coated array of the invention, an apparatus for containing the nucleic acid template, (3) a flow chamber and reagent delivery means that permits flow of nucleic acid processing reagents over the nucleic acid template where the assay reagents generate a detectable signal, e.g., light, as the nucleic acid is processed, (4) an imaging system in communication with the reagent delivery chamber that detects the signal emitted as the nucleic acid is processed and that converts the captured light into data, and (5) a data collection system in communication with the reagent delivery chamber that processes the data to yield meaningful information about the nucleic acid that has been processed.

1. Thin Film Coated Arrays

The present invention includes array compositions which include a substrate with a plurality of reaction chambers on its top surface. Each of the reaction chambers on the array is made up of a bottom and a sidewall, and at least one part, a bottom, sidewall, or top surface of the array is coated with one or more thin film coatings. In one embodiment, the array substrate has a non-transparent thin film coating on at least one bottom or sidewall of substantially all of the reaction chambers or the top surface, and the non-transparent coating is opaque, semi-opaque, shiny opaque, or translucent. In another embodiment, the substrate has a non-transparent coating on at least one bottom or sidewall of substantially all of the reaction chambers or the top surface of the array, and the substrate has a transparent coating on at least one bottom or sidewall of substantially all of the reaction chambers or top surface of the array, where the transparent coating is from 0.1-5.0 microns thick and impermeable to water.

A. The Array Substrate

The array substrate is the solid support that can be modified to contain individual reaction chambers. Any material is used as the substrate. Substrate materials include, but are not limited to, organic polymers and plastics, such as vinyl polymers including polystyrene, polyethylene, polypropylene, polybutylene, polyvinyl chloride, and Teflon®, including copolymers and blends, as well as condensation polymers including polyethylene terephthalate, polyurethanes, polycarbonates, acrylics, polyamides, polyimides, polyesters, and epoxies, and silicones including copolymers and blends. Substrate materials may also include inorganic materials including ceramics, glasses, modified or functionalized glasses, silica or silica-based materials, silicon and modified silicon. Substrate materials may also include fiber optic bundles. In general, all of these types of materials are easily formed into arrays with reaction chambers. However, arrays made from such materials are often incompatible with many organic solvents and thus, applying a thin film coating to such an array substrate enhances the solvent compatibility of the array. Arrays also encounter problems such as physical interference and optical bleeding between neighboring reaction chambers. These types of problems may be solved by applying one or more thin film coatings which are opaque, semi-opaque, shiny opaque, or translucent to prevent photons from traveling through the transparent cladding material into the adjoining reaction chamber.

Generally, the substrate is planar (flat), although other configurations of substrates are used; for example, substrates are concave, convex, three-dimensional, e.g. spherical, textured, or cavitated, e.g., in a cavitated terminus of a fiber optic fiber or in a microwell etched, molded, or otherwise micromachined into the planar surface, e.g. using techniques commonly used in the construction of microelectromechanical systems. See e.g., Rai-Choudhury, HANDBOOK OF MICROLITHOGRAPHY, MICROMACHINING, AND MICROFABRICATION, VOLUME I: MICROLITHOGRAPHY, Volume PM39, SPIE Press (1997); Madou, CRC Press (1997), Aoki, *Biotech. Histochem.* 67: 98-9 (1992); Kane et al., Biomaterials. 20: 2363-76 (1999); Deng et al., *Anal. Chem.* 72:3176-80 (2000); Zhu et al., *Nat. Genet.* 26:283-9 (2000). In one embodiment, the substrate is planar. A substrate may also contain features e.g., spherical cavities, cylinder wells, columns, posts, and tilted cylinders. Such features on the surface of the substrate are formed by etching, plating, imprinting, stamping, molding, machining, etc.

In general, the substrate allows optical detection and does not itself appreciably fluoresce. The substrate is made of a material that facilitates detection of the chemical reaction event or assay result. For example, in a typical nucleic acid sequencing reaction, binding of a dNTP to a sample nucleic acid to be sequenced can be monitored by detection of photons generated by enzyme action on phosphate liberated in the sequencing reaction. Thus, having the substrate made of a transparent or light conductive material facilitates detection of the photons. In some embodiments, the substrate is optically transparent. In another embodiment, the surface of the substrate is optically interrogated.

1. Fiber Optic Faceplate ("FOF")

In one embodiment, the substrate of the array is fashioned from a "sliced" fiber optic bundle or a fiber optic faceplate ("FOF"). A FOF is fabricated by fusing many optical fibers together into a monolithic structure (i.e. a bundle) which retains the light transmission properties of the individual fibers. A fiber bundle is "sliced" to form a "wafer," a FOF. The resulting FOF possesses similar handling properties to that of a lane of glass or microscope slide. A FOF is a substrate onto which wells or chambers re etched to create an array of reaction chambers.

Figure 2:
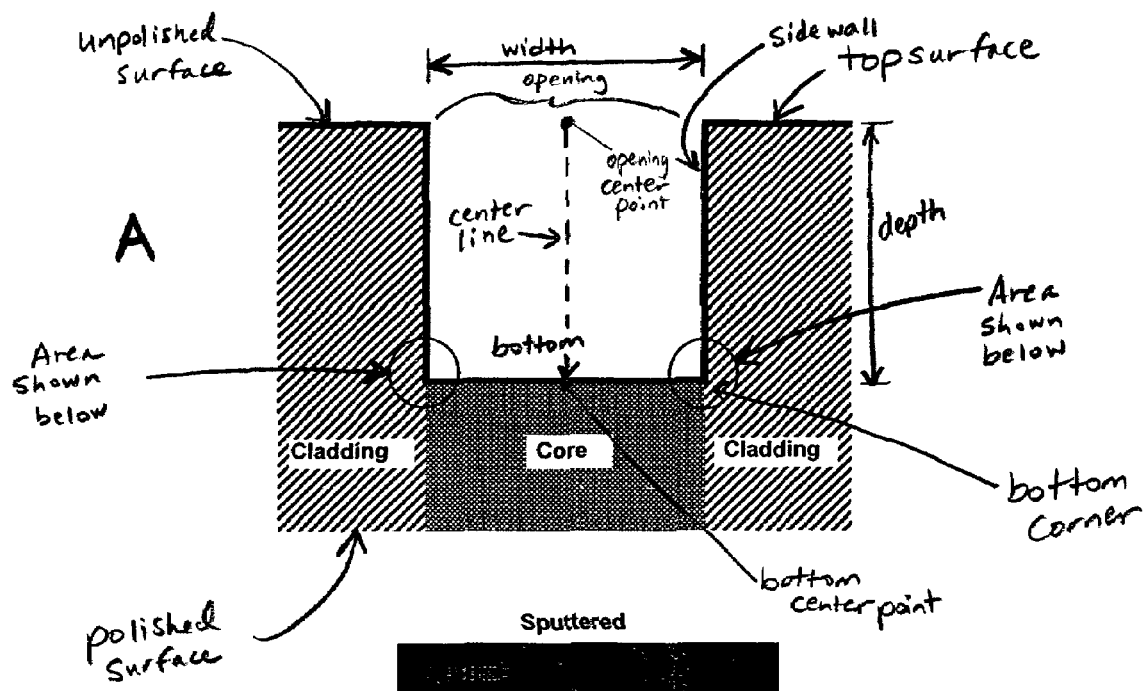
FIG. 2 is a series of cross-sectional SEM images of fiber optic faceplates having reaction chambers which have been coated with $SiO_2$ showing coating thickness and quality for three vapor deposition coating methods.

The individual fiber optic fiber strands which make up a FOF are composed of two materials, an inner "core" material and an outer layer "cladding" material (FIG. 2). The fiber optic core includes a material which is transparent and has a high refractive index. Examples of core materials include heavy metal oxides such as lead, barium, lanthanum, and niobium oxides. The fiber optic cladding includes a material which is transparent and has a low refractive index. One typical cladding material is doped silicon dioxide. Doping agents include metal oxides, such as boron, and aluminum.

The individual fiber strands which make up a FOF each have a diameter. The individual fiber strands can be any size in diameter (e.g., between 3 µm to 100 µm). In one embodiment, the individual fibers are between 6 µm to 12 µm in diameter. Once a fiber optic bundle has been fused to form a monolithic structure, the fiber strands are not individually manipulated; that is, one fiber strand generally cannot be physically separated at any point along its length from another fiber strand. Fused fiber optic bundles and face plates are obtained commercially from manufacturers.

A fiber optic bundle is "sliced" to form a "wafer," a FOF. In one embodiment, the fiber optic bundle is sliced perpendicular to the fused optical fibers. In another embodiment, the fiber optic bundle is sliced at an angle which is not perpendicular to the fused optical fibers (see, e.g., FIGS. 20a-c). When the fiber optic bundle is sliced at an angle (the "slice angle") which is not 90 degrees to the fused optical fibers, the FOF produced contains fiber strands that are not perpendicular to the bottom of the FOF. When the FOF is etched, the reaction chambers that are formed are also not 90 degrees to the bottom of the FOF. The reaction chambers that are formed have a sidewall that is slanted ("tilted reaction chambers").

One surface of a FOF (i.e., the non-reaction chamber side) is typically highly polished so as to allow optical-coupling (e.g., by immersion optic or other optical coupling fluids) to a detection device (FIG. 2). In one embodiment, optical-coupling may be facilitated by a second fused fiber bundle. This second fused fiber bundle typically has a significantly smaller fiber size than the first FOF containing the reaction chambers, and serves to act as a conduit for the transmission of light product to the attached detection device, such as a CCD imaging system or camera.

In one embodiment, the array substrate is a FOF. The overall shape of a FOF is rectangular, although it is understood by those skilled in the art that a FOF is not limited to a specific shape and suitable FOFs include a variety of other shapes and overall dimensions. A FOF has at least a top and bottom surface which are opposed, wherein there is a distance between the top surface and the bottom surface. In one embodiment, the fiber strands within the FOF are oriented substantially perpendicular to the top and bottom surfaces of the FOF. In another embodiment, the fiber strands within the FOF are not oriented perpendicular to the top and bottom surfaces of the FOF. In one embodiment, a FOF further includes at least one index feature to provide a physical basis for ensuring proper orientation of a FOF in both automated equipment and for manual processes. For example, an index feature is used to properly position a FOF in the instrument for analysis.

Figure 8A:
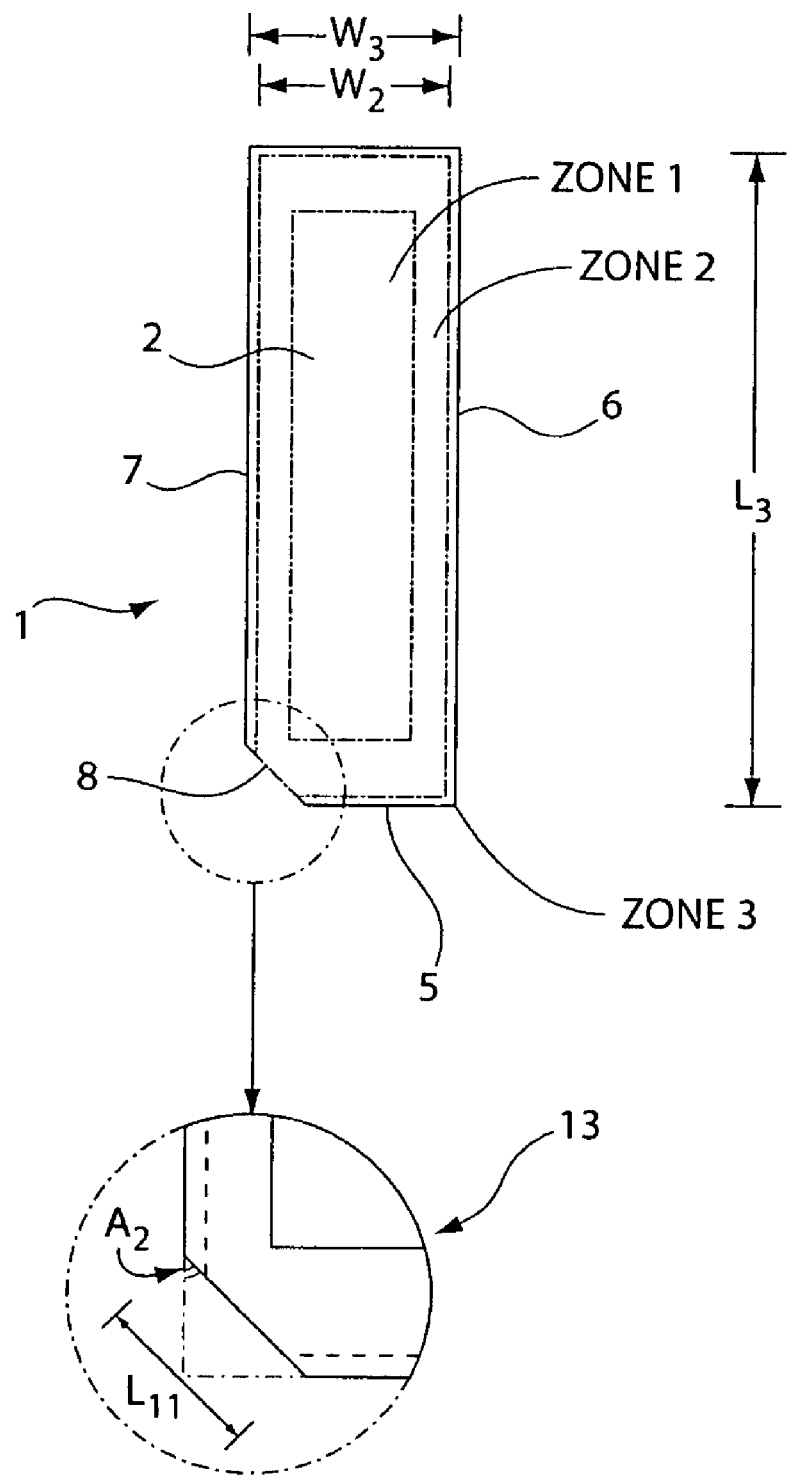
FIG. 8a is a drawing of a 25×75 mm fiber optic faceplate (top view)
Figure 8B:
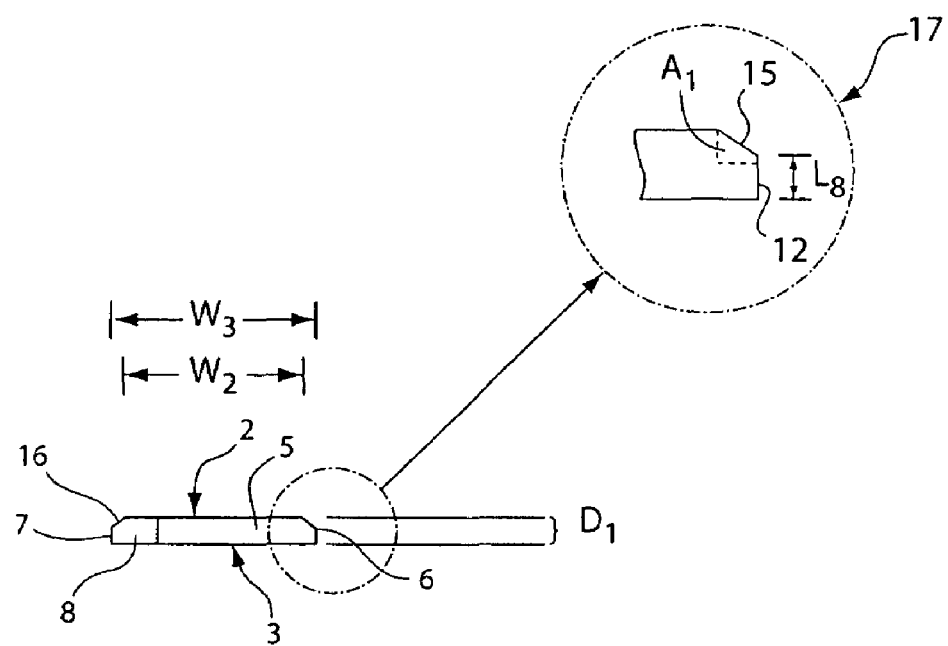
FIG. 8b is a drawing of a 25×75 mm fiber optic faceplate (front edge view)
Figure 8C:
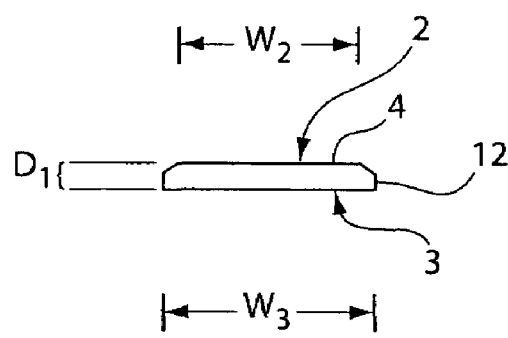
FIG. 8c is a drawing of a 25×75 mm fiber optic faceplate (back edge view)

FIGS. 8a-8c illustrate a FOF 1 for use with this invention. In one embodiment, a FOF 1 has a planar first surface 2 and a planar second surface 3, which are opposed. A FOF 1 is optically conductive such that optical signals from the reaction chambers are detected through the first planar surface 3, wherein there is a distance $D_1$ between the first surface and the second surface. The distance $D_1$ is any distance. In one embodiment, typically the distance $D_1$ between the first surface 2 and the second surface 3 is no greater than 10 cm. In another embodiment, the distance $D_1$ is no greater than 5 mm. In another embodiment, $D_1$ is between 0.5 mm to 5 mm. In a further embodiment, $D_1$ is 2 mm. The first surface 2 and second surface 3 of a FOF 1 are polished or alternatively non-polished.

In one embodiment, one surface is polished and the opposing surface is non-polished. In one aspect of this invention, the first surface 2 is polished and the second surface 3 is non-polished. In a further embodiment, the first surface 2 is polished and the second surface 3 has reaction chambers. In another embodiment, the first surface 2 has reaction chambers and the second surface 3 is polished.

A FOF 1 has at least a first and second side and at least a first and second end. In one embodiment, a FOF 1 has a first end 4 and a second end 5 separated by a distance; a first side 6 and a second side 7 separated by a distance; and one corner side 8 extending between an end and a side. In one embodiment, shown in FIG. 8a, a corner edge 8 extends between a second side 7 and a second end 5. The ends and sides are connected to form the outer perimeter of a FOF 1. For example, a first side 6 and the second side 7 both extend perpendicularly between the first and second ends 4, 5.

The sides and/or ends of an FOF may be beveled at an angle in order to make it possible for the FOF to be mounted in an instrument. Any combination of sides and ends are beveled or alternatively, none of the sides or ends are beveled. In one embodiment, all of the sides and ends are beveled at an angle. A beveled side edge is beveled at an angle to form an inclined portion and a flat portion or alternatively, the beveled side has no flat portion. In one embodiment, the first side 6 is beveled at an angle $A_1$ to form an angled first side edge 17 (FIG. 8b). The angled first side edge 17 is formed by an incline portion 15 and a flat portion 12. The flat portion 12 of the angled first side edge 17 has a height of $L_8$. Similarly, the second side 7 is beveled at an angle to form an angled second side edge 16. The first and second side edges 6 and 7 are beveled to any angle. In one embodiment, the side edges are beveled to an angle between 10 and 80 degrees. In another embodiment, the angle is substantially 45 degrees, wherein substantially means that the angle is a little more or a little less than 45 degrees. In one aspect of the invention, the opposing side edges are beveled to allow the FOF to slide into a suitable retaining structure (e.g., a cartridge) located inside the analytical instrument that will capture, properly locate and mount the FOF relative to the fluidic reaction chamber and the camera.

In one embodiment, the first and second sides 6 and 7 are each beveled to form a 45 degree angle and the length $L_8$ of the resulting flat portion is 0.20 mm-0.45 mm. The beveled sides 6 and 7 are located along the planar optically conductive surface 2.

Those of ordinary skill in the art will appreciate that the first surface and second surface of a FOF is any length and any width. In one embodiment, the length and width are the same. In embodiments where at least one of the sides is beveled, the width of the first surface is slightly smaller than the width of the second surface due to the angled side edge. For example, in one embodiment the width $W_2$ of the first surface 2 is about 38 mm and the width $W_3$ of the second surface 3 is about 40 mm (FIG. 8b). In similar embodiments where at least one of the ends is beveled, the length of the first surface is slightly smaller than the length of the second surface.

In a first embodiment, second surface 3 has a length $L_3$ of about 75 mm, the width $W_3$ of the second surface 3 is about 40 mm. The first surface 2 has the same length $L_3$ as the second surface 3 and the width $W_2$ of the first surface 2 is about 38 mm.

In a second embodiment, second surface 3 has a length $L_3$ of about 75 mm, the width $W_3$ first surface 2 is about 25 mm. The first surface 2 has the same length $L_3$ as second surface 3 and the width $W_2$ of the first surface 2 is about 22 mm.

Suitable FOFs may include, for example, one or more index features. An index feature is located anywhere on a FOF and is not limited to any specific shape or size. In one embodiment, an index feature is located on the perimeter of the FOF. In a further embodiment, the index feature is located in a corner. The purpose of an index feature is to provide a physical basis to allow engagement of a FOF to ensure its proper orientation. As shown in FIG. 8a, a suitable FOF 1 includes an index feature that is a corner notch 13 formed by removing a portion of the corner of the FOF where the side and end of the FOF connect perpendicularly. A FOF 1 has one or more corner notches. In one embodiment, a FOF 1 has one corner notch 13. In another embodiment, one corner notch 13 is formed by removing the corner, where the second side 7 connects the second end 5. The corner portion is cut off at an angle $A_2$ to create a corner notch 13. An angle $A_2$ is not limited to a particular degree and includes other angles and shapes. In one embodiment, an angle $A_2$ is removed from the corner portion of FOF 1 where the second side 7 connects to the second end 5 and the angle $A_2$ is about 45 degrees. The resulting corner side 8 has a length $L_{11}$ which is any length. In one embodiment, $L_{11}$ is about 6 mm. The corner notch 13 is matched with a complementary feature designed into the component in which a FOF 1 fits e.g., a feature designed into the FOF mounting hardware of the analysis system or a feature designed into a gasket of an etching apparatus.

A FOF 1 may be labeled with one or more identifier codes. A FOF is marked with an identifier code for a variety of purposes. For example, an identifier code enables tracking and/or authenticating of a FOF. An identifier code also allows visual orientation of a FOF 1 when it is mounted in the analysis system (i.e., the system does not operate to analyze a FOF 1, unless the analysis system can properly read the identifier code). The identifier code may be any type of code e.g., a bar-code, a two dimensional bar-code such as a Data Matrix code, etc. In one embodiment, a FOF 1 is coded with a bar-code. In another embodiment, a FOF 1 is coded with a Data Matrix code. In one embodiment, a FOF 1 has both a bar-code and Data Matrix code. An alpha-numeric code that can be read by a human may also be incorporated. The identifier code is read by an instrument, for example, a CCD camera, or a bar-code reader.

In one embodiment, an identifier code can be directly etched into the FOF surface with a laser. In an alternative embodiment, the identifier code is printed onto the surface of the FOF.

B. The Array Surface

Prior to coating with one or more thin film coatings, at least one surface of the substrate is modified to contain one or more individual reaction chambers, arranged so as to allow for the discrete localization of each reaction mixture or assay solution in a defined space, as well as for detection of the analytical result. The top or the bottom surface, or both surfaces can be modified to contain individual reaction chambers. Thus, as used herein, the term "reaction chamber" refers to a localized "well" or "chamber" on the substrate that facilitates interaction of reactants, e.g., in a nucleic acid sequencing reaction. Typically, the reactants are distributed into the reaction chambers of the array in a medium which facilitates the chemical reaction or bioassay and which flows through the reaction chamber. For example, for DNA sequencing, a nucleic acid template is distributed into each reaction chamber on one or more solid supports, beads, or particles in a solution which flows through the reaction chamber.

Figure 6:
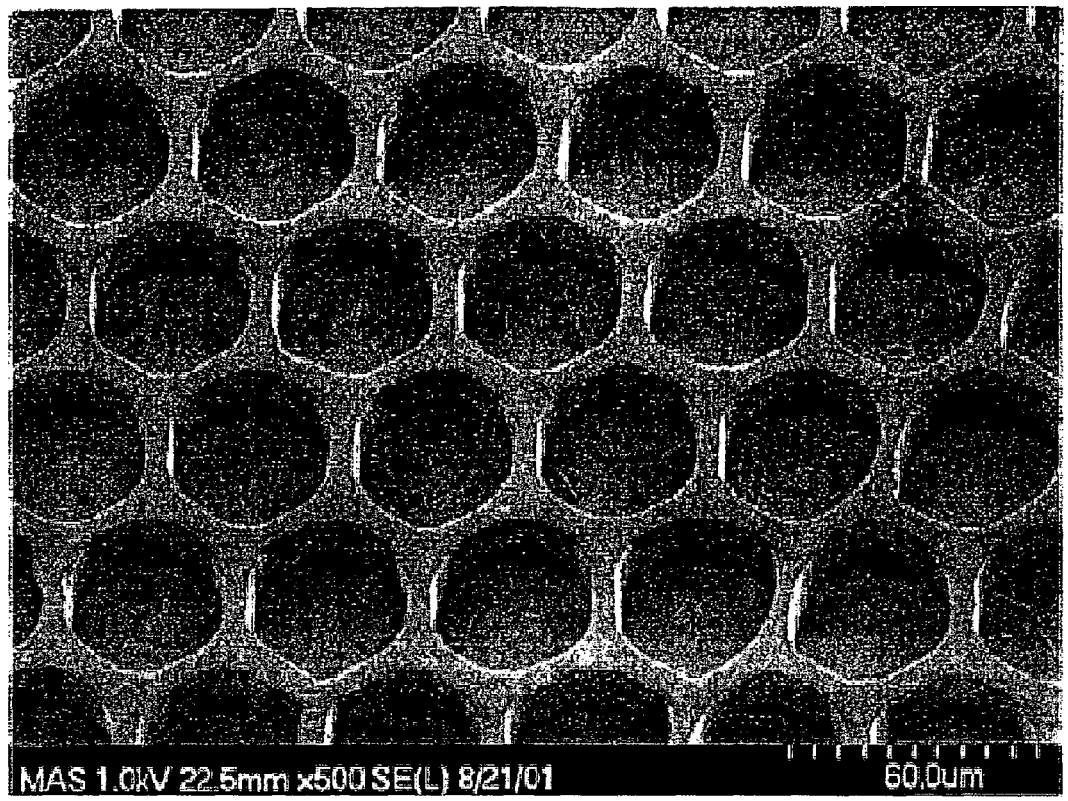
FIG. 6 is a series of Scanning Electron Micrographs of a portion of a fiber optic faceplate surface (uncoated) comprising reaction chambers.
Figure 6:
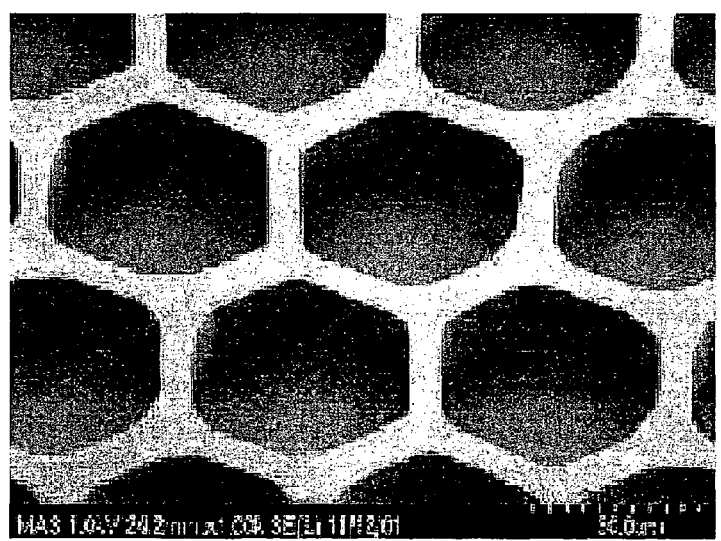
Figure 7A:
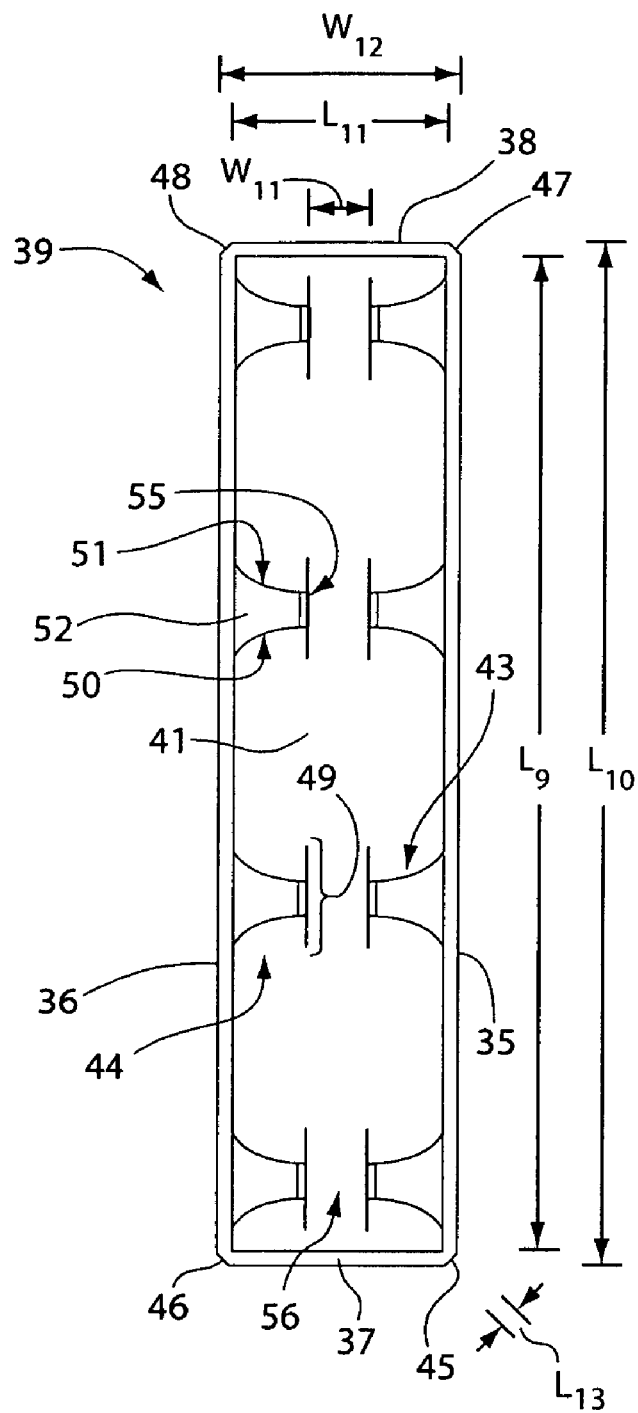
FIG. 7a is a drawing of a PEEK clamp (top view)
Figure 7B:
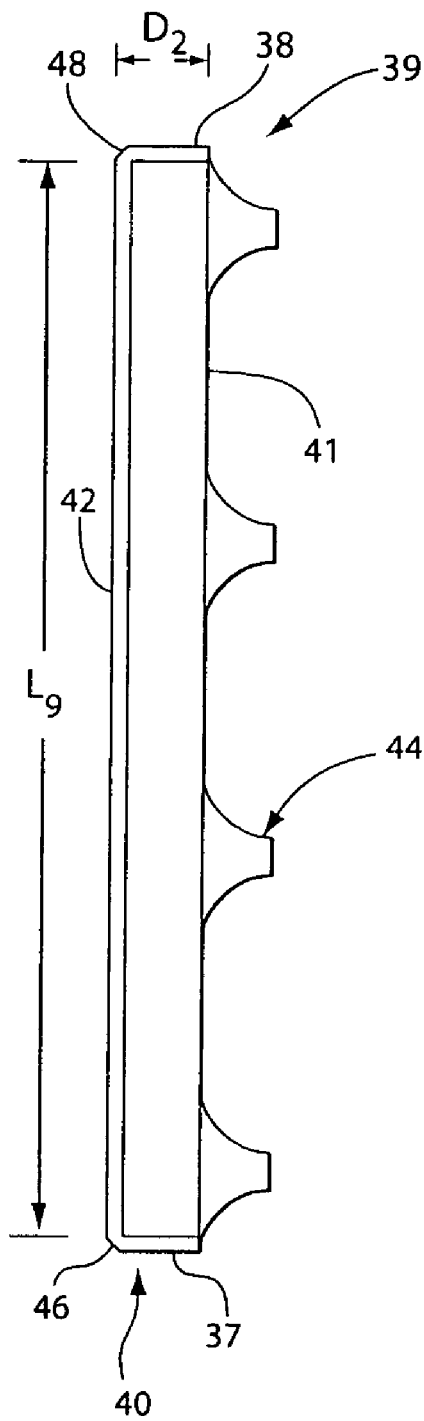
FIG. 7b is a drawing of a PEEK clamp (side view)
Figure 7C:
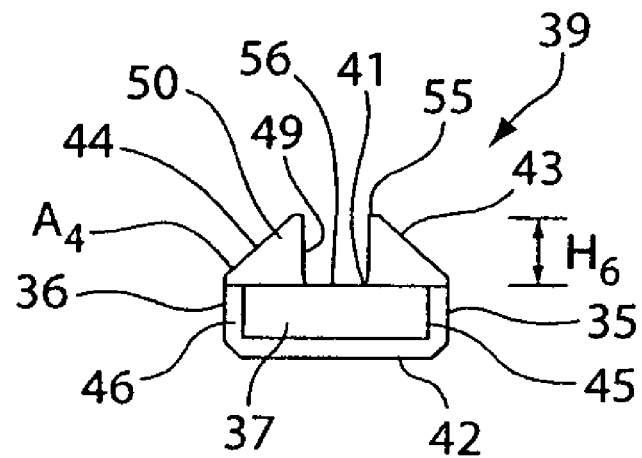
FIG. 7c is a drawing of a PEEK clamp (front end view)
Figure 7D:
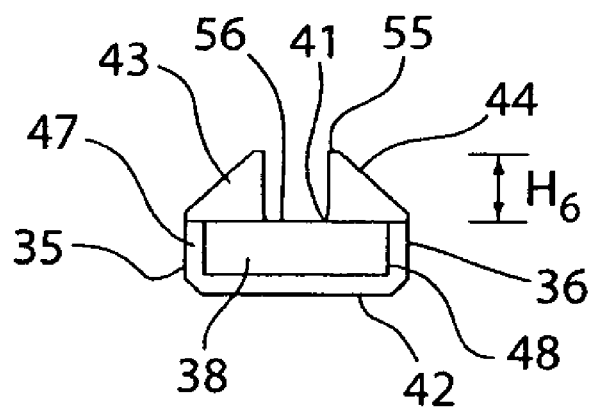
FIG. 7d is a drawing of a PEEK clamp (back end view)

The reaction chambers can be formed on either the top or bottom surface or both surfaces of the array substrate. A reaction chamber is a hollowed-out space having a width, a depth, and an opening. The opening of a reaction chamber can be any shape e.g., substantially round, square, oval, rectangular, hexagonal, crescent, or star-shaped. The reaction chamber can be any shape e.g., substantially round, square, oval, rectangular, hexagonal, crescent, or star-shaped. In one embodiment, the reaction chamber is circular or cylindrical. In another embodiment, the reaction chamber is multi-sided so as to approximate the shape of a square or rectangular box. Referring to FIG. 6, the shape of the reaction chamber in one embodiment is substantially hexagonal. In one embodiment, the reaction chambers are uniform in shape.

Each reaction chamber on the array includes a bottom and a sidewall which define the boundary of the reaction chamber. The bottom of the reaction chamber can be any shape e.g., substantially round, square, oval, rectangular, hexagonal, crescent, or star-shaped. The bottom of the reaction chamber can be either planar (i.e. flat), concave or convex. The bottom of the reaction chamber is opposed to the opening of the reaction chamber. The sidewall of the reaction chamber can be any shape. For example, the sidewall can be cylindrical in shape and connected to a round bottom. The sidewall of the reaction chamber can also have multiple sides e.g., the sidewall of a reaction chamber with a hexagonal-shaped bottom has six sides which make up the sidewall of the reaction chamber. The sides of the reaction chamber which make up the sidewall are continuous or alternatively, the sides are discontinuous. For example, in a hexagonal shaped reaction chamber, reaction chamber can be closed, such that the sides are continuous and connect to each other or the reaction chamber can be open, such that the sides are not continuous and do not connect to each other. The sidewall can have a smooth surface or an irregular surface.

The bottom and the sidewall connect to form the bottom corner of the reaction chamber at the junction where the bottom and sidewall are joined. The angle at which the sidewall and bottom are connected can be substantially 90 degrees around the perimeter of the bottom or alternatively, the angle can vary from less than 90 degrees to greater than 90 degrees around the perimeter of the bottom. The connection between the bottom and sidewall can be continuous around the perimeter of the bottom. Alternatively, in some embodiments, the connection between the bottom and the sidewall is not continuous around the perimeter of the bottom.

In one embodiment, the inner surface of the reaction chamber takes the form of a well or chamber in the substrate, having a width and depth, into which reaction mixtures or assay solutions are deposited (FIG. 2). In one embodiment, the reaction chambers are of sufficient dimension and order to allow for (i) the introduction of the necessary reactants into the chambers, (ii) chemical reactions or assays to take place within the chamber and (iii) inhibition of mixing of reactants and/or analytes between chambers.

In another embodiment, the sidewall of the reaction chamber is not continuous i.e., the sidewall is interrupted with an opening between adjacent reaction chambers such that reactants can flow from one reaction chamber to another.

Figure 26A:
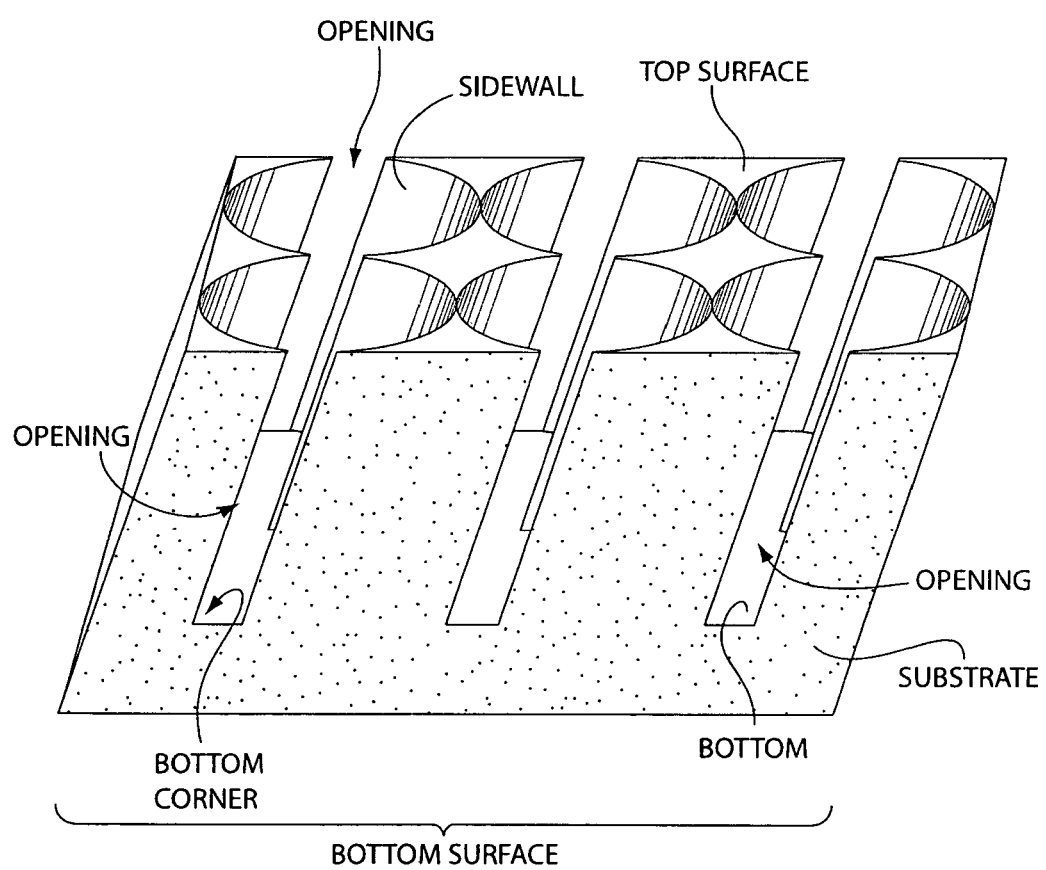
FIG. 26a shows an array where the reaction chambers have a sidewall that is not continuous i.e., the sidewall is interrupted with a slit in the sidewall between two adjacent reaction chambers.
Figure 26B:
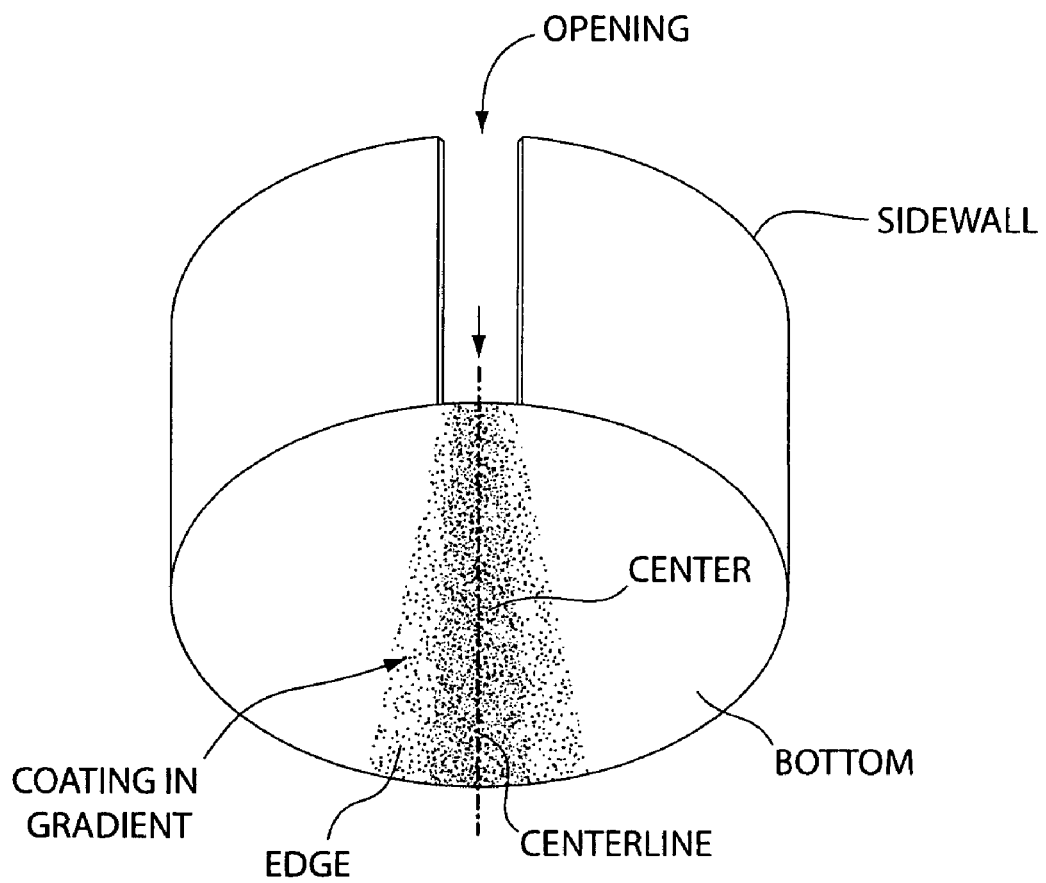
FIG. 26b illustrates the pattern formed on the bottom of a reaction chamber (with a non-continuous sidewall) when a coating is deposited through a slit opening in the sidewall of a reaction chamber. The coating is deposited in a gradient such that the coating is thicker near the center line of the bottom of the reaction chamber and the coating becomes thinner away from the center line to the edge.

The opening between the chambers can be any size and shape. For example, the opening can be one or more holes, channels, tubes, or slits. Such an opening in the sidewall facilitates the fast exchange of reagents. For example, reagents immobilized on the surface of beads ("reagent beads") which are small enough to fit the opening in the sidewall are free to flow between adjacent reaction chambers of the array, while reaction substrates immobilized on larger beads, which can not fit through the opening in the sidewall, are retained within the individual reaction chambers e.g. reaction substrates bound to beads ("substrate beads") or alternatively, reaction substrate beads can be bound to the bottom of the reaction chamber. The efficiency of reagent exchange between reaction chambers with an opening in the sidewall is generally improved and the time for chemical reactions or bioassays is reduced. In addition, the opening in the sidewall of the reaction chamber permits faster and more complete removal of reaction products and by-products from the chamber. In one embodiment, the opening is a slit in the cladding material between two adjacent reaction chambers on a FOF (FIG. 26a-b).

Figure 21A:
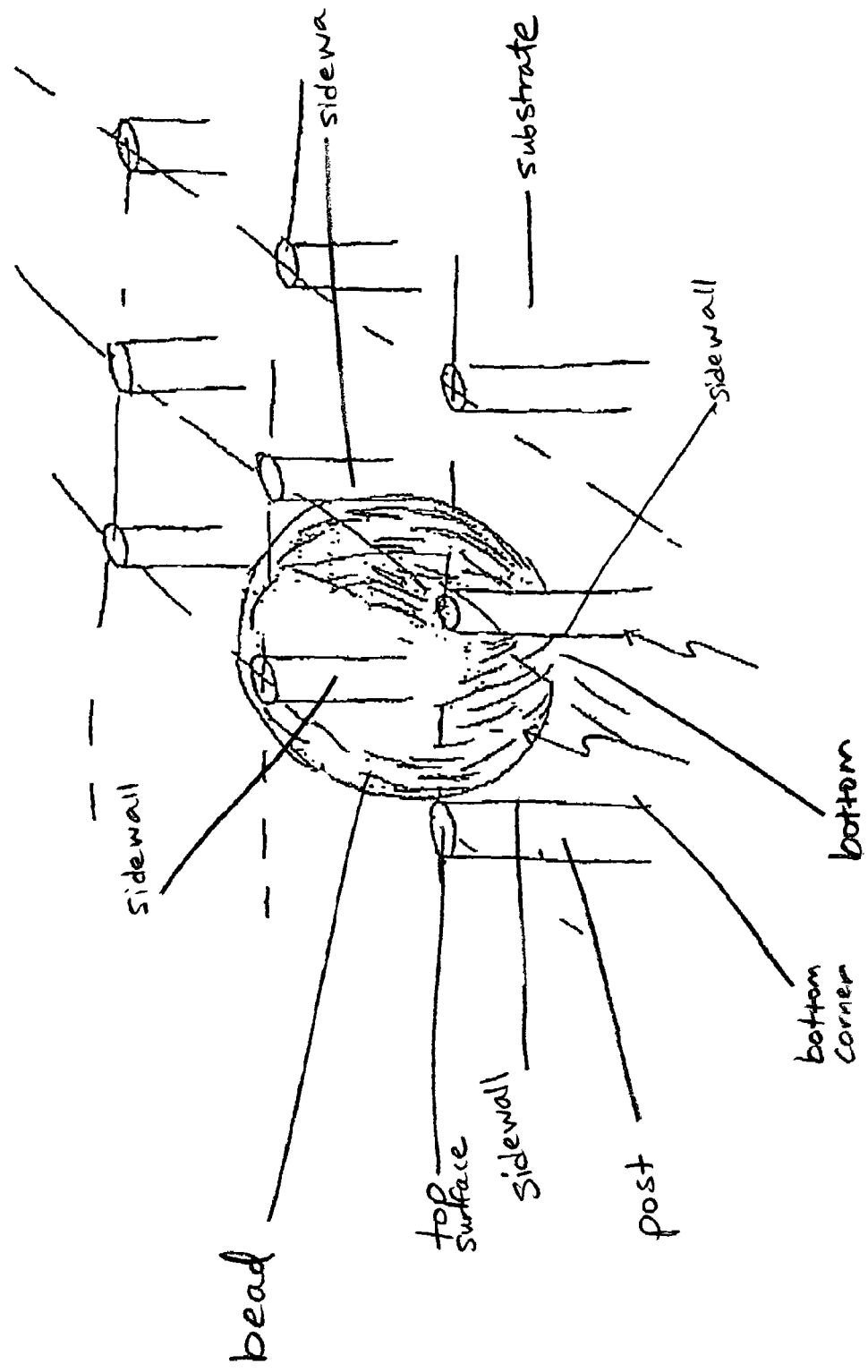
FIG. 21a is a sketch of an array where the reaction chambers of the array are each formed by 4 boundary posts built on top of the substrate, such boundary posts "trap" each bead or particle in the space defined by the set of 4 boundary posts. The bottom and sidewall of the reaction chamber holding a bead is shown.
Figure 21B:
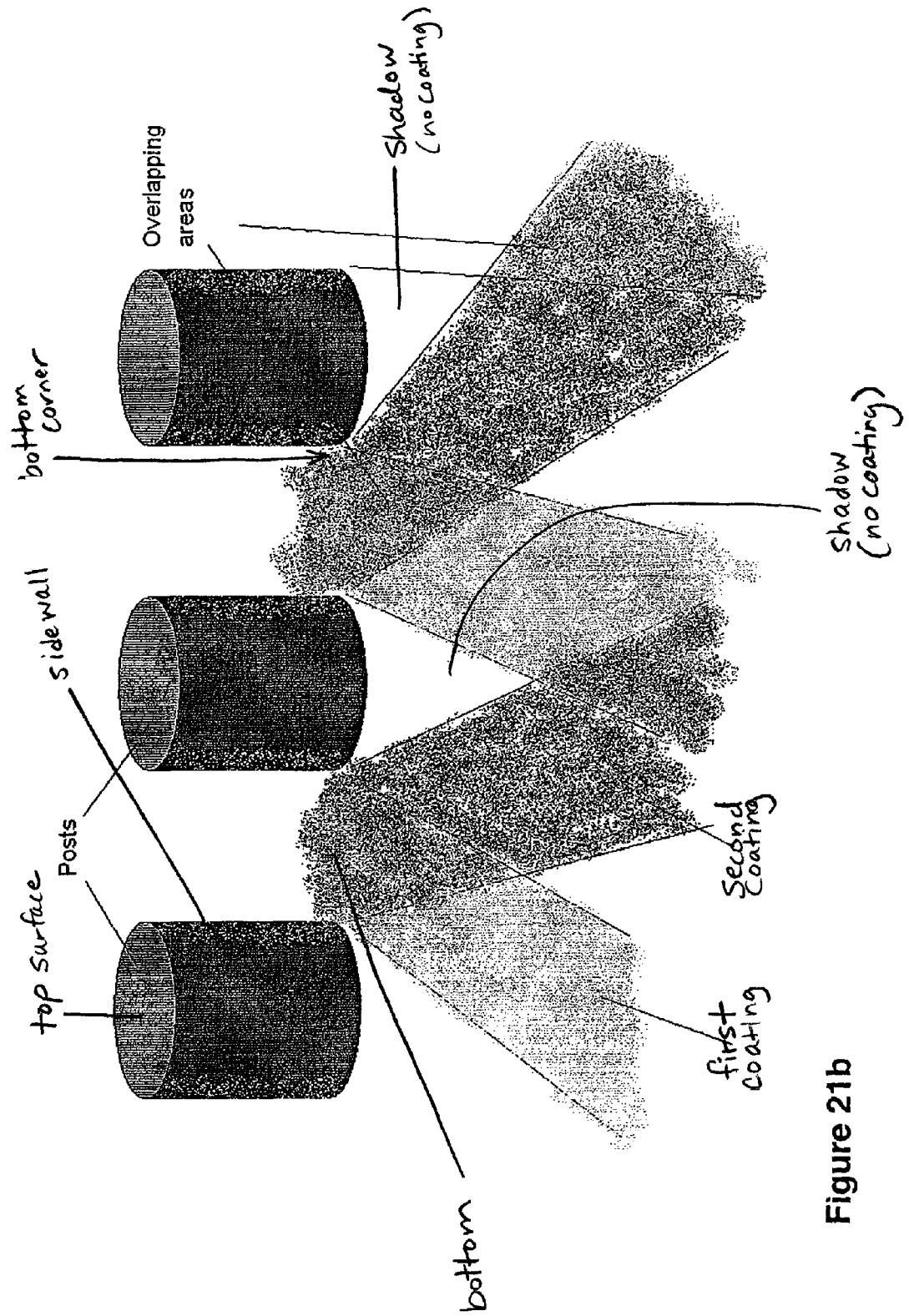
FIG. 21b illustrates the metal deposition process for an array where the reaction chambers are formed by a series of boundary posts on top of a substrate. The FIG. 21b shows overlapping shadows during multiple depositions of thin film coatings at different angles. Shadows created by the boundary posts produce unique patterns and shapes on overlapping areas.
Figure 22:
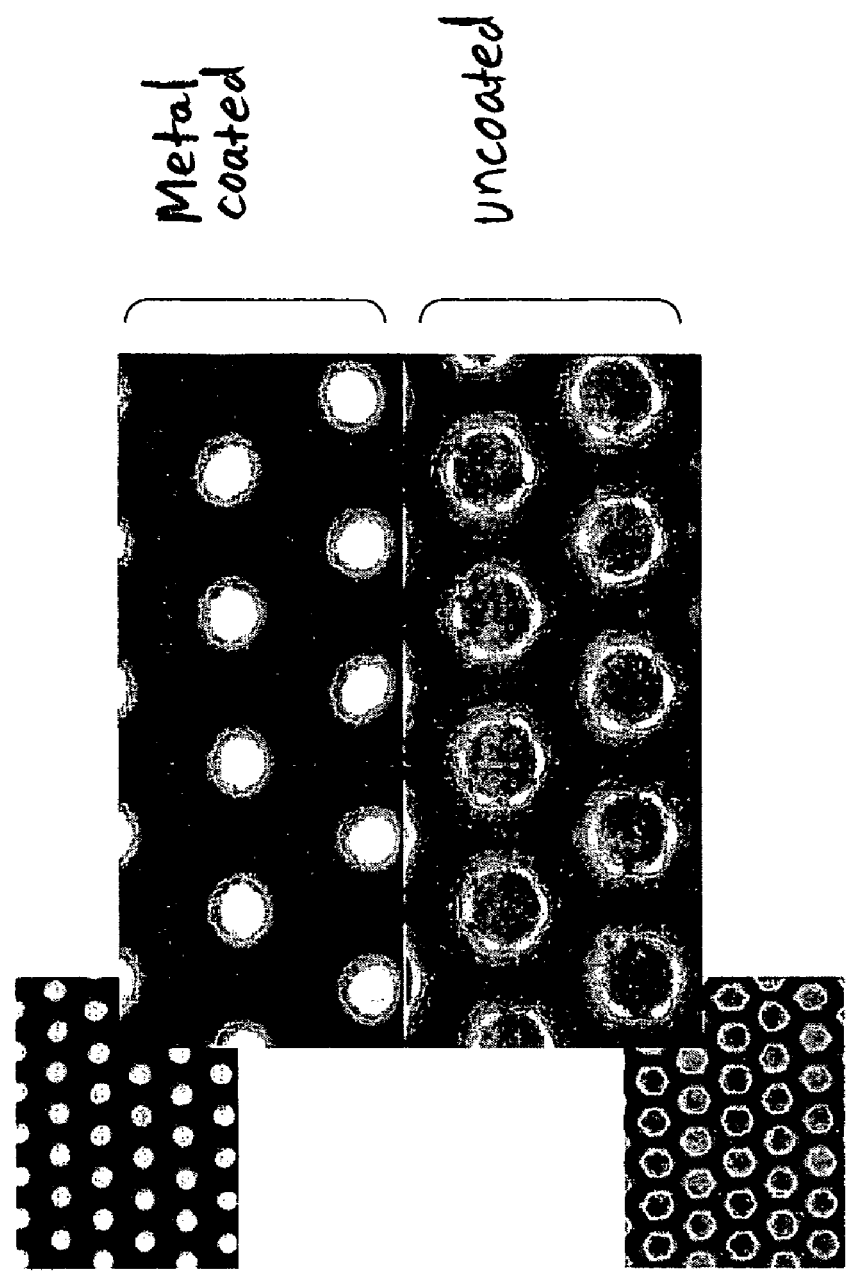
FIG. 22 shows optical images taken of two areas of a fiber optic faceplate that has been etched and coated on one half. Area A is metal (silver) coated and Area B is uncoated. The silver was applied to the array using a thermal evaporation process.

In another embodiment, the sidewall is not continuous and contains one or more boundary posts that define the geometry of the reaction chamber. The boundary posts have any shape (e.g., cylindrical, hemispherical, crescent-shaped, etc.). In one embodiment, the reaction chambers on the array are formed by a series of cylindrical boundary posts which extend upward from the substrate (e.g., glass, non-fiber optic faceplate, etc.) to form a "post-array." In one embodiment, each chamber is defined by four boundary posts and the posts form the non-continuous sidewall of each reaction chamber on a post-array. In one embodiment, the post-array is used to "trap" a reaction substrate bead (FIG. 21a-b). The number and size of the boundary posts, as well as the pattern of the boundary posts on the substrate can vary. This "open" type of reaction chamber facilitates a fast exchange between reagents that are able to flow through the reaction chambers of the array and the reaction substrates which are retained in the individual reaction chambers e.g., reaction substrates attached to beads or particles which are trapped between boundary posts. For more examples see, e.g., U.S. patent Ser. No. 10/260,704, Pengguang Yu, Kevin Kornelsen. US patent application number 20030091475, May 5, 2003.

In one embodiment, substantially all of the reaction chambers of the array have a sidewall that is connected at a perpendicular angle to the bottom of the substrate, and the opening of the reaction chamber and the bottom are opposed such that the center points of the bottom and the opening are aligned. Alternatively, in another embodiment, substantially all of the reaction chambers of the array have a sidewall that is not connected at a perpendicular angle to the bottom of the substrate, and the opening of the reaction chamber and the bottom are opposed such that the center points of the bottom and the opening are offset i.e., not aligned (see, e.g., FIG. 20b). The reaction chamber that is formed when the angle is not perpendicular and the center points are not aligned is referred to as a "tilted reaction chamber." The sidewall of a tilted reaction chamber is slanted and the angle at which the bottom and sidewall connect varies from between less than 90 degrees to greater than 90 degrees around the perimeter of the bottom corner of the reaction chamber. In one embodiment, the angle formed at the bottom corner area of the reaction chamber varies from between about 60 to 120 degrees. In another embodiment, the angle formed at the bottom corner area of the reaction chamber varies from between 80 to 100 degrees. In another embodiment, the angle formed at the bottom corner area of the reaction chamber varies from between 85 to 95 degrees. In another embodiment, the angle formed at the bottom corner area of the reaction chamber varies from between 88 to 92 degrees. In another embodiment, the angle formed at the bottom corner area of the reaction chamber varies from at 89 to 91 degrees.

Figure 20A:
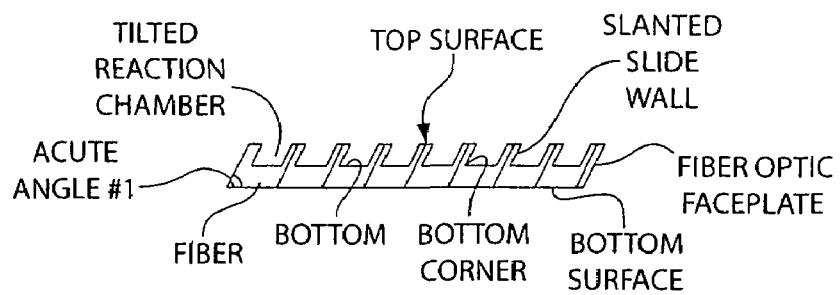
FIG. 20a shows a fiber optic faceplate having fiber strands, which are oriented at an acute angle ("acute angle (#1)") which is less than 90 degrees to the bottom surface of the fiber optic faceplate (i.e. the fiber strands are not perpendicular).
Figure 20B:
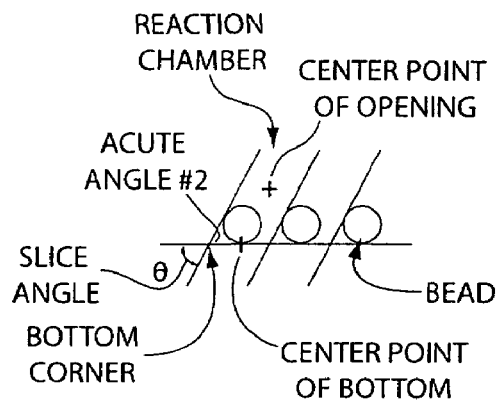
FIG. 20b shows a titled reaction chamber where a bead is located in one corner of the reaction chamber having a sidewall which is slanted at an acute angle (#2) to the bottom of the reaction chamber. The bead can be fixed in this corner position using centrifugal force.
Figure 20C:
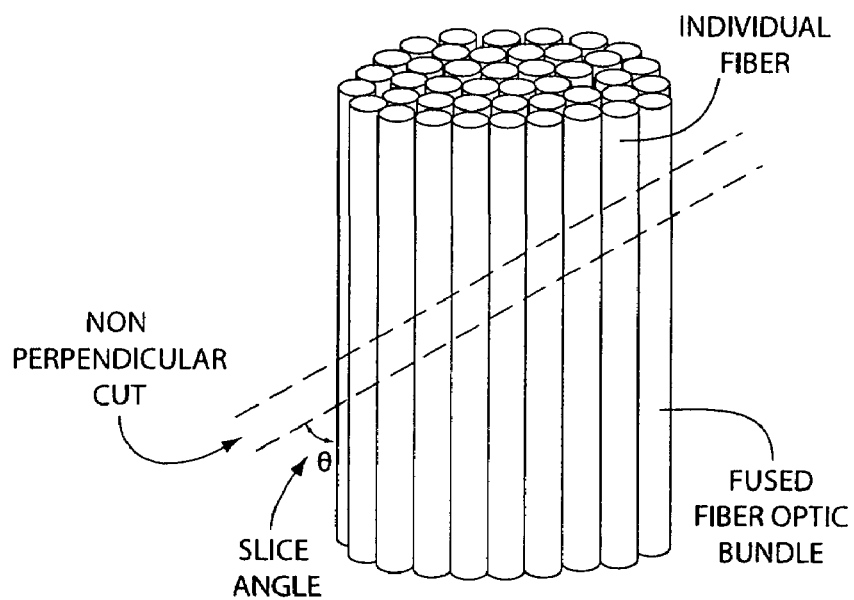
FIG. 20c is a sketch of a fiber optic bundle which is marked with two the lines showing an example of where to cut the fiber optic bundle to make a non-perpendicular cut.

In one embodiment, an array with tilted reaction chambers is formed when a FOF is sliced at a non-perpendicular angle, and the resulting FOF has optical fiber strands that are not perpendicular to the bottom of the faceplate (FIG. 20a-b). When this FOF with non-perpendicular fibers is chemically etched, the reaction chambers that are formed each have a sidewall which is slanted i.e., a tilted reaction chamber. Tilted reaction chambers can be used to "fix" or "hold" a bead in a specific position within a tilted reaction chamber (FIG. 20b). In one embodiment, centrifugal force is used to fix the position of a bead in a tilted reaction chamber. In another embodiment, the bead is fixed or held in one corner of the tilted reaction chamber. In another embodiment, centrifugal force is used to deposit a first bead (e.g., a substrate bead) into each reaction chamber of the array). In another embodiment, centrifugal force is used to deposit a second bead, smaller than the first bead (e.g., a reagent bead), into each chamber. In a further embodiment, centrifugal force is used deposit more than one second bead, which is smaller than the first bead, into each chamber.

Figure 16A:
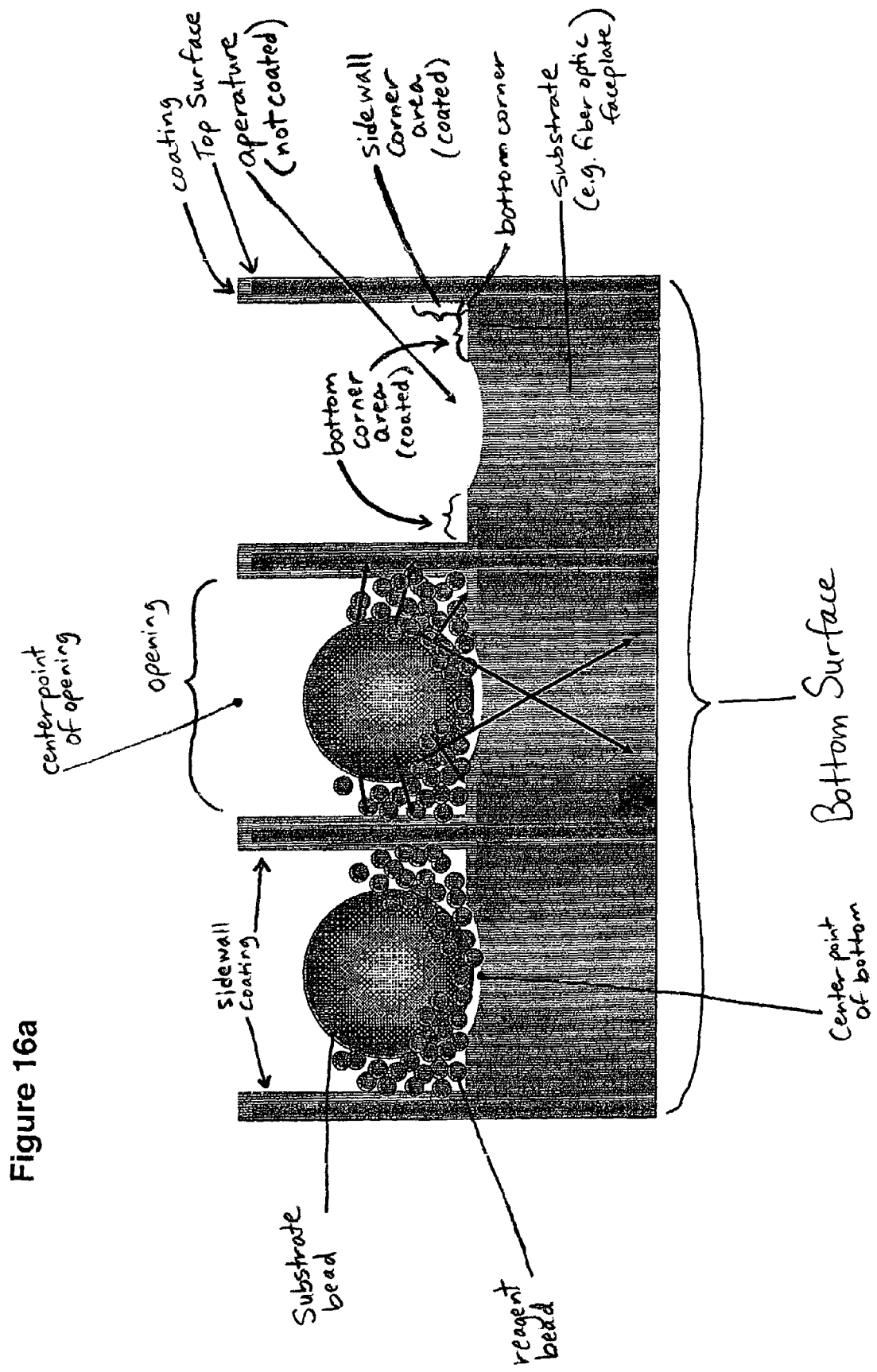
FIG. 16a is a side view of a fiber optic faceplate containing three reaction chambers where one chamber is empty and the other two chambers are charged with reagent substrate beads (larger) and reagent beads (smaller). The reaction chambers have a coating on the sidewall of the reaction chamber and top surface of the array, and the bottom of the reaction chamber is partially coated. The coating shown is applied to the corner area of the reaction chamber, such that the coating is applied to the "sidewall corner area" and the "bottom corner area" where there is an absence of coating on the bottom of the reaction chamber.
Figure 16B:
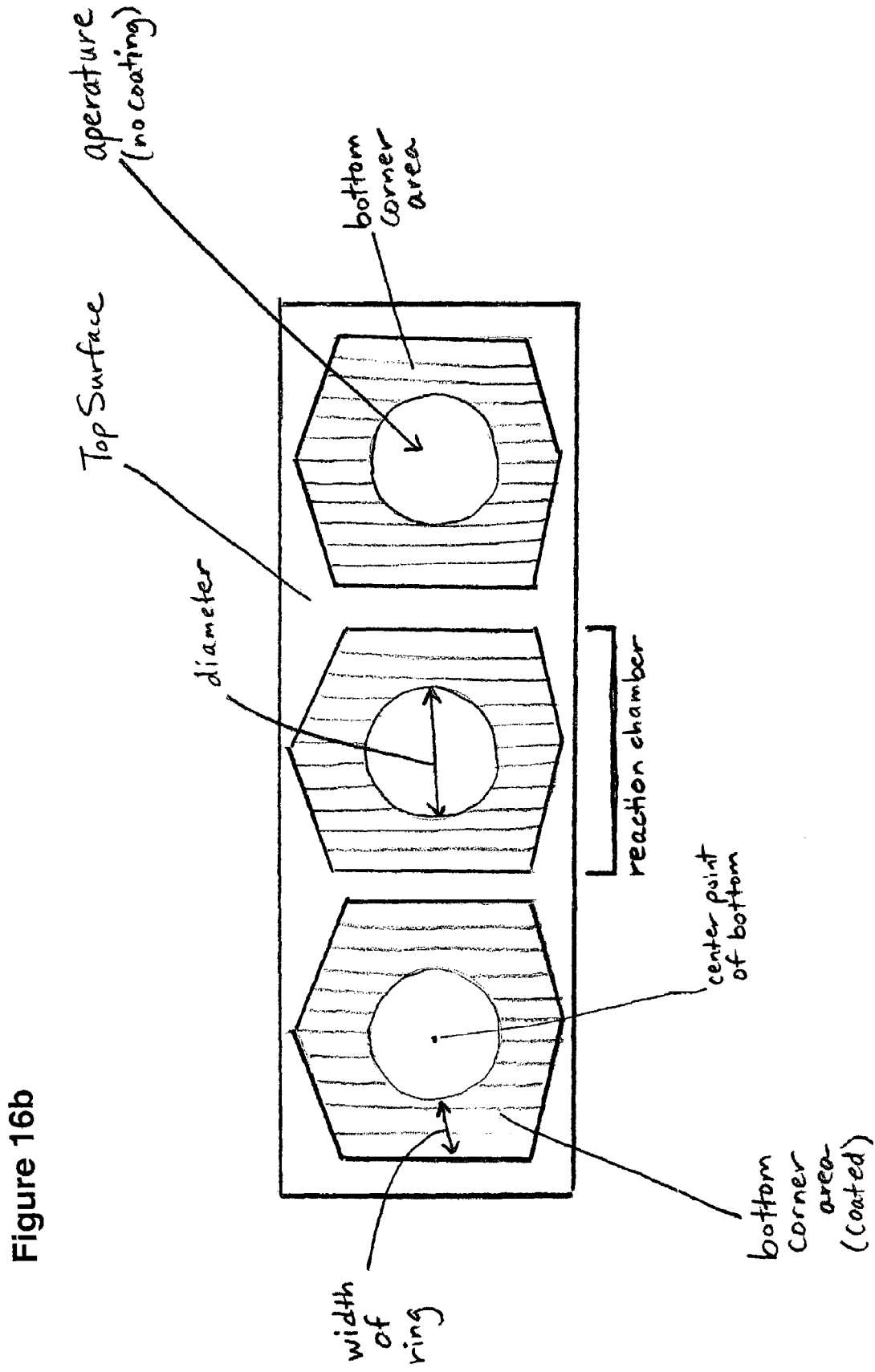
FIG. 16b is a top view of three reaction chambers having a coating applied to the bottom corner area of the reaction chamber, such that there is an absence of coating on the bottom of the reaction chamber which forms an aperture near the center of the bottom. The diameter of the aperture and width of the ring of the corner area are shown.
Figure 17:
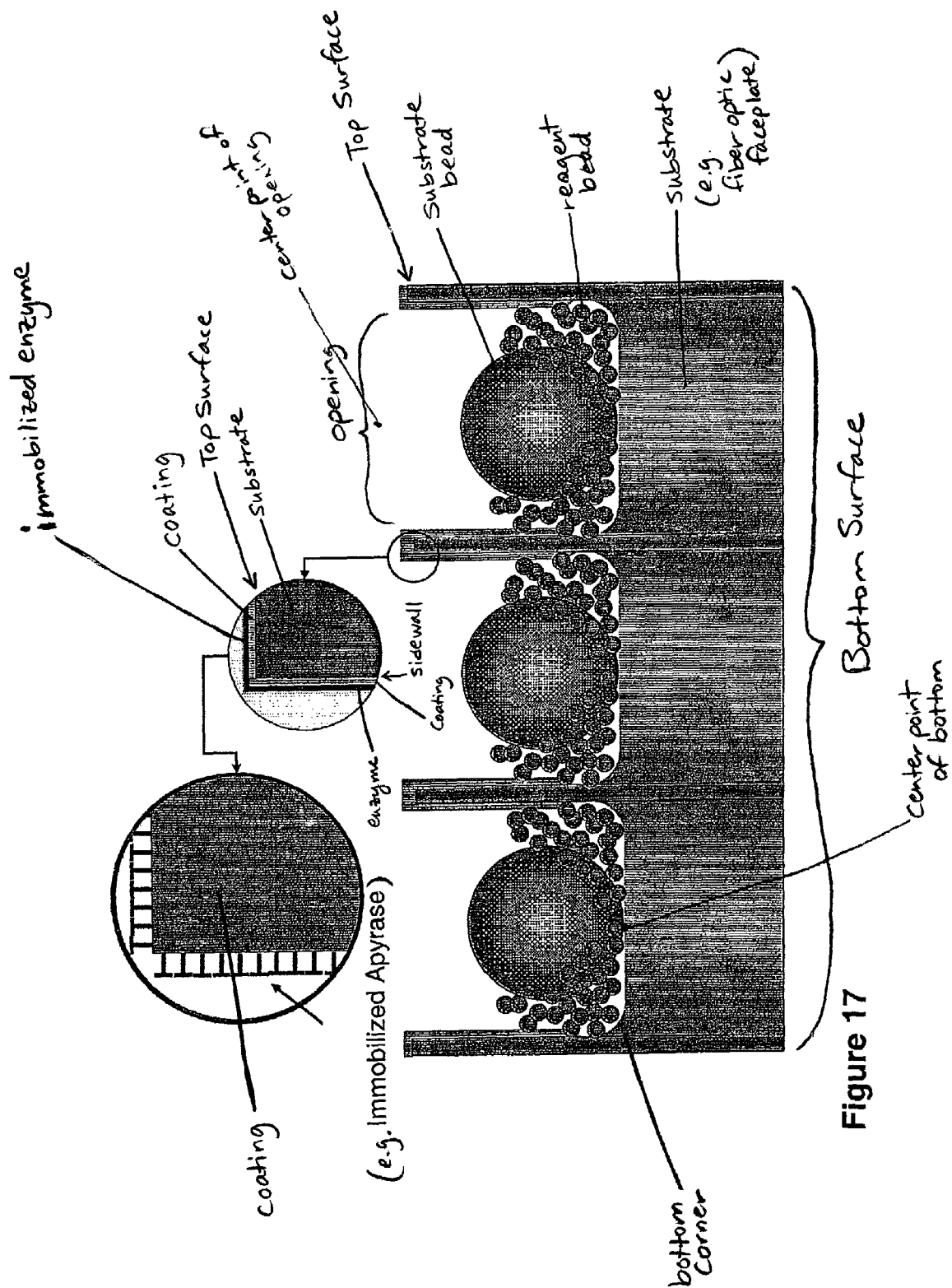
FIG. 17 is a side view of a fiber optic faceplate containing three reaction chambers, charged with substrate beads (larger) and reagent beads (smaller), and the sidewall of each chamber is coated with a coating. The coating has been modified to contain an enzyme (e.g., apyrase) on its surface.

The "Corner Area" of a reaction chamber is the inner surface of the bottom and the sidewall of the reaction chamber, where the bottom and sidewall of the reaction chamber connect to form a junction ("the junction") at the bottom corner (FIGS. 16a-b). The corner area includes both the "bottom corner area" and "sidewall corner area." The corner area extends from the junction along the length of the sidewall towards the top surface of the array and along the length of the bottom towards the center of the reaction chamber. The corner area does not extend the entire length of the sidewall or the entire length of the bottom. In one embodiment, the sidewall corner area extends from the junction to a length at least 90% of the total length of the sidewall. In another embodiment, the sidewall corner area extends from the junction to a length at least 60% of the total length of the sidewall. In another embodiment, the sidewall corner area extends from the junction to a length at least 40% of the total length of the sidewall. In another embodiment, the sidewall corner area extends from the junction to a length at least 20% of the total length of the sidewall. In another embodiment, the sidewall corner area extends from the junction to at least 10% of the total length of the sidewall. In another embodiment, the sidewall corner area extends from the junction to at least 5% of the total length of the sidewall. In another embodiment, the sidewall corner area extends less than 5% of the total length of the sidewall (see, e.g., FIGS. 16a and 16b).

In another embodiment, the bottom corner area extends from the junction to a length at least 40% of the total length of the bottom. In another embodiment, the bottom corner area extends from the junction to a length at least 20% of the total length of the bottom. In another embodiment, the bottom corner area extends from the junction to a length of at least 10% of the total length of the bottom. In another embodiment, the bottom corner area extends from the junction to a length of at least 5% of the total length of the bottom. In another embodiment, the bottom corner area extends from the junction to a length of less than 5% of the total length of the bottom. In another aspect of the invention, the corner area forms the shape of a ring on the bottom of the reaction chamber, where the corner area does not include the area near the center of the bottom of the reaction chamber. In a further embodiment, an opening is formed near the center of the bottom of the reaction chamber by the coating that is partially applied to the bottom of the reaction chamber. In one embodiment, the reaction chambers of the array are in a pattern, i.e. a regular design or configuration, or the chambers can be randomly distributed on the array surface. In one embodiment, there is a regular pattern of reaction chambers on the array such that the chambers may be addressed in the X-Y coordinate plane. "Pattern" in this sense includes a repeating unit. In another embodiment, the array contains a high density of reaction chambers arranged in a pattern on the substrate. In one embodiment, an irregular hexagonal packed array of reaction chambers is on the surface of the array substrate as illustrated by FIG. 6.

The reaction chambers may be spaced any suitable distance apart. Spacing is determined by measuring the distance between the center points of two adjoining reaction chambers (FIG. 2). The reaction chambers are generally spaced between 5 µm and 200 µm apart. In one embodiment, the reaction chambers are spaced between 10 µm and 150 µm apart. In one embodiment, the reaction chambers are between 20 µm and 100 µm apart. In another embodiment, the reaction chambers are between 40 and 60 µm apart. In another embodiment, the reaction chambers have a spacing between the center points of two adjoining chambers of about 43 µm to 50 µm. The size of the reaction chamber is made to accommodate any volume. In one embodiment, the reaction chamber volume is between 10 to 150 pL. In another embodiment, the reaction chamber volume is between 20 to 90 pL. In a further embodiment, the reaction chamber volume is between 40 to 85 pL. In another embodiment, the reaction chamber volume is about 75 pL.

The reaction chambers can have any suitable width. In one embodiment, substantially all of the reaction chambers of the array have a diameter (width) in one dimension of between 3 µm and 100 µm. In another embodiment, substantially all of the reaction chambers have a diameter between 20 µm and 70 µm. In another embodiment, substantially all of the reaction chambers of the array have a diameter between about 30 µm and 50 µm. In a further embodiment, substantially all of the reaction chambers of the array have a diameter of between 38 µm to 44 µm.

The reaction chambers may have any suitable depth. The depth of substantially all of the reaction chambers is generally between 10 µm and 100 µm. In one embodiment, the depth of substantially all of the reaction chambers is between 20 µm and 60 µm. In another embodiment, the depth of substantially all of the reaction chambers is between 50-55 µm. Alternatively, substantially all of the reaction chambers have a depth that is between 0.25 and 5 times the width in one dimension of the reaction chamber or, in another embodiment, between 0.3 and 1 times the width in one dimension of the reaction chamber. For the purposes of this invention, substantially all of the reaction chambers means at least 90% of the reaction chambers. In another embodiment, substantially all of the reaction chambers means at least 95%. In another embodiment, substantially all of the reaction chambers means at least 97%. In a further embodiment, substantially all of the reaction chambers means at least 99%. In another embodiment, substantially all of the reaction chambers means 100% of the reaction chambers. In one embodiment, the reaction chamber ranges in depth on a FOF from approximately one-half the diameter of an individual optical fiber up to two to three times the diameter of the fiber. The depth of a reaction chamber is measured, for example using a MicroXam 3-D interferometric surface profiler (ADE Phase shift, San Jose, Calif.). Routine reaction chamber depth measurements are made using the area difference plot feature of the instrument. The instrument compares the depth of eight chambers to a reference point on the FOF cladding to provide an average chamber depth.

The array comprises a sufficient number of reaction chambers to carry out such numerous individual assays. The array contains any number of reaction chambers. Depending on the end use of the array, substrates are made to contain a very high density (e.g., greater than 200,000), high density (e.g., at least 100,000), moderate density (e.g., at least 50,000), low density (e.g., at least 10,000), and very low density (e.g., less than 10,000) of reaction chambers. Low density arrays have a small number of reaction chambers. In one embodiment there are less than 10,000 reaction chambers. For example, the array contains between 1-96 reaction chambers. In one embodiment, the array contains between 96-384 reaction chambers. In another embodiment, the array contains between 384-1536 reaction chambers. In a further embodiment, the array contains greater than 1536 reaction chambers.

In one aspect of the invention, a FOF is made to contain a very large number of reaction chambers. In one embodiment, there are at least 10,000 reaction chambers. In another embodiment, there are at least 50,000 reaction chambers. In a further embodiment, there are greater than 100,000 reaction chambers. In another embodiment, there are greater than 200,000 reaction chambers on the surface of the substrate. Since the number of simultaneous analytical measurements is limited by the number of reaction chambers, the throughput of analytical measurement performed using an array may be increased by fabricating array substrates containing increasing densities of reaction chambers. Table 1 shows this progression for a 14×43 mm and 30×60 mm active areas, derived from 25×75 mm and 40×75 mm FOFs, respectively. See, for example, co-pending U.S. patent application Ser. No. 10/767,779, herein incorporated by reference. Pitch is the distance between fibers, measured 'center to center' (Table 1). Pitch and fiber size are generally equivalent.

TABLE 1

Development of arrays with a higher number of reaction chambers.

| Pitch (um) | Reaction Chamber Diameter (um) | # of Reaction Chambers (14 × 43 mm) | # of Reaction Chambers (30 × 60 mm) |
| --- | --- | --- | --- |
| 50 | 44 | 275K | 800K |
| 43 | 38 | 375K | 1.2M |
| 35 | 31 | 575K | 1.6M |
| 25 | 22 | 1.1M | 3.2M |

As illustrated above, one particular advantage of the present invention is that, particularly through the use of fiber optic technology, improved extremely high density arrays can be made. Thus, for example, it is possible to have as many as 50,000 different fibers and cells in a 1 $mm^2$ fiber optic bundle, with densities of greater than 250,000 individual fibers per 0.5 $cm^2$ obtainable.

For example, a wide channel reaction chamber can have dimensions of approximately 14 mm×43 mm. Thus, with this approximate dimension and at approximately $4.82 \times 10^{-4}$ chambers/$um^2$ density, the array can have approximately 290,000 reaction chambers.

Reaction chambers are formed in the surface of the substrate as is generally known in the art using a variety of techniques, including but not limited to, chemical etching, photolithography, stamping techniques, pressing, casting, molding, microetching, electrolytic deposition, chemical or physical vapor deposition employing masks or templates, electrochemical machining, laser machining or ablation, electron beam machining or ablation, and conventional machining. The technique will depend on the composition and shape of the substrate. In one embodiment, reaction chambers are formed using chemical etching. Reaction chambers are typically formed in the substrate prior to coating the array with any thin film coating.

C. The Thin Film Coatings

The present invention provides for the application of one or more thin film coatings to the array substrate. A thin film coating is a transparent or a non-transparent coating. Such transparent and non-transparent thin film coatings are designed to improve the properties and functions of the array, including to improve the compatibility of the reaction mixture or assay solution with the array substrate and to reduce problems such as optical bleed and physical interference between neighboring reaction chambers. The transparent thin film coating provides a barrier between the solution contained in the reaction chamber and the substrate and prevents both leaching of the substrate material into the solution and contact between the contents in the reaction chamber and the substrate. The non-transparent thin film coating provides a photon barrier which prevents the leaking of photons from one reaction chamber into another adjoining reaction chamber (i.e. cross-talk). The non-transparent coating creates a barrier which does not permit light to pass between neighboring reaction chambers and thus, restrains the photons and keeps the light in the reaction chamber to eliminate optical scattering. A non-transparent coating can be used to improve the retention of beads or particles in the reaction chamber (e.g., solid-support beads for carrying out a chemical reaction).

The thin film coatings of the present invention are typically applied to coat the bottom or sidewall of the reaction chambers or the top surface of the array. For the purposes of this invention, when a bottom or sidewall of the reaction chamber or the top surface of the array is coated with a thin film coating, the coating partially, substantially, or completely covers the surface of the bottom, sidewall or top surface. In one embodiment, the bottom, sidewall, or top surface is completely covered when the surface of the bottom, sidewall, or top surface is covered 100% with the thin film coating. In another embodiment, the bottom, sidewall, or top surface is substantially coated when the surface of the bottom, sidewall, or top surface is covered 97-100% with thin film coating. In another embodiment, the bottom, sidewall, or top surface is partially coated when the surface of the bottom, sidewall, or top is covered less than 97% with thin film coating. In another embodiment, the bottom, sidewall, or top surface is partially coated when at least 80% of the bottom, sidewall, or top is covered with thin film coating. In another embodiment, the bottom, sidewall, or top surface is partially coated when at least 60% of the bottom, sidewall, or top is covered with thin film coating. In another embodiment, the bottom, sidewall, or top surface is partially coated when at least 40% of the bottom, sidewall, or top is covered with thin film coating. In another embodiment, the bottom, sidewall, or top surface is partially coated when at least 20% of the bottom, sidewall, or top is covered with thin film coating. In another embodiment, the bottom, sidewall, or top surface is partially coated when at least 10% of the bottom, sidewall, or top is covered with thin film coating.

In one aspect of the invention, the non-transparent coating is deposited on at least one bottom or sidewall of substantially all of the reaction chambers or top surface of the array. In another embodiment, the non-transparent coating is deposited on at least one bottom or sidewall of substantially all of the reaction chambers or top surface of the array, and the non-transparent coating is deposited on the array prior to a transparent coating being deposited on at least one bottom or sidewall of substantially all of the reaction chambers or top surface of the array. In another embodiment, a transparent coating is deposited on at least one bottom or sidewall of substantially all of the reaction chambers or top surface of the array, and the transparent coating is deposited on the array prior to a non-transparent coating being deposited on at least one bottom or sidewall of substantially all of the reaction chambers or top surface of the array.

The Transparent Thin Film Coating

In one embodiment, the substrate of the array is coated with a non-transparent thin film coating in combination with a transparent thin film coating, which is comprised of a material typically known to be compatible with components found in assay solutions and chemical reaction mixtures. The transparent coating can be deposited on at least one bottom or sidewall of substantially all of the reaction chambers or top surface of the array prior to the non-transparent coating being deposited on at least one bottom or sidewall of substantially all of the reaction chambers or top surface of the array. Alternatively, the transparent coating can be applied after the non-transparent coating is deposited on at least one bottom or sidewall of substantially all of the reaction chambers or top surface of the array.

In one embodiment, the transparent coating is impermeable to water. In another embodiment, the transparent coating provides for a uniform surface composition. In one embodiment, the transparent coating is optically transparent. Other desirable properties of the transparent coating include durability, compatibility with the substrate materials, well-understood deposition parameters, and resistance to high temperatures. In one embodiment, the transparent coating is adhesive to glassy materials. Typically, the transparent coating minimizes non-specific absorption of macromolecules. The array substrate can be coated completely with the transparent thin film coating. In one embodiment, the entire array substrate, including of each bottom and sidewall of substantially all of the reaction chambers and top surface of the array has a transparent coating. Alternatively, the array substrate may not be coated completely with the transparent coating. For example, at least one bottom or sidewall of substantially all of the reaction chambers or top surface of the array is coated with a transparent coating (FIG. 2). Alternatively, the transparent coating is absent. In another embodiment, the bottom of substantially all of the reaction chambers of the array has a transparent coating. In another embodiment, the bottom of substantially all of the reaction chambers of the array has a transparent coating, and the sidewall of substantially all of the reaction chambers and top surface of the array do not have a transparent coating. In another embodiment, the sidewall of substantially all of the reaction chambers of the array has a transparent coating. In another embodiment, the sidewall of substantially all of the reaction chambers of the array has a transparent coating, and the bottom of substantially all of the reaction chambers of the array and top surface of the array do not have a transparent coating. In another embodiment, the sidewall of substantially all of the reaction chambers of the array and top surface of the array have a transparent coating. In a further embodiment, the sidewall of substantially all of the reaction chambers and top surface of the array have a transparent coating, and the bottom of substantially all of the reaction chambers does not have a transparent coating.

In another embodiment, at least one bottom or sidewall of substantially all of the reaction chambers or top surface of the array is partially coated. In one embodiment, the bottom and sidewall of substantially all of the reaction chambers of the array are partially coated with a transparent coating, such that the transparent coating is applied to the corner area formed at the junction between the bottom and the sidewall and is absent from the center of the bottom such that the absence to the transparent coating forms an aperture (i.e., an opening) near the center of the bottom, (e.g., see FIGS. 16a and 16b). The size of the aperture can be adjusted during the coating process such that the amount of light allowed through the bottom of the reaction chamber can be modulated and concentrated.

In one aspect of the invention, the transparent coating is applied to a feature located on a substrate. Examples of such features which may be coated on a substrate include: spherical cavities, cylinder wells, columns, posts, tilted cylinders, etc. In another embodiment, an array made of a substrate and boundary posts built on top of the substrate to form reaction chambers i.e., a "post-array" is coated with a transparent coating (FIGS. 21a-b). The size, number, and pattern of the boundary posts on the substrate can vary. The boundary posts can take any number of shapes (e.g., circular, rectangular, hexagonal, etc.). In one embodiment, a first transparent coating is applied to the post-array. In another embodiment, a second transparent coating is applied to the post-array after the first transparent coating has been applied, such that the first and second transparent coatings are different (e.g., see FIG. 21b). In another embodiment, deposition of the first and second transparent coatings onto the post-array array creates a "shadow area" wherein no coating is applied e.g., see FIG. 21b.

In another aspect of the invention, the transparent coating is applied to an array where substantially all of the reaction chambers have a sidewall that is not continuous i.e., the sidewall is interrupted with an opening between adjacent reaction chambers. The opening can be any size and shape. In one embodiment, the opening is a slit as shown in FIG. 26a. The opening in the sidewall of the reaction chamber provides a means for depositing the coating in a particular pattern on the bottom of the reaction chamber (e.g., FIG. 26b). In one embodiment, the pattern on the bottom of the reaction chamber is cone shaped. In another embodiment, the transparent coating is deposited in a gradient, such that the thickness of the coating varies. In one embodiment, the transparent coating is thicker near the center line of the bottom of the reaction chamber, and the coating becomes thinner away from the center line towards the edge.

In another aspect of the invention, the transparent coating is applied to at least one bottom or sidewall of substantially all of the reaction chambers or top surface of the array where the reaction chambers have sidewalls that are not perpendicular to the bottom of the substrate i.e., tilted reaction chambers. In one embodiment, the transparent coating is applied to a fiber optic faceplate with optical fiber strands that are not perpendicular to the bottom of the faceplate, where at least one bottom or sidewall of the reaction chambers or top surface of the fiber optic faceplate is coated with the transparent coating.

The term "transparent thin film" refers to a transparent coating with a thickness that is significantly smaller than other characteristic dimensions of the array. In one embodiment, the thickness of the transparent coating is from 0.1-5.0 microns. The thickness of the transparent coating may be non-uniform over the surface of the array, including on the inner surface of the reaction chamber. For example, in one embodiment, when present, the thickness of the transparent coating of substantially all of the reaction chambers of the array is approximately 200-400 nm on the top surface of the array. In another embodiment, when present, the thickness of the transparent coating of substantially all of the reaction chambers of the array is approximately 50-100 nm on the sidewall of the reaction chamber. In another embodiment, when present, the thickness of the transparent coating of substantially all of the reaction chambers of the array is approximately 100-300 nm on the bottom of the reaction chamber.

Many different types of materials can be used as a transparent coating. The composition of a transparent thin film coating will depend on the array substrate, the application, and the method of thin film deposition. In one embodiment, the transparent coating is a polymer. In one embodiment, the polymer is an inorganic polymer. In another embodiment, the transparent coating is a non-metal oxide (e.g. silicon dioxide ($SiO_2$)). Other transparent coatings are, for example, a metal alloy, a metal or semi-conductor oxide, nitride, carbide, or boride. Many transparent coatings are commercially available.

Transparent coating materials also include those materials used to attach an anchor primer to a substrate. Organosilane reagents, which allow for direct covalent coupling of proteins via amino, sulfhydryl or carboxyl groups, can also be used as a transparent coating to coat the array substrate. Additional transparent coatings include photoreactive linkers, e.g. photobiotin, (Amos et al., "Biomaterial Surface Modification Using Photochemical Coupling Technology," in *Encyclopedic Handbook of Biomaterials and Bioengineering, Part A: Materials*, Wise et al. (eds.), New York, Marcel Dekker, pp. 895926, 1995).

Other transparent coating materials include polymeric materials such as hydrophilic polymer gels such as polyacrylamide and polysaccharides, which are polymerized directly on the surface of the substrate or polymer chains that are covalently attached to the substrate directly (Hjerten, *J. Chromatogr.* 347,191 (1985); Novotny, *Anal. Chem.* 62,2478 (1990), as well as pluronic polymers (triblock copolymers, e.g. PPO-PEO-PPO, also known as F-108), specifically adsorbed to either polystyrene or silanized glass surfaces (Ho et al., *Langmuir* 14:3889-94, 1998), as well as passively adsorbed layers of biotin-binding proteins. The surface can also be coated with a transparent coating comprising an epoxide which allows the coupling of reagents via an amine linkage. In one embodiment, the transparent thin film coating is $SiO_2$.

Prior to applying any thin film coating, the FOF is cleaned by sonication in an aqueous, basic solution e.g., 5% Contrad® solution. Contrad® solution is a cleaning solution made up of surfactants in an alkaline basic aqueous solution. The 5% Contrad® solution contains substantially 5 percent Contrad®. Substantially 5% means that the solution may be a little more or a little less than 5% Contrad®.

In one embodiment, after cleaning, an ion-plating process is typically used to coat the etched FOFs with a transparent coating of $SiO_2$, wherein the thickness of the transparent coating is from 0.1-5.0 microns. In one embodiment, when present, the thickness of the transparent coating is 200-400 nm on the top surface of the array. In another embodiment, when present, the thickness of the transparent coating is 50-100 nm on the sidewall and when present, is 100-300 nm on the bottom of substantially all of the reaction chambers of the array. $SiO_2$ is transparent, has a very efficient water barrier thicknesses down to 10 nm, adheres to glassy materials, and withstands harsh cleaning procedures and high temperatures. Further, the surface properties of $SiO_2$ are well known, as are methods for modifying these properties. Further, $SiO_2$ has also been shown to be compatible with microscale polymerase chain reaction ("PCR") conditions.

The Non-Transparent Thin Film Coating

In another embodiment, the substrate of the array is coated with a non-transparent thin film coating made up of a material that modulates the passage of light there through e.g., blocks, substantially blocks or diffuses light to prevent, inhibit, or reduce optical bleeding of photons into adjacent reaction chambers and physical interference between neighboring reaction chambers.

The thickness of the non-transparent coating can be varied and controlled such that an opaque, semi-opaque, shiny opaque, or translucent non-transparent coating is obtained. In one embodiment, the non-transparent coating is opaque. In another embodiment, the non-transparent coating is semi-opaque. In another embodiment, the non-transparent coating is shiny opaque. In a further embodiment, the non-transparent coating is translucent. Other desirable properties of the non-transparent coating include durability, compatibility with substrate materials, well-understood deposition parameters, and resistance to high temperatures. In one embodiment, the non-transparent coating is adhesive to glassy materials. The non-transparent coating minimizes non-specific absorption of macromolecules. The array substrate can be coated in its entirety with the non-transparent thin film coating. Alternatively, the array substrate may not be coated in its entirely with the non-transparent coating. In one embodiment, at least one of the bottom or sidewall of substantially all of the reaction chambers or top surface of the array has a non-transparent coating (FIG. 2). In one embodiment, the entire array substrate, including each bottom and sidewall of substantially all of the reaction chambers and top surface of the array has a non-transparent coating. In another embodiment, the top surface of the array and the sidewall and bottom of substantially all of the reaction chambers is coated with a non-transparent coating.

In another embodiment, the bottom of substantially all of the reaction chambers of the array has a non-transparent coating. In another embodiment, the bottom of substantially all of the reaction chambers of the array has a non-transparent coating, and the sidewall of substantially all of the reaction chambers and the top surface of the array do not have a non-transparent coating. In another embodiment, the sidewall of substantially all of the reaction chambers has a non-transparent coating. In another embodiment, the sidewall of substantially all of the reaction chambers has a non-transparent coating, and the bottom of substantially all of the reaction chambers and the top surface do not have a non-transparent coating. In another embodiment, the sidewall of substantially all of the reaction chambers and the top surface of the array has a non-transparent coating. In a further embodiment, the sidewall of substantially all of the reaction chambers and the top surface of the array have a non-transparent coating, and the bottom of substantially all of the reaction chambers does not have a non-transparent coating.

In another embodiment, at least one bottom or sidewall of substantially all of the reaction chambers or top surface of the array is partially coated with a non-transparent coating. In one embodiment, the bottom and sidewall of substantially all of the reaction chambers of the array is partially coated with a non-transparent coating, such that the non-transparent coating is applied to the corner area formed at the junction between the bottom and the sidewall, and the non-transparent coating is absent from the center of the bottom such that the absence of the non-transparent coating forms an aperture (i.e., an opening) near the center of the bottom (e.g., see FIG. 16a and FIG. 16b). The size of the aperture can be adjusted such that the amount of light allowed through the bottom of the reaction chamber can be modulated and concentrated.

The non-transparent coating can be used to coat, i.e. cover, a feature located on a substrate. Examples of such features which can be coated on a substrate include: spherical cavities, cylinder wells, columns, posts, tilted cylinders, etc. In another embodiment, an array comprising a substrate with boundary posts built on top of the substrate to form reaction chambers (a "post-array") is coated with a non-transparent coating. The size, number, and pattern of the boundary posts on the substrate can vary. In one embodiment, a first non-transparent coating is applied to the post-array. In another embodiment, a second non-transparent coating is applied to the post-array after the first non-transparent coating is applied, and the first and second non-transparent coatings are different (FIG. 21b). In another embodiment, deposition of the first and second non-transparent coatings onto the post-array array creates a "shadow area" where no coating is applied e.g., see FIG. 21b In another aspect of the invention, the non-transparent coating is applied to an array where substantially all of the reaction chambers have a sidewall that is not continuous i.e., the sidewall is interrupted with an opening between adjacent reaction chambers. The opening can be any size and shape. In one embodiment, the opening is a slit as shown in FIG. 26a. The opening in the sidewall of the reaction chamber provides a means for depositing the non-transparent coating in a particular pattern on the bottom of the reaction chamber (e.g., FIG. 26b). In one embodiment, the pattern is cone shaped. In another embodiment, the non-transparent coating is deposited in a gradient such that the thickness of the coating varies where the non-transparent coating is thicker near the center line of the bottom of the reaction chamber, and the non-transparent coating becomes thinner away from the center line towards the edge.

In another aspect of the invention, the non-transparent coating is applied to at least one bottom or sidewall of the substantially all of the reaction chambers or the top surface of the array which has reaction chambers with sidewalls that are not perpendicular to the bottom of the substrate i.e., tilted reaction chambers. In one embodiment, the non-transparent coating is applied to a fiber optic faceplate with optical fiber strands that are not perpendicular to the bottom of the faceplate where at least one bottom or sidewall of substantially all of the reaction chamber or the top surface of the fiber optic faceplate is coated with the non-transparent coating.

Figure 14:
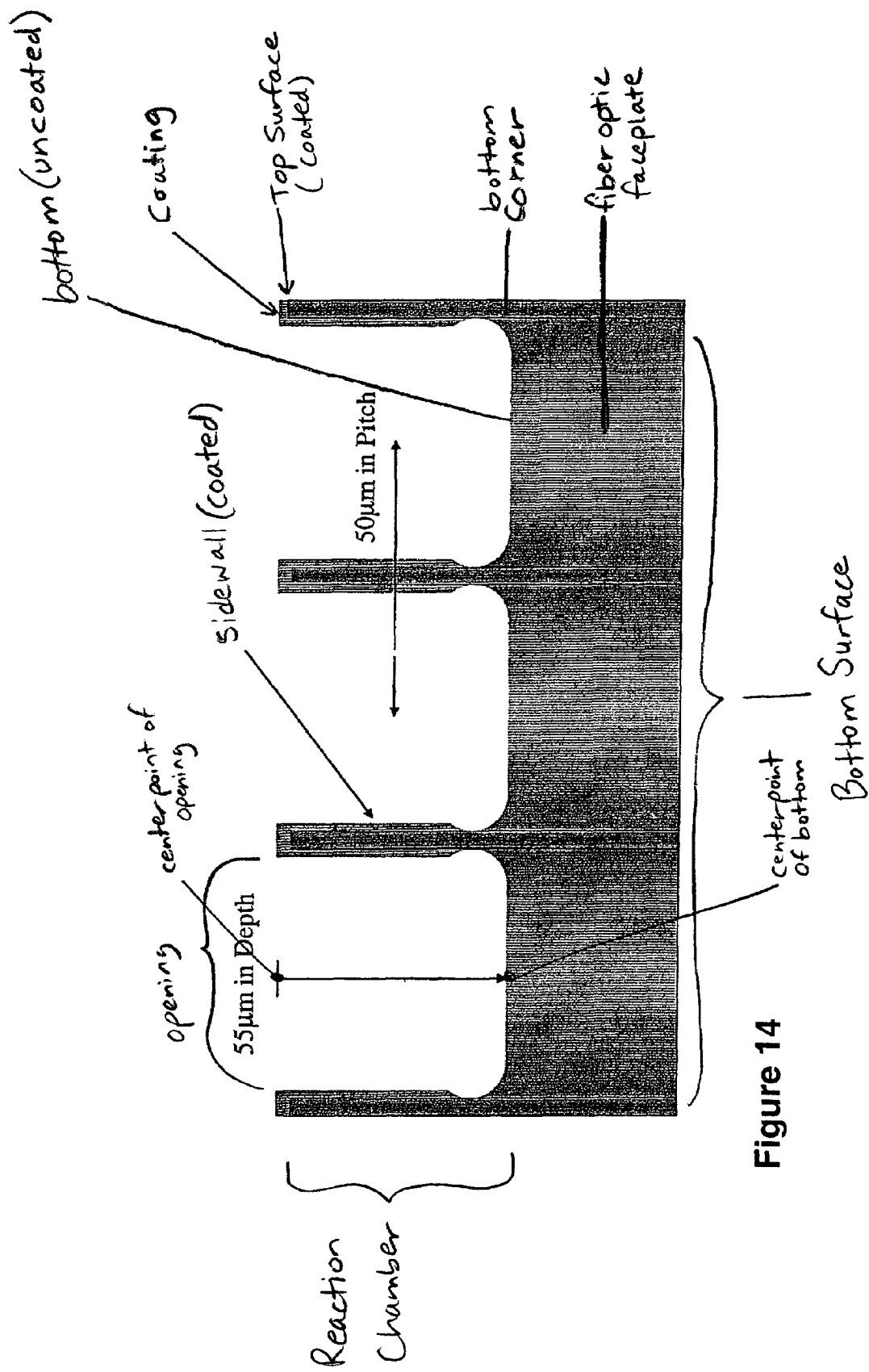
FIG. 14 is a side view of a fiber optic faceplate containing reaction chambers in which the sidewall of the reaction chambers and top surface of the array are coated with a non-transparent thin film.

The term "non-transparent thin film" refers to a non-transparent coating with a thickness that is significantly smaller than other characteristic dimensions of the array (FIG. 14). In one embodiment, the thickness of the non-transparent coating determines whether the coating is opaque, semi-opaque, translucent, or shiny opaque.

Many different types of materials can be used as non-transparent thin film coatings. The composition of the non-transparent thin film coating will depend on the array substrate, the application, and the method of thin film deposition. A non-transparent thin film coating can be selected from an organic compound, an inorganic compound, and a non-metal oxide. In one embodiment, the non-transparent coating is a polymer. In another embodiment, the non-transparent coating is an organic or inorganic compound. In one embodiment, the inorganic compound is a metal. Metals that are used as non-transparent thin film coatings are selected from chromium, gold, silver, aluminum, titanium, copper, iron, nickel, zinc, cadmium, tin, lead, antimony, cobalt, platinum, and any alloys thereof, e.g., titanium/lead. In one embodiment, the non-transparent coating is selected from chromium, gold, silver, aluminum, titanium, and platinum. In one embodiment, the non-transparent coating is chromium. In another embodiment, the non-transparent coating is silver.

In one embodiment, a first non-transparent coating is applied to the array, and a second non-transparent coating is applied to the array after the first non-transparent coating is applied. In one embodiment, the first and second non-transparent coatings are the same. Alternatively, the first and second non-transparent coatings are different. In one embodiment, the first non-transparent coating is chromium, and the second non-transparent coating is gold. In another embodiment, the first non-transparent coating is gold and the second non-transparent coating is chromium. In another embodiment, the first non-transparent coating is titanium and the second non-transparent coating is platinum. In another embodiment, the first non-transparent coating is platinum and the second non-transparent coating is titanium. The first and second non-transparent coatings can be applied in separate processes. Alternatively, the first and second metal coatings can be applied in the same process by switching to different metal targets.

In another embodiment, the coating is dielectric. The dielectric coating can be non-transparent or transparent. In one embodiment, the dielectric coating is non-transparent. In another embodiment, the dielectric coating is transparent. A coating which is dielectric has a high electrical resistance, for example, $SiO_2$. In one embodiment, a transparent, dielectric coating is applied on top of a non-transparent coating and is used to protect the non-transparent coating from erosion. For example, a $SiO_2$ coating is applied after a metal coating is applied to an array, in order to protect the metal coating from erosion while the $SiO_2$ coating remains transparent.

In other embodiment, the coating is conductive. A coating which is conductive is electrically conductive, for example, a gold thin film. A conductive coating can be used as a first coating for electroplating or used as an electrode surface in a solution. In one embodiment, a non-transparent coating which is conductive is applied to at least one bottom or sidewall of substantially all of the reaction chambers or top surface of the array. In another embodiment, a non-transparent coating, which is conductive, is applied to at least one bottom or sidewall of substantially all of the reaction chambers or top surface of the array and a transparent coating is applied to at least one bottom or sidewall of substantially all of the reaction chambers or top surface of the array after the non-transparent coating is applied. In one embodiment, the array is coated with a conductive coating which allows for the chemical reactions or bioassays carried out in the reaction chambers to be electrochemically enhanced. For example, a metal coated, etched FOF can be used as an anode or a cathode for analysis using electrochemical methods in conjunction with illuminochemistry. In another embodiment, a $SiO_2$ coating is applied on top of a conductive metal coating and the $SiO_2$ coating of the array is polarized which enhances the movement of ions near the surface in solution. Many non-transparent coatings are commercially available.

In another aspect of the invention, the array substrate is coated with both a transparent and non-transparent coating. In one embodiment, the sidewall of substantially all of the reaction chambers and top surface of the array are coated with the transparent coating, and the bottom is coated with the non-transparent coating. In another embodiment, the sidewall and bottom of substantially all of the reaction chambers are coated with the transparent coating, and the top surface of the array is coated with the non-transparent coating. In another embodiment, the bottom of substantially all of the reaction chambers and the top surface of the array are coated with the transparent coating, and the sidewall of substantially all of the reaction chambers is coated with the non-transparent coating. In another embodiment, the bottom of substantially all of the reaction chambers is coated with the transparent coating, and the sidewall of substantially all of the reaction chambers and top surface of the array are coated with the non-transparent coating. In another embodiment, the top surface of the array is coated with the transparent coating, and the sidewall and bottom of substantially all of the reaction chambers are coated with the non-transparent coating. In another embodiment, the sidewall of substantially all of the reaction chambers is coated with the transparent coating, and the bottom of substantially all of the reaction chambers and the top surface of the array are coated with the non-transparent coating. In another embodiment, the bottom of substantially all of the reaction chambers is coated with the transparent coating, the sidewall of substantially all of the reaction chambers is coated with the non-transparent coating, and the top surface of the array is not coated.

Multiple layers of transparent and non-transparent coatings can be deposited on the array substrate. In one embodiment, the transparent coating includes at least a first transparent coating. In another embodiment, the non-transparent coating includes at least a first non-transparent coating. Two or more coatings of transparent and/or non-transparent coatings can be deposited on at least one bottom or sidewall of substantially all of the reaction chambers or top surface of the array. In one embodiment, the first non-transparent coating, e.g., chromium, is deposited on one side of the sidewall of substantially all of the reaction chambers of the array, and the second non-transparent coating, e.g., gold, is deposited on the opposite side of the sidewall of substantially all of the reaction chambers of the array. In another embodiment, at least one of the bottom or sidewall of substantially all of the reaction chambers or top surface of the array is coated with the first and second non-transparent coating. In one embodiment, the bottom of substantially all of the reaction chambers of the array is coated with a first transparent coating, and the bottom and sidewall of substantially all of the reaction chambers of the array are coated with a partial transparent second coating, further wherein the second transparent coating is applied to the corner area formed at the junction between the bottom and sidewall of the reaction chamber, and the second transparent coating is absent from the center of the bottom such that the absence of the second transparent coating on the bottom of the reaction chamber forms an aperture near the center of the bottom. In one embodiment, the bottom and sidewall of substantially all of the reaction chambers of the array are coated with a partial non-transparent coating, further wherein the transparent coating is applied to the corner area formed at the junction between the bottom and sidewall of the reaction chamber, and the non-transparent coating is absent from the center of the bottom such that the absence of the non-transparent coating on the bottom of the reaction chamber forms an aperture near the center of the bottom.

Functionalization of the Transparent and Non-transparent Thin Film Coatings

Both the transparent and non-transparent thin film coatings allow for easy attachment of reactants (e.g. proteins, enzymes, and nucleic acids) and do not negatively affect the activity of immobilized reactants. In some instances, the thin film coating can increase the stability of reactants.

Transparent and non-transparent coatings allow for surface modification which can provide additional functions to enhance chemical reactions or to eliminate unwanted effects such as cross-talk between adjacent reaction chambers.

Generally, the reactants and analytes are non-covalently associated in the reaction chambers. However, thin film coated chambers can be biologically or chemically functionalized. For example, any of the transparent or non-transparent thin film coatings discussed can be derivatized with one or more functional groups, commonly known in the art for the immobilization of enzymes and nucleotides, e.g. metal chelating groups (e.g. nitrilo, triacetic acid, iminodiacetic acid, pentadentate chelator, etc.). In one embodiment, substantially all of the reaction chambers of the thin film coated array, coated with either a transparent or non-transparent coating, are modified to contain functional groups that are used to attach or capture, either covalently or non-covalently, reactants or analytes to the sidewall or bottom. "Chemically modified reaction chambers" in this context include, but are not limited to, the addition of functional groups including amino groups, carboxy groups, oxo groups and thiol groups, that are attached to the reaction chamber thin film coated surface and used to attach or capture reactants or analytes on the same surface. Alternatively, "biologically modified reaction chambers" include the attachment of binding ligands or binding partner pairs, including but not limited to, antigen/antibody pairs, enzyme/substrate or inhibitor pairs, receptor-ligand pairs, carbohydrates and their binding partners (lectins, etc.).

In one embodiment, the transparent coating generates a surface for chemical or biological modification. In another embodiment, the non-transparent coating generates a surface for chemical or biological modification. In a further embodiment, the transparent coating provides a surface for enzyme immobilization. In one embodiment, the enzyme for immobilization is selected from sulfurylase, luciferase, polymerase, hypoxanthine, phosphoribosyltransferase, xanthine oxidase, uricase, apyrase, and peroxidase. In another embodiment, the non-transparent coating provides a surface for enzyme immobilization. In another embodiment, the first coating provides a means for trapping reactants or analytes in the reaction chamber. In another embodiment, the non-transparent coating provides a means for trapping reactants or analytes in the reaction chamber.

2. Process for Single Sided Chemical Etching of a Fiber Optic Faceplate

The present invention is further directed to a process for producing reaction chambers on an array substrate and an apparatus for performing such a process. In one embodiment, reaction chambers are formed on a FOF substrate. In one embodiment, reaction chambers are formed using a selective chemical etching process which takes advantage of the difference in etch rates between core and cladding materials. See, e.g., Pantano, et al., *Chem. Mater.* 8:2832 (1996), and Walt, et al., U.S. Patent Publication No. 20020015146. Reaction chambers may be formed on one or both sides of a FOF. Methods for forming reaction chambers on both sides of the substrate require no special hardware or an apparatus beyond an etching bath. However, in one embodiment, the reaction chambers etched on one of the side of the FOF subsequently need to be removed so that the surface will be smooth enough for optical coupling to a camera system. This removal process involves an expensive and time-consuming polishing step. If reaction chambers are formed only on a single side, the FOF is almost immediately ready for cleaning and surface coating. The present invention provides a both an apparatus and a chemical etching process which are designed to produce reaction chambers on only one side of a FOF.

A. Etch Apparatus: Clamps and Gasket

Figure 12:
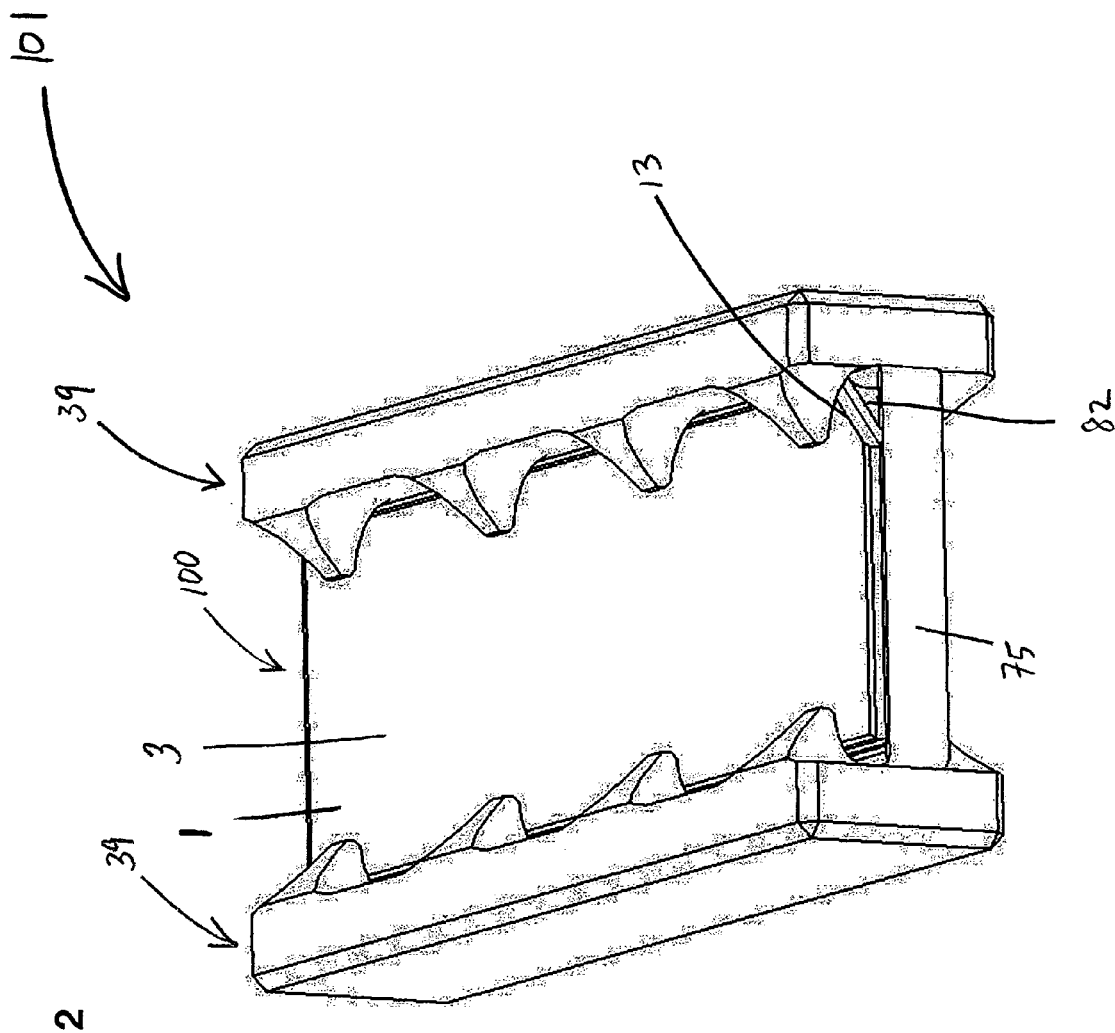
FIG. 12 is a drawing of an assembled fiber optic faceplate "clamped sandwich" held together with two clamps and ready for the etch process (top view)
Figure 13:
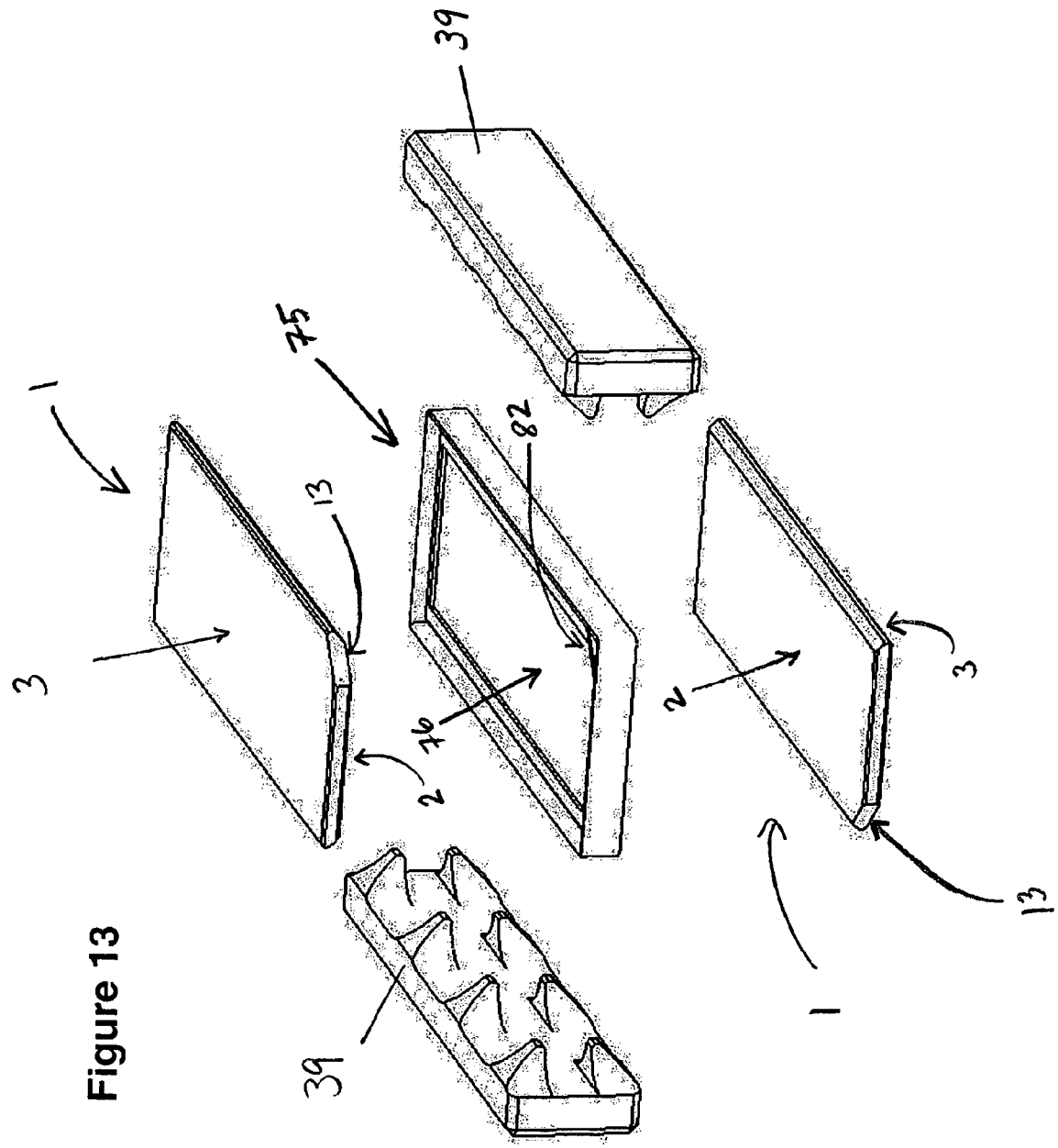
FIG. 13 is an exploded view drawing of a fiber optic faceplate "clamped sandwich".

Generally, an apparatus used to etch a FOF on a single side includes the following pieces of hardware: at least one clamp and a gasket (FIGS. 12 and 13). The term "sandwich" refers to two FOFs with a gasket positioned in between the two FOFs. A clamp 39 is a device which is used to press or hold firmly the two FOFs 1 together with a gasket 75 to form a "clamped sandwich" which is used during the etch process. A gasket 75 is designed to create a fluid tight seal in a clamped sandwich, e.g., a gasket is placed in between two FOFs in order to protect one side of each FOF from exposure to acid. Both the FOFs and gasket each contain an index feature which provides a physical basis for mounting the FOFs so that only one side of each FOF is subjected to acid treatment.

1. Clamp

The present invention comprises a clamp which includes two joined components, a base and prongs. Both components are constructed from a single suitable material, or alternatively, each component is constructed separately from suitable materials and mated together using any variety of mating techniques known in the art (e.g., adhesively attached, mechanically mated etc.). A base is generally the shape of a rectangular box having at least a top surface and a bottom surface which are opposed, wherein there is a distance between the top and bottom surface. A bottom surface is permanently joined to a top surface by sides and ends which are permanently joined to form the outer perimeter of the base. A base has at least a first and second side and at least a first and second end. A surface of a base is generally planar.

At least two prongs are aligned on a surface of a base. In this version of the invention, at least two prongs are aligned on a top surface of a base and extend radially outward a distance. Any number of prongs are aligned on a top surface. A suitable prong is any shape or size. For example, a prong is a tapered rectangle having at least four edges, including an external and internal edge and a first and second edge. External and internal edges are opposed and first and second edges are opposed. The edges of a prong are connected to form a tapered rectangular shaped prong. An internal edge of a prong is flat and attaches perpendicularly to a top surface of a base. A prong has a top and a height. A pair of prongs is positioned along a top surface, with the internal edge of one prong opposed to the internal edge of a second prong to form a slot down the middle of the top surface of a base. A slot with a width $W_{11}$ is where FOFs and a gasket are securely held by the prongs of a clamp. It is understood by those in the art that a clamp is not limited to a specific shape and includes other shapes and overall dimensions.

Referring to FIGS. 7a-d, one embodiment of the invention includes a unitary clamp 39 comprised of a rectangular shaped base 40 and at least two prongs 43, 44. A base has a top surface 41 and a bottom surface 42, which are opposed. A bottom surface 42 is permanently joined to a top surface 41 by any number of sides and ends, which are connected to form the outer boundary of a base 40. The distance $D_2$ extending between the top surface 41 and the bottom surface 42 is any distance. In one embodiment, the distance between the top and bottom surfaces 41, 42 is no greater than 10 cm. In another embodiment, $D_2$ is 0.5 mm to 5 mm. In a further embodiment, the distance D2 is about 4 mm.

In one embodiment, a rectangular base 40 has a first side 35 and a second side 36 separated by a distance $W_{12}$ and a first end 37 and a second end 38 separated by a distance $L_{10}$. In a more preferred embodiment, a base 40 is rectangular shaped with flattened corners. For example, a base 40 has a first side 35 and a second side 36 separated by a distance $W_{12}$; a first end 37 and a second end 38 separated by a distance $L_{10}$; and four corner ends, including a first corner end 45, a second corner end 46, a third corner end 47, and a fourth corner end 48.

Those of ordinary skill in the art will appreciate that the sides, ends, and corner ends of a base 40 are any length. In one embodiment, the first and second sides 35, 36 are the same length; the first and second ends 37, 38 are the same length; and the four corner ends 45, 46, 47, 48 are the same length. In one embodiment, the length and width are the same. In another embodiment, the sides are longer in length than the ends. For example, the first side 35 and second side 36 each have a length $L_9$ of about 58 mm. The first end 37 and second end 38 each have a length $L_{11}$ that is about 12 mm. The four corner ends, including 45, 46, 47, and 48 each have a width $L_{13}$ that is about 2 mm.

A prong is any shape and has any dimensions, including height. In this version of the invention, the general shape of the prong is a tapered rectangle. A prong comprises multiple edges, a prong top and a height. In one embodiment, a prong 43 has four edges, including an internal edge 49 and an external edge 52 which are opposed, and a first edge 50 and a second edge 51 which are opposed. In one embodiment, the surface of an inner edge 49 is flat and perpendicular to the top surface 41. The surface of the external edge 52 is flat and forms an angle $A_4$ with the top surface 41. In one embodiment, the angle $A_4$ is 45 degrees. A first edge 50 has a surface that is concave and a second edge 51 has a surface that is concave. A prong top may be any shape and have any dimensions. In one embodiment, a prong top 55 is pointed. Alternatively, a prong top is rounded or flat. In one aspect of the invention, the prong top 55 is flat and rectangular shaped. In a further embodiment, the rectangular area of the prong top 55 is about 1 mm×2 mm. A prong (e.g., 44) may be any height. In one embodiment, the height $H_6$ of a prong is about 5-6 mm.

In one invention, a clamp 39 uses a set of at least two prongs to compress FOFs and a gasket together for the etching process. The surface of a base 40 has any number of prongs. Generally, prongs are aligned along the top surface 41. In one embodiment, a prong 43 is aligned on a top surface 41 with its external side 52 along a first side 35 and another prong 44 is opposed and aligned on a top surface 41 with its external side along a second side 36. A clamp 39 may have one or more pairs of prongs. In one invention, a clamp 39 has multiple pairs of prongs. In one aspect of the invention, a clamp 39 has one to six pairs of prongs aligned on its top surface 41. It is understood by one skilled in the art that the number of pairs of prongs can vary depending on the size of the FOF.

A pair of at least two prongs 43, 44 and base 40 form a unitary clamp 39 comprised from a single suitable material or from separate suitable materials which are integrally formed or mated together. In this version, the clamp 39 has a slot 56 located down the center of the top surface 41. The slot 56 is where the FOFs and gasket are held by the clamp 39. The slot 56 is created by the alignment of the prongs 43 and 44 on the top surface 41 along the first and second sides 35, 36. The length $L_{10}$ of slot 56 extends from the first end 37 to the second end 38. The width $W_{11}$ of slot 56 is the distance between the internal edges of a prong 44 and the internal edge of a prong 43. The slot can have any width and any length. The width $W_{11}$ of a slot 56 is generally equivalent to the width of two FOFs and a gasket sandwiched together. In one embodiment, the width $W_{11}$ of the slot is about 6 mm. In one embodiment, the length $L_{10}$ of the slot 56 is about 62 mm.

A clamp is comprised of any suitable material. In one embodiment, a clamp is fabricated from any acid resistant material. In a further embodiment, the clamp is fabricated from a plastic material. In a most preferred embodiment, the clamp is fabricated poly ether ether ketone ("PEEK clamp").

2. Gasket

The present invention includes a gasket as one of the pieces of hardware comprising an etch apparatus. The general purpose of a gasket is to form a seal between the gasket and one FOF surface in order to protect the other surface of the FOF from exposure to liquid (e.g., acid). A gasket is fabricated from a suitable material with properties compatible with the conditions of the chemical etching process. A gasket is generally comprised of an acid resistant material. In one embodiment, a material comprising a gasket is flexible. Those of ordinary skill in the art will appreciate that a gasket is any shape or size which is suitably shaped to form a seal with the FOF, such that the sealed area is correctly located on the FOF and protects the desired area from etching. A gasket has at least two surfaces e.g., a top and bottom surface. A gasket surface has a ridge, which is a flat, raised surface that makes contact with the FOF along the perimeter of the FOF around the area to be protected from the etching process. In one embodiment, a gasket has at least two opposed ridges which are flat raised surfaces that make contact with the FOF along the perimeter of the FOF around the area to be protected. In one embodiment, a gasket is rectangular in shape having two flat opposed surfaces with a distance in between the surfaces and each surface contains a ridge. The gasket has a protruding outer frame feature on both its top and bottom surface that serves to position the FOF in the proper location when it is mounted on the gasket. The outer frame of the gasket is comprised of walls which are permanently joined to the top and bottom surface. A gasket has any number of walls. In one embodiment, a gasket has four walls, including a first wall, a second wall, a third wall and a fourth wall. A gasket wall has a height. The gasket walls are connected at perpendicular angles to form a rectangular outer frame. The gasket walls, which comprise the outer frame of the FOF, extend above the top surface and below the bottom surface to form a tray-like structure into which each FOF is placed during the etch process. In one aspect of the invention, a gasket is the same general shape as a FOF.

At least the top surface or the bottom surface or alternatively, both surfaces of a gasket include a raised portion which forms a ridge elevated above the surface, wherein the reason for such a ridge is to facilitate the formation of a tight seal between a FOF and the gasket surface and prevent one side of each FOF from exposure to liquid. The ridge is smooth and uniform in cross section and forms a continuous barrier around the perimeter of the FOFs. In one embodiment, a ridge is a rectangular shaped border which has a height above the gasket surface and a width. A ridge is located a distance inside the gasket walls.

A gasket further includes at least one index feature to provide a physical basis for properly orienting a FOF during the etch process, so that a FOF is only allowed to be mounted in a gasket in only one orientation. Proper positioning of a FOF ensures consistency that the same side of the FOF is etched. An index feature is any shape or form. In one embodiment, a band is positioned at an angle in one corner of a gasket to form a gasket index feature, wherein the band forms a corner barrier which restricts how a FOF is mounted into a gasket (i.e. the corner notch of a FOF must be matched to the gasket index feature).

Referring to FIGS. 11a-e, this version of the invention includes a gasket 75, including a top surface 76 and a bottom surface 77. The top and bottom surfaces 76, 77 are directly opposed, wherein there is a distance between the top surface 76 and the bottom surface 77. The distance between the two surfaces is any distance. In one embodiment, the distance $H_{10}$ between the top surface 76 and the bottom surface 77 is about 1 mm. A surface of a gasket is any shape. In one embodiment, the top and bottom surfaces of a gasket are the same. In preferred embodiment, the top and bottom surfaces of a gasket are rectangular in shape.

It is understood by one skilled in the art that a gasket has any number of walls. In one embodiment, a gasket 75 has four walls, including a first wall 78, a second wall 79, a third wall 80, and a fourth wall 81. In one embodiment, all of the walls of a gasket 75 are connected permanently. The walls are connected to form an outer frame permanently joined to opposed top and bottom surfaces 76, 77. In one embodiment, the walls 78, 79, 80, 81 of a gasket form a rectangular shaped frame around opposed top and bottom surfaces 76, 77. For example, in FIG. 11a, a first wall 78 and third wall 80 extend perpendicular between a second wall 79 and fourth wall 81.

The walls of a gasket 75 have a length which is any length. In one embodiment, the walls 78, 79, 80, 81 are the same length or alternatively different lengths. Suitable gaskets have walls that are different lengths. In one embodiment, the length $L_4$ of first wall 78 is about 78 mm and the length of a third wall 80 is the same as length $L_4$ of the first wall 78. The width $L_6$ of a second wall 79 is about 42 mm and the length of a fourth wall 81 is the same as the length $L_6$ of a second wall 79.

In one embodiment, one or more walls of a gasket 75 extend to a height above the top surface 76. In one embodiment, all of the walls 78, 79, 80, 81 extend to a height above and below the surfaces 76, 77. In a more preferred embodiment, a fourth wall 81 extends above the top surface 76 to a height $H_8$; a second wall 79 extends above the top surface 76 to a height $H_{12}$; a third wall 80 extends above the top surface 76 to a height $H_{14}$; and a first wall 78 extends above the top surface 76 to a height $H_{17}$. In a more preferred embodiment, the heights of each of the sides above the top surface $H_8$, $H_{12}$, $H_{14}$, and $H_{17}$ are the same. In a most preferred embodiment, the height $H_8$, $H_{12}$, $H_{14}$, and $H_{17}$ of each of the walls 81, 79, 80, 78 which extends above the top surface 76 is the same and about 2 mm.

In another embodiment, one or more walls of a gasket 75 have a height that extends below the bottom surface 77. In one embodiment, a fourth wall 81 extends below the bottom surface 77 to a height $H_9$; a second wall 79 extends below the bottom surface 77 to a height $H_{13}$; a third wall 80 extends below the bottom surface 76 to a height $H_{15}$; and a first wall 78 extends below the bottom surface 77 to a height $H_{16}$. In a more preferred embodiment, the height $H_9$, $H_{13}$, $H_{15}$, and $H_{16}$ of each of the walls 81, 79, 80, 78 which extends below the bottom surface 77 is the same and about 2 mm.

Both surfaces 76 and 77 of a gasket contain a raised portion which is a ridge elevated above the surface. In one embodiment, both the top surface 76 and bottom surface 77 include a raised ridge. For example, a suitable ridge 85 is raised a height $H_7$ on a top surface 76 and a same ridge is found on a bottom surface 77. In one embodiment, the height $H_7$ of a ridge 85 is about 0.5 mm. A ridge 85 is continuous and the shape of a rectangle. A ridge 85 forms a border inside the walls of a gasket and is a distance $D_3$ from the walls of the gasket. In one embodiment, the distance $D_3$ of a ridge 85 from the wall of a gasket is about 1 mm. A ridge 85 has any width. In one embodiment, the width $W_{15}$ of a ridge is about 2 mm. In some suitable gaskets, there is at least one additional feature of the ridge which ensures that an effective seal is formed near the index feature between a FOF and the gasket. For example, a ridge 85 has an additional crossbar 84. Crossbar 84 has the same height and width as the rest of the ridge 85. A gasket has any number of cross bars.

In this invention, a gasket has at least one index features. An index feature of a gasket provides a physical basis for orienting a FOF so that the FOF mounts into a gasket in only one orientation. Consistent orientation of a FOF in a gasket ensures that the same single side of a FOF is protected from exposure to liquid. An index feature is located on the top surface 76 or the bottom surface 77 or alternatively, on both surfaces 76, 77 of a gasket. In one embodiment, a gasket includes at least one index feature which is a corner barrier 82, comprising a band 83 placed at an angle $A_5$ that provides a physical basis for orienting a FOF when the FOF is mounted into a gasket. In one embodiment, the angle $A_5$ is 45 degrees. As a result of having a suitable index feature on a FOF (e.g., a corner notch) and a complementary index feature on a gasket (e.g., a corner barrier), proper mounting of a FOF 1 into a gasket occurs when the notched corner 13 of a FOF and a corner barrier 82 of a gasket are appropriately aligned. When a FOF and gasket are properly assembled, the polished surface 2 of a FOF 1 is consistently placed against a gasket 75 and therefore, the polished surface 2 is not exposed to acid and does not get etched.

A gasket is fabricated from a suitable material wherein the material is compatible with the conditions of the etch process. In one embodiment, a gasket is fabricated from an acid resistant material. Suitable materials for fabrication of a gasket are flexible. In one embodiment, the gasket is constructed of a flexible material. In one embodiment, the gasket is comprised of silicone.

B. Chemical Etch Process

Figure 10:
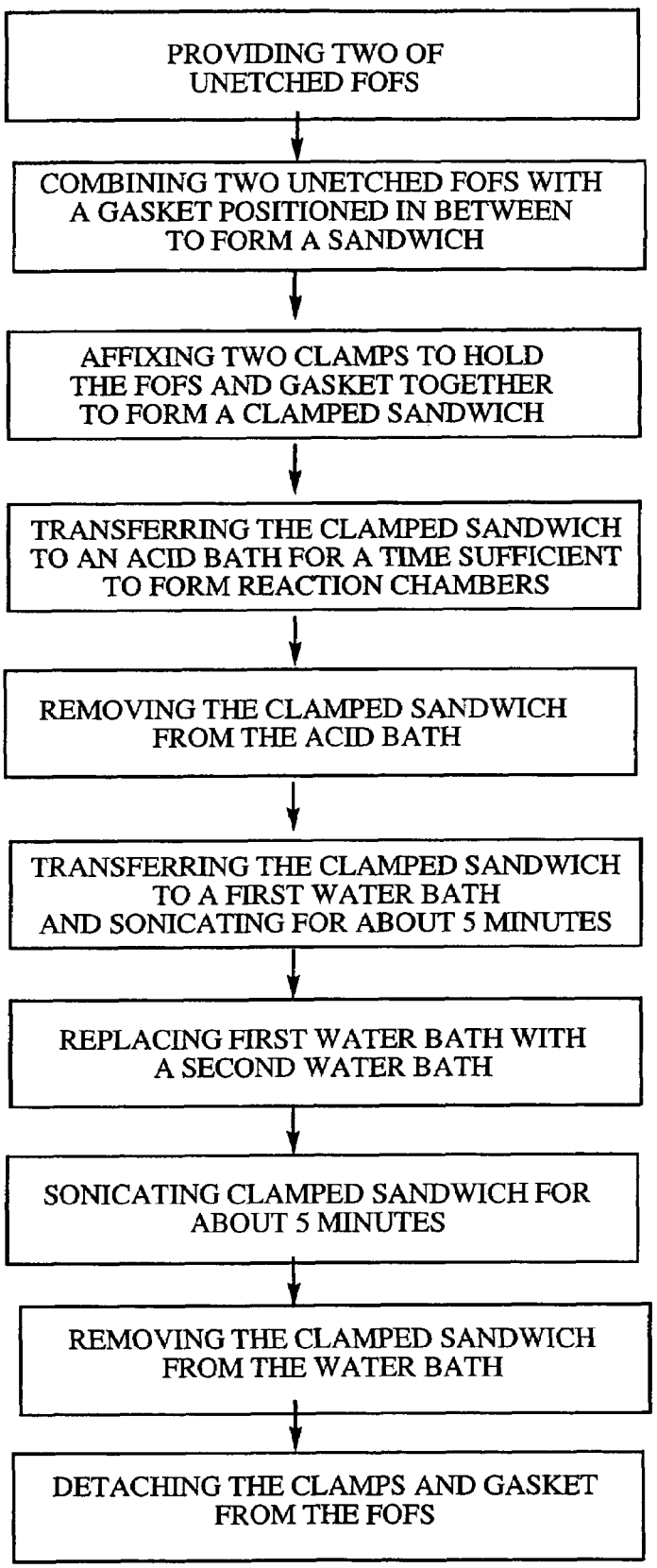
FIG. 10 is a process flow diagram illustrating the single-sided etching process.

The present invention provides a process that produces reaction chambers onto a single surface or side of a FOF. One suitable process is chemical etching, wherein the reaction chambers are etched onto a FOF using chemicals. In one embodiment, acid is the chemical used to etch the reaction chambers onto the FOF. In a further embodiment, a process for etching a single surface of a FOF requires that one surface of the FOF is protected such that the protected surface is not exposed to chemicals and therefore, does not get etched. A suitable process for etching a single surface of a FOF uses an apparatus (e.g., the apparatus described above, comprised of a set of clamps and a gasket) to protect one surface of a FOF from chemical exposure. In one embodiment, a FOF with reaction chambers etched onto one surface is produced using the process outlined in FIG. 10. Prior to chemical exposure, unetched FOFs are assembled using an etch apparatus comprised of a set of clamps and a gasket.

FIG. 13 shows an exploded view which illustrates the relationship of the various components utilized in the etching process, including a gasket 75 which is placed in between two unetched FOFs 1. A first surface 2 of a FOF 1 is mounted opposed to a top surface 76 of a gasket 75, wherein the corner notch 13 of the FOF 1 is matched with the complementary corner barrier 82 on the gasket 75. Two PEEK clamps 39 are affixed along the two longer, opposite sides of the sandwich 100 to firmly hold the FOFs 1 and gasket 75 together and to prevent the first surface 2 of the FOF from being exposed to acid. The entire assembly shown in FIG. 12 is referred to as a "clamped sandwich". The clamped sandwich 101 is transferred to an acid bath. In one embodiment, the acid bath is comprised of 20% nitric acid (w/v aqueous solution). The time and conditions of the chemical etching reaction are adjusted to achieve control of the size and volume of the resultant reaction chambers. The clamped sandwich remains in the acid bath for a time sufficient to allow reaction chambers of the desired depth to form. In one embodiment, the etch time is about 3 hours and 30 minutes, to produce reaction chambers with a reaction chamber depth of 55 µm. The process of fabricating reaction chambers is adapted to any fiber size so as to provide a wide range of appropriately sized chambers. Generally, chambers are introduced into the termini of the fibers by placing the FOF into an acid bath for a variable amount of time. The amount of time is varied, depending upon the overall depth of the reaction chamber desired (see e.g., Walt, et al., 1996. *Anal. Chem.* 70: 1888).

3. Process for RER Cleaning

Figure 9:
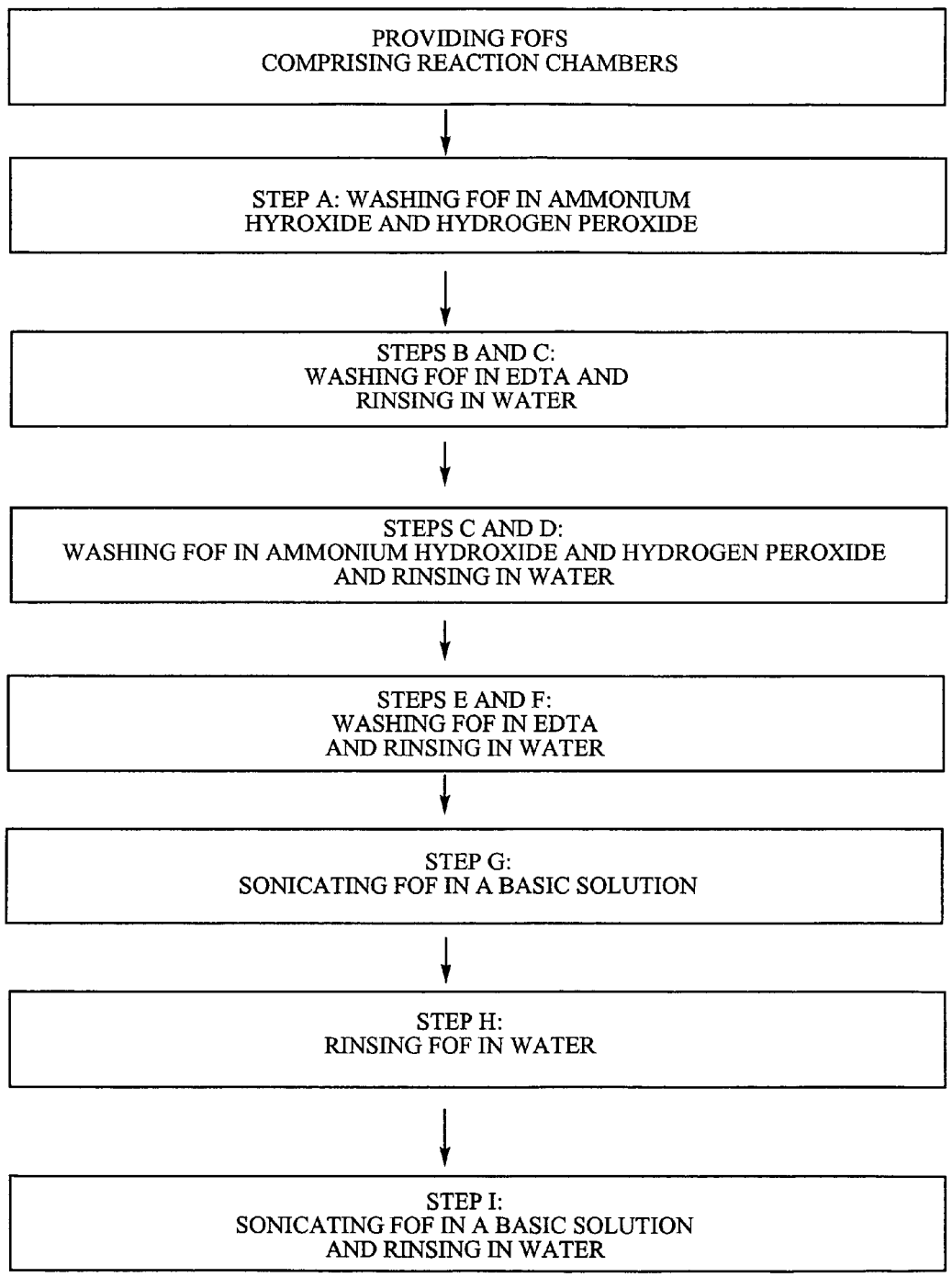
FIG. 9 is a process flow diagram illustrating the RER cleaning procedure.

Prior to applying one or more thin film coatings, all substrates (e.g., etched FOFs) are thoroughly washed to make the array surface free of gross particulate contaminants, and relatively free of oily contamination, such as fingerprints, prior to applying the thin film coating. In one embodiment, the FOF is thoroughly cleaned after the process etching of forming the reaction chambers is complete as described in Example 1 (FIG. 9). In one embodiment, after cleaning at least one of the bottom, top, or sidewall of substantially all of the reaction chambers, is coated with a transparent thin film coating where the transparent thin film coating comprises $SiO_2$ which is 0.1-5.0 microns thick, optically transparent, and impermeable to water and the transparent coating is applied prior to apply the non-transparent coating. In another embodiment, at least one of the bottom, top, or sidewall of substantially all of the reaction chambers is coated with a non-transparent thin film coating where the non-transparent coating is chromium or silver.

4. Process for Coating Arrays

Several methods are used for depositing one or more thin film coatings onto the surface of an array substrate. These methods include vapor and liquid deposition processes such as thermal evaporation, e-beam evaporation, sputtering, spray, and electrostatic plating and can be used to deposit both transparent and non-transparent thin film coatings. Typically, the transparent and non-transparent coatings are applied in separate steps. These methods are described in further detail below.

A. Vapor Deposition

Vapor deposition is a method widely used in the semiconductor and optical components industry for which controlled processes are commercially available. Vapor deposition can be used to deposit the transparent and non-transparent coating. In one embodiment, when present, the transparent and/or non-transparent thin film coatings are deposited from the vapor phase onto at least one bottom or sidewall of substantially all of the reaction chambers or top surface of the array. Vapor phase deposition processes are typically described as either physical or chemical in nature, depending on the extent to which the deposited film material is chemically transformed from its precursors. In one embodiment, when present, the transparent and/or non-transparent thin film coatings are deposited onto at least one bottom or sidewall of substantially all of the reaction chambers or top surface of the array using a physical vapor deposition process known as sputtering or evaporation, where the chemical reagent, which is the precursor to the thin film, is thermally evaporated in a vacuum chamber. The "pre-film" vapor coats at least one bottom or sidewall of substantially all of the reaction chambers or top surface of the array and forms the thin film coating. See e.g., Plummer et al., Silicon VLSI Technology, Chapter 9, Prentice Hall, 2000. In one embodiment, a non-metal oxide is deposited onto at least one bottom or sidewall of substantially all of the reaction chambers or top surface of the array using the sputtering or evaporation method of vapor deposition. In a further embodiment, the non-metal oxide $SiO_2$ is deposited onto at least one bottom or sidewall of substantially all of the reaction chambers or top surface of the array using the sputtering or evaporation method (FIGS. 1a, 1b, and 2b). In another embodiment, a metal is deposited onto at least one bottom or sidewall of substantially all of the reaction chambers or top surface of the array using the sputtering or evaporation method of vapor deposition. In a further embodiment, the metal chromium is deposited onto at least one bottom or sidewall of substantially all of the reaction chambers or top surface of the array using the sputtering or evaporation method of vapor deposition. In another embodiment, the metal silver is deposited onto at least one bottom or sidewall of substantially all of the reaction chambers or top surface of the array using the sputtering or evaporation method of vapor deposition.

Chemical vapor deposition can be used to deposit the transparent and/or non-transparent coating. In one embodiment, when present, the transparent and/or non-transparent thin film coatings are deposited onto at least one bottom or sidewall of substantially all of the reaction chambers or top surface of the array using a chemical vapor deposition process known as plasma-enhanced chemical vapor deposition (PECVD), where two chemicals are reacted unto a heated substrate to produce a thin film coating. PECVD is performed in a reaction chamber and gases are injected into the chamber. A chemical reaction occurs at typically 400 degrees C. which results in a thin film coating being deposited onto the array. A plasma is generated in the chamber to increase the energy available for the chemical reaction at a given temperature. The PECVD process is typically performed on one side of the substrate at a time. See e.g., Plummer et al., Silicon VLSI Technology, Chapter 9, Prentice Hall, 2000. In another embodiment, a non-metal oxide is deposited onto at least one bottom or sidewall of substantially all of the reaction chambers or top surface of the array using the PECVD method of vapor deposition. In one embodiment, the non-metal oxide $SiO_2$ is deposited onto at least one bottom or sidewall of substantially all of the reaction chambers or top surface of the array using the PECVD method (FIGS. 1c, 1d, and 2c). In another embodiment, a metal is deposited onto at least one bottom or sidewall of substantially all of the reaction chambers or top surface of the array using the PECVD method of vapor deposition. In a further embodiment, the metal chromium is deposited onto at least one bottom or sidewall of substantially all of the reaction chambers or top surface of the array using the PECVD method of vapor deposition. In another embodiment, the metal silver is deposited onto at least one bottom or sidewall of substantially all of the reaction chambers or top surface of the array using the PECVD method.

Figure 3:
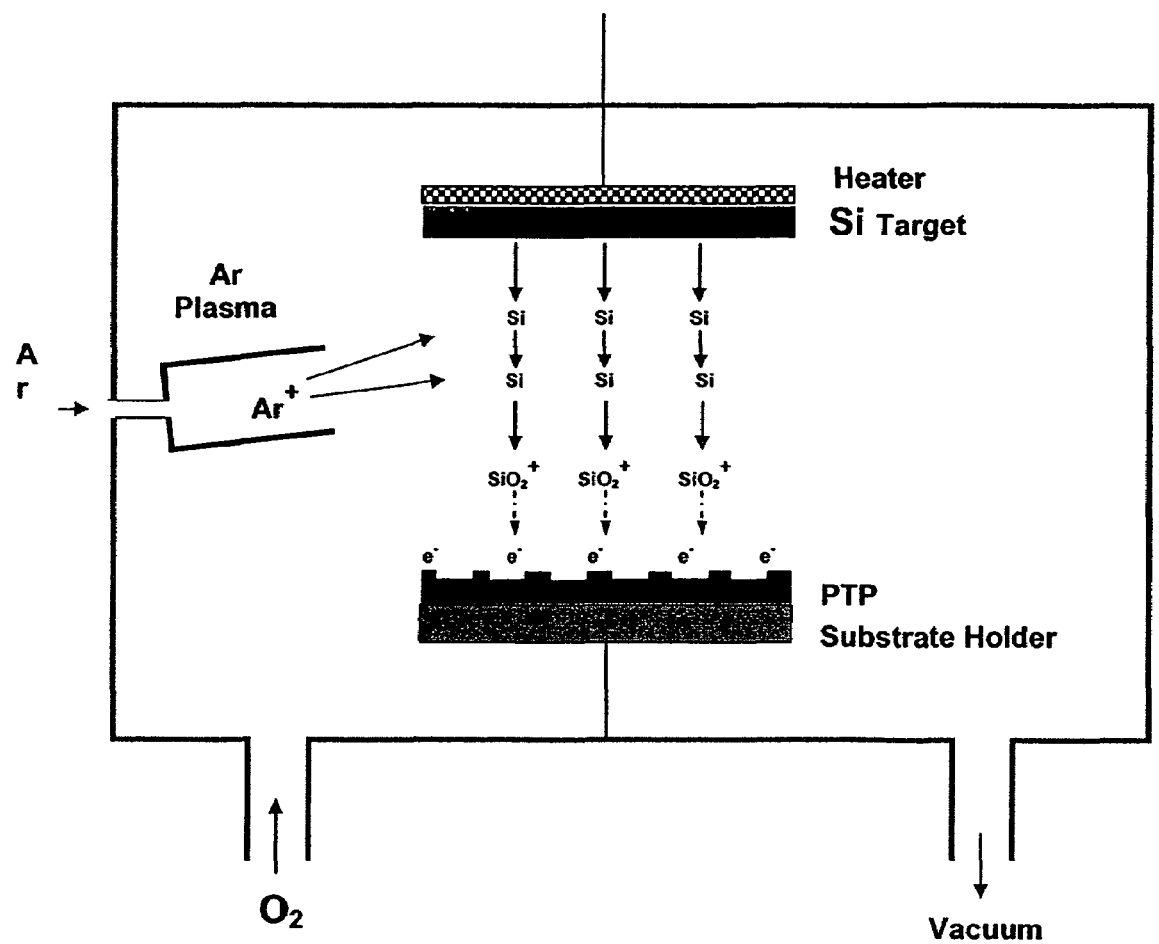
FIG. 3 is a schematic diagram of the ion-plating process.
Figure 23:
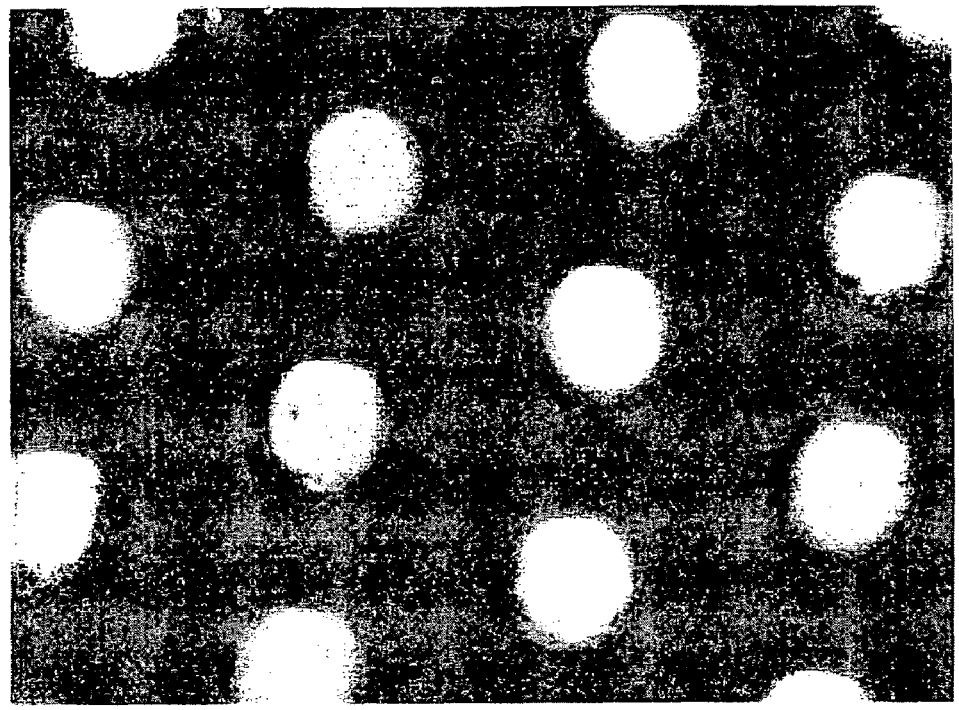
FIG. 23 shows two microscopic photos of the same etched fiber optic faceplate which has been coated with a non-transparent, silver coating. The top surface area of the array, the sidewall and corner area of each reaction chamber is coated with silver, such that the coating is absent in the center of the bottom which creates an aperture near the center of the bottom. Photo A is focuses on the bottom of the chamber and photo B is focused on the cladding.
Figure 23:
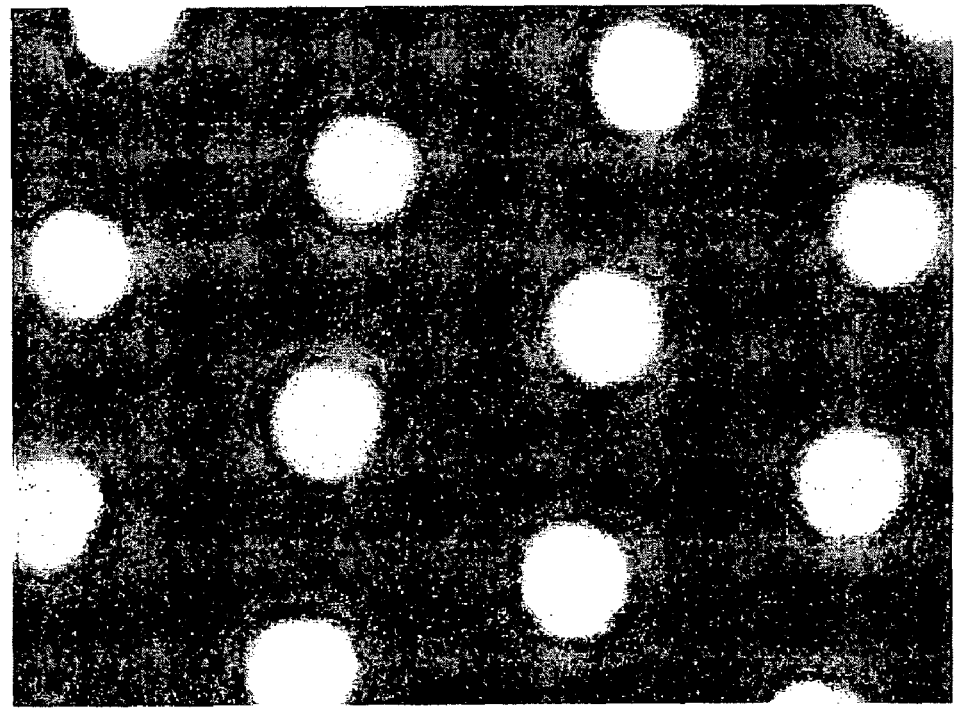

Ion-plating vapor deposition can be used to deposit the transparent and/or non-transparent coating. The ion-plating process typically incorporates characteristics of two other technologies, sputter etching and ion-beam mixing. In the ion-plating process, the substrate to be coated and the source of the coating material are held in a vacuum chamber within a low-pressure gaseous environment. Prior to being coated with the thin film coating, the substrate is "sputter cleaned." Energetic ions (electrically charged atoms) and neutral atoms of an activated inert gas strike the of the substrate to remove contaminants. Sputter cleaning is important to the ion-plating process because it produces a very reactive and atomically clean surface. The thin film coating material is evaporated, enhanced by the interaction with energetic inert gas (or reactive gas) atoms and ions, and deposited on the surface of the item. In one embodiment, when present the transparent and/or non-transparent thin film coating is deposited onto at least one bottom or sidewall of substantially all of the reaction chambers or top surface of the array using an ion-plating vapor deposition method which is a hybrid chemical-physical process. FIG. 3 shows a schematic of the ion-plating vapor deposition method. In one embodiment, a non-metal oxide is deposited onto at least one bottom or sidewall of substantially all of the reaction chambers or top surface of the array using the ion-plating method of vapor deposition. In one embodiment, the non-metal oxide, $SiO_2$ is deposited onto at least one bottom or sidewall of substantially all of the reaction chambers or a top surface of an FOF using the ion-plating method of vapor deposition (FIGS. 1e, 1f, and 2d). In another embodiment, a metal is deposited onto at least one bottom or sidewall of substantially all of the reaction chambers or top surface of the array using the ion-plating method of vapor deposition. In a further embodiment, the metal chromium is deposited onto at least one bottom or sidewall of substantially all of the reaction chambers or top surface of the array using the ion-plating method of vapor deposition. In another embodiment, the metal silver is deposited onto at least one bottom, or sidewall of substantially all of the reaction chambers or top surface of the array using the ion-plating method of vapor deposition (FIG. 23).

B. Liquid Deposition

Many liquid phase processes are used to apply the transparent or non-transparent thin film coating. In one embodiment, when present, the transparent and non-transparent thin film coatings or their precursor materials are applied in liquid form to at least one bottom or sidewall of substantially all of the reaction chambers or top surface of an array, and the material subsequently solidifies. Liquid phase processes are either physical or chemical or some combination. In one embodiment, when present, the transparent and non-transparent thin film material is dissolved in a volatile solvent, the resulting solution is applied to at least one bottom or sidewall of substantially all of the reaction chambers or top surface of the array and the solvent is allowed to evaporate, yielding a thin film coating via a physical liquid phase process. In another embodiment, when present, the transparent and non-transparent thin film coatings can be formed by a sol gel process, where inorganic silicates or organic siloxanes are dissolved in an appropriate solvent and applied to at least one bottom or sidewall of substantially all of the reaction chambers or top surface of the array. Upon drying and heating, the low molecular weight silicates/siloxanes undergo chemical condensation reactions to polymerize into a glass-like film via a hybrid physical-chemical liquid phase process.

Transparent and non-transparent thin film coatings deposited by liquid phase deposition are applied to at least one bottom or sidewall of substantially all of the reaction chambers or top surface of the array in a variety of ways. In one embodiment, array substrates are dipped into the coating solution and withdrawn in a controlled fashion, leaving a liquid coating with thickness controlled by the rate of withdraw of the substrate and the angle. In another embodiment, liquids are applied by spin coating, where the thin film solution is applied to at least one top or sidewall of substantially all of the reaction chambers or top surface of the array, which is then spun to spread the liquid evenly and to remove any excess. In another embodiment, the thin film solution is sprayed onto at least one top or sidewall of substantially all of the reaction chambers or top surface of the array, where the coalescence of droplets produces a transparent or non-transparent thin film coating. In another embodiment, a technique known as capillary coating is used to coat at least one bottom or sidewall of substantially all of the reaction chambers or top surface of the array with a transparent or non-transparent thin film. Capillary coating encompasses the use of a rolling cylinder partially immersed in the thin film solution. The substrate is moved close to the cylinder so that a meniscus is formed to the cylinder, and the cylinder is rotated at the same rate as the substrate is translated.

Figure 15A:
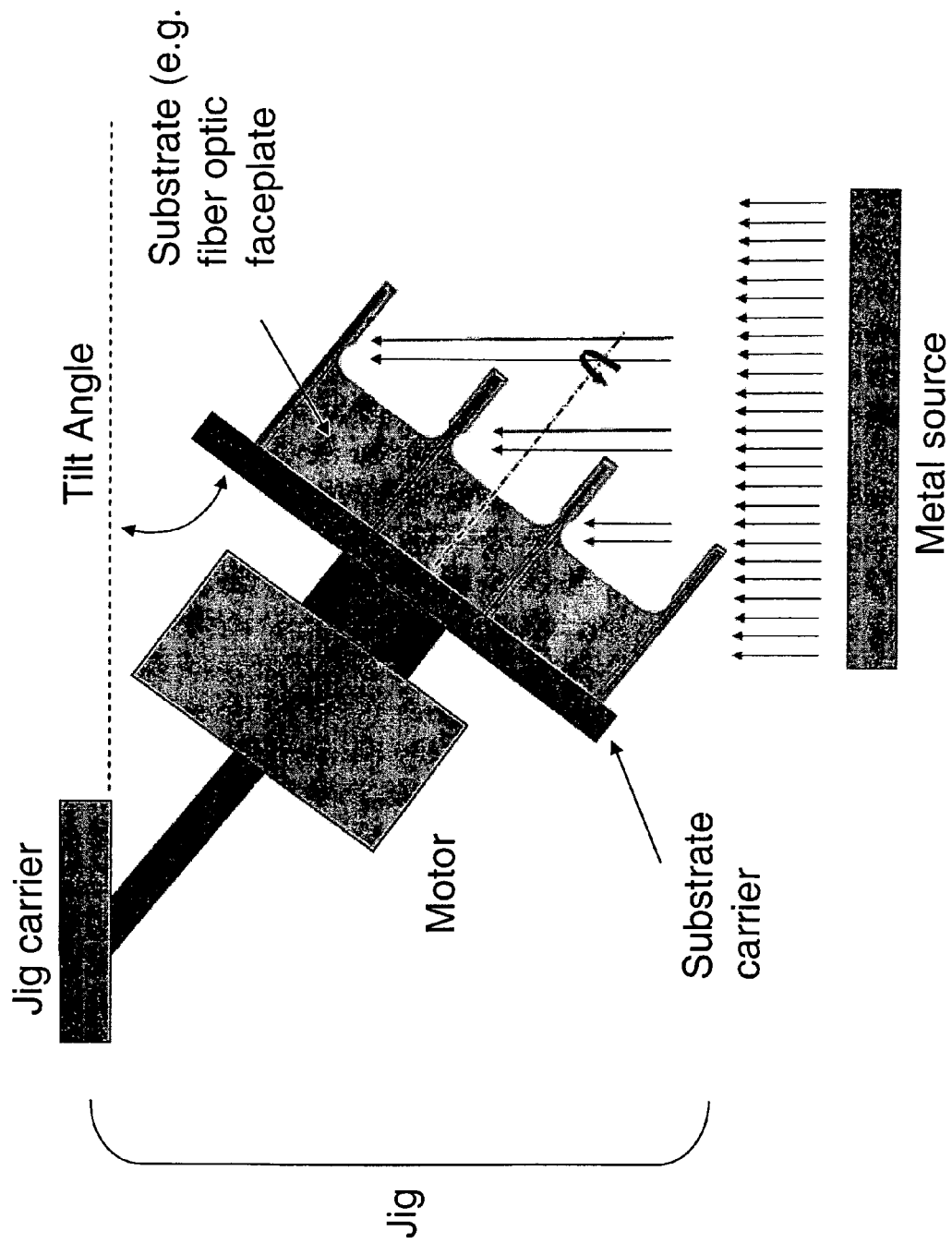
FIG. 15a illustrates the set-up used for the process of angled metal deposition using an angled jig. Shown is a side view of a fiber optic faceplate containing reaction chambers mounted onto the substrate carrier of a jig.

The invention provides processes for depositing a transparent or non-transparent thin film coating on the surface of an array which has a top surface and a bottom surface. In one embodiment, the invention provides processes is for depositing a transparent or non-transparent thin film coating on the bottom and sidewall of substantially all of the reaction chambers and top surface of the array. The invention also provides processes for depositing a transparent or non-transparent thin film coating on at least one sidewall or bottom of substantially all of the reaction chambers or top surface of the array of the array. For example, the invention provides a method for depositing a transparent or non-transparent thin film coating on the sidewall of the reaction chamber without depositing a the same thin film coating on the bottom of the reaction chamber. In one embodiment, the bottom of the reaction chamber is protected during the coating process and is not coated, because the bottom of the reaction chamber is in the shadow area (i.e., the coating is blocked by the sidewall of the reaction chamber and is therefore, not deposited onto the bottom of the reaction chamber). For example, FIG. 15*a* illustrates a reaction chamber where the sidewall creates a shadow, thereby protecting the shadow area on the bottom of the reaction chamber, such that no metal is deposited in the shadow area on the bottom of the reaction chamber. In one embodiment, the method of the invention utilizes shadows created by the sidewall of the reaction chamber and the rotation of the array at a tilt angle to control where the transparent or non-transparent thin film coating is deposited. In another embodiment, the array substrate is spinning during the process of depositing the transparent or non-transparent thin film coating. Spinning the array substrate allows for the thin film coating to be uniformly deposited.

The set-up for the process of depositing a metal on the sidewall and corner area of substantially all of the reaction chambers and top surface of the array is illustrated in FIG. 15*a*. The process involves tilting or angling the array substrate mounted on a carrier and rotating the substrate with a motor. As the array substrate rotates, the thin film coating is deposited on the sidewall and corner area of substantially all of the reaction chambers and top surface of the array, and the thin film coating is absent from the center of the bottom such that the absence of the coating creates an aperture near the center of the bottom of the reaction chamber. Changing the tilt angle of the rotating substrate results in the thin film coating being deposited in different patterns on the array substrate e.g., different shapes, gradients of thickness, or overlap of two coatings (FIG. 15*a*).

In one embodiment, the process of the invention deposits the transparent or non-transparent thin film coating over the entire surface of at least one bottom or sidewall of substantially all of the reaction chambers or top surface of the array e.g., the bottom surface of substantially all of the reaction chambers is completely coated with a thin film.

In another embodiment, the transparent or non-transparent thin film coating is deposited in the corner area of the reaction chamber such that the corner area is formed at the junction between the bottom and sidewall. The thin film coating is partially deposited on the bottom and partially deposited on the sidewall of the reaction chamber, such that the coating is absent from the center of the bottom of substantially all of the reaction chambers and forms an aperture (FIG. 16). In one embodiment, the angle at which the substrate is held (i.e., the tilt angle) can be adjusted to control the size of the aperture (FIG. 15*a*). Partial deposition of a non-transparent thin film coating on the corner area such that there is an absence of coating on the bottom of the reaction chamber further eliminates optical bleeding between adjacent reaction chambers and restrains any light beams which are directed down into the fiber strands for example when the array is being used for analysis (e.g,. DNA sequencing).

In one embodiment, the process of the invention is used to partially deposit (i.e., to coat) an opaque, non-transparent thin film coating over a portion of the surface of at least one bottom or sidewall of substantially all of the reaction chambers or top surface of an array e.g., the bottom of substantially all of the reaction chambers is partially coated with a thin film. In one embodiment, at least 80% of the bottom of substantially all of the reaction chambers of the array is coated with a transparent or non-transparent thin film.

In another embodiment, at least 60% of the bottom of substantially all of the reaction chambers of the array is coated with a transparent or non-transparent thin film. In another embodiment, at least 40% of the bottom of substantially all of the reaction chambers of the array is coated with a transparent or non-transparent thin film. In another embodiment, at least 20% of the bottom of substantially all of the reaction chambers of the array is coated with a transparent or non-transparent thin film. In another embodiment, at least 10% of the bottom of substantially all of the reaction chambers of the array is coated with a transparent or non-transparent thin film.

In another embodiment, the opaque non-transparent thin film coating is applied to the sidewall of substantially all of the reaction chambers on a fiber optic faceplate. The non-transparent coating completely covers the entire surface of the sidewall or alternatively, the non-transparent coating partially covers the surface of the sidewall. In one embodiment, at least 80% of the sidewall of substantially all of the reaction chambers of the array is coated with a transparent or non-transparent thin film. In another embodiment, at least 60% of the sidewall of substantially all of the reaction chambers of the array is coated with a transparent or non-transparent thin film. In another embodiment, at least 40% of the sidewall of substantially all of the reaction chambers of the array is coated with a transparent or non-transparent thin film. In another embodiment, at least 20% of the sidewall of substantially all of the reaction chambers of the array is coated with a transparent or non-transparent thin film. In another embodiment, at least 10% of the sidewall of substantially all of the reaction chambers of the array is coated with a transparent or non-transparent thin film.

In another embodiment, the opaque non-transparent partial coating on the bottom corner area and the sidewall corner area produces an optical obstacle and eliminates optical scattering through the cladding material and allows light to come through the bottom which is not covered with opaque second coating.

The method for depositing a transparent or non-transparent thin film can also be used to apply a thin film coatings to features found on a substrate e.g., boundary posts or column structures. The method is also used for coating the spaces on the bottom of the reaction chamber between the boundary post or column structures. The patterns of the posts produce different shadow patterns on the bottom.

Figure 18:
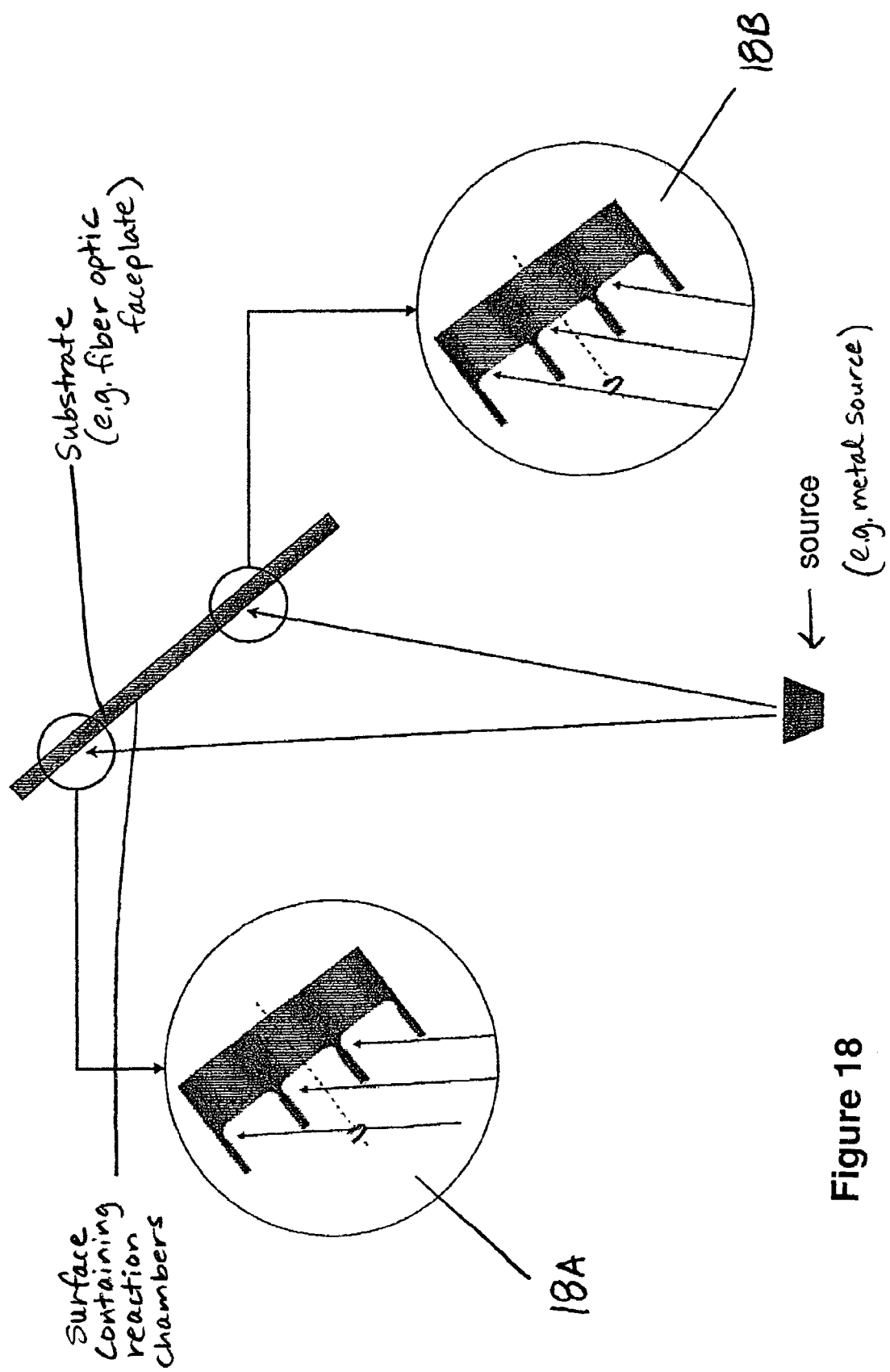
FIG. 18 illustrates "angle effects" that can occur when the ion source is considerably smaller than the substrate during vapor deposition of a coating. Angle effects produce an array with reaction chambers that are not uniformly coated. For example, A shows the coating being deposited in the corner area of three reaction chambers located on one end of the substrate, and B shows the coating being deposited on the bottom of three reaction chambers located on the other end of the substrate
Figure 19A:
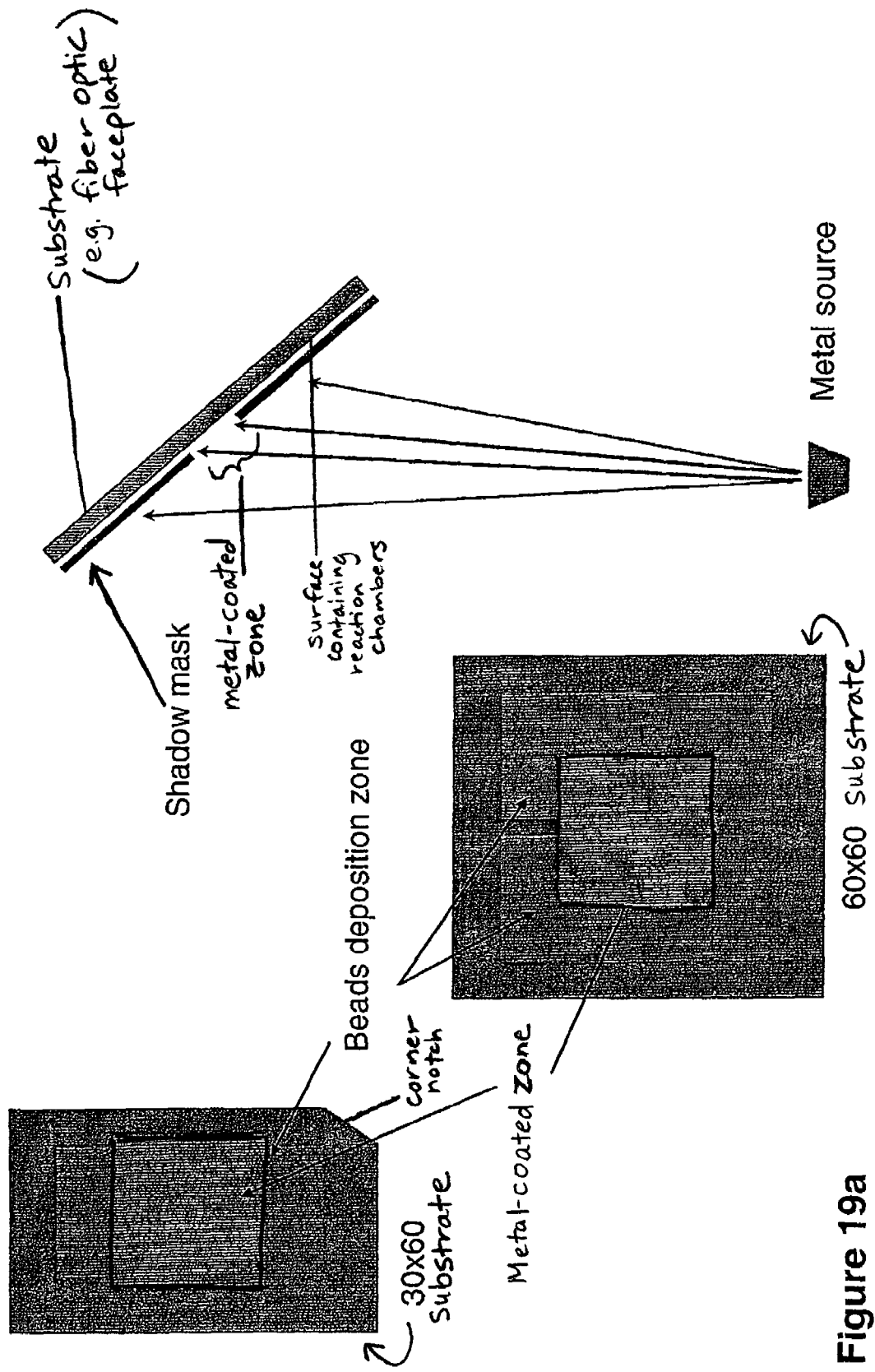
FIG. 19a illustrates the use of a shadow mask during the deposition process to direct the coating to a selected area (e.g., the "metal coated zone") of the fiber optic faceplate and to eliminate angle effects.
Figure 19B:
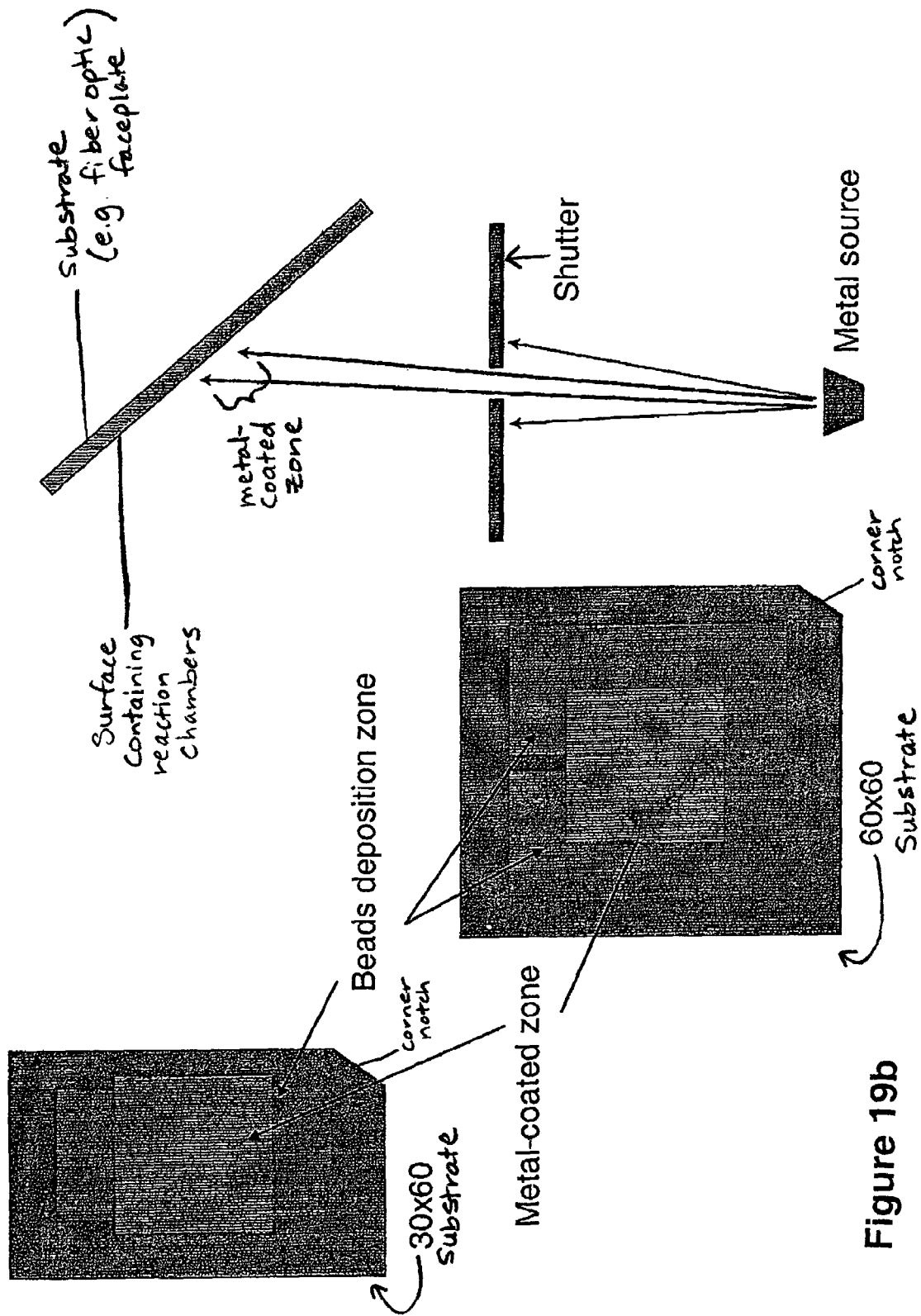
FIG. 19b illustrates the use of a shutter during the deposition process to direct the coating to a selected area (the "metal coated zone") of the fiber optic faceplate and to eliminate angle.

As shown in FIG. 18, angle effects can occur during the deposition process when the source (e.g., a metal ion source) is considerably smaller in size in comparison to the surface of the substrate for coating. Angle effects mean that the transparent or non-transparent thin film coating profile is varied (i.e. not uniform) at different locations on a array substrate. Angle effects produce an array with reaction chambers that are not uniformly coated. FIG. 18A shows the coating being deposited in the corner area of three reaction chambers located at one end of the substrate, and FIG. 18b shows the coating being deposited on the bottom of three reaction chambers located on the other end of the same array substrate. Strategies to eliminate angle effects include increasing the distance between the source and the substrate to be coated, putting a shadow mask in front of a substrate to shift and scan an entire substrate during deposition, introducing a shutter between the source and the substrate, or reducing the size of the shutter (aperture). FIG. 19a shows the use of a shadow mask during the deposition process to help direct the coating to a selected area (e.g., the "metal coated zone") of the substrate and to eliminate angle effects. The shadow mask is placed between the ion source and the substrate and can be positioned any distance from the substrate. FIG. 19b shows the use of a shutter during the deposition process to help direct the metal coating to a selected area, the metal coated zone, of the substrate.

One embodiment of the invention includes a process for depositing a non-transparent thin film coating on a substrate with a top surface containing a plurality of reaction chambers, where each reaction chamber is comprised of a bottom or sidewall; and the non-transparent coating is opaque, semi-opaque, shiny opaque, or translucent and is deposited on at least one bottom or sidewall, of substantially all of the reaction chambers or top surface of the array. The process involves (a) mounting a substrate onto a substrate carrier at an angle, (b) spinning the mounted substrate in a vacuum chamber, (c) depositing the non-transparent thin film onto at least one bottom or sidewall of substantially all of the reaction chambers or top surface of the substrate, (d) removing the substrate from the vacuum chamber, and (e) dismounting the substrate coated with the non-transparent substrate from the substrate carrier. In one embodiment, the process is used to deposit a non-transparent coating on the substrate which is a fiber optic faceplate. In another embodiment, the process is used to deposit a non-transparent coating onto at least one bottom or sidewall of substantially all of the reaction chambers or top surface of an array that is already coated on one bottom or sidewall of substantially all of the reaction chambers or top surface of the array with a transparent coating prior to the non-transparent coating being applied. In another embodiment, the process is used to deposit a non-transparent coating on to at least one bottom or sidewall of substantially all of the reaction chambers or top surface of an array that is coated on at least one bottom or sidewall of substantially all of its reaction chambers or top surface of the array with a transparent thin film that is optically transparent, 0.1-5.0 microns thick, and impermeable to water. In another embodiment, at least one bottom or sidewall of substantially all of the reaction chambers or top surface of the array is coated with a non-transparent coating prior to a transparent coating being applied to at least one bottom or sidewall of substantially all of the reaction chambers or top surface of the array.

Figure 15B:
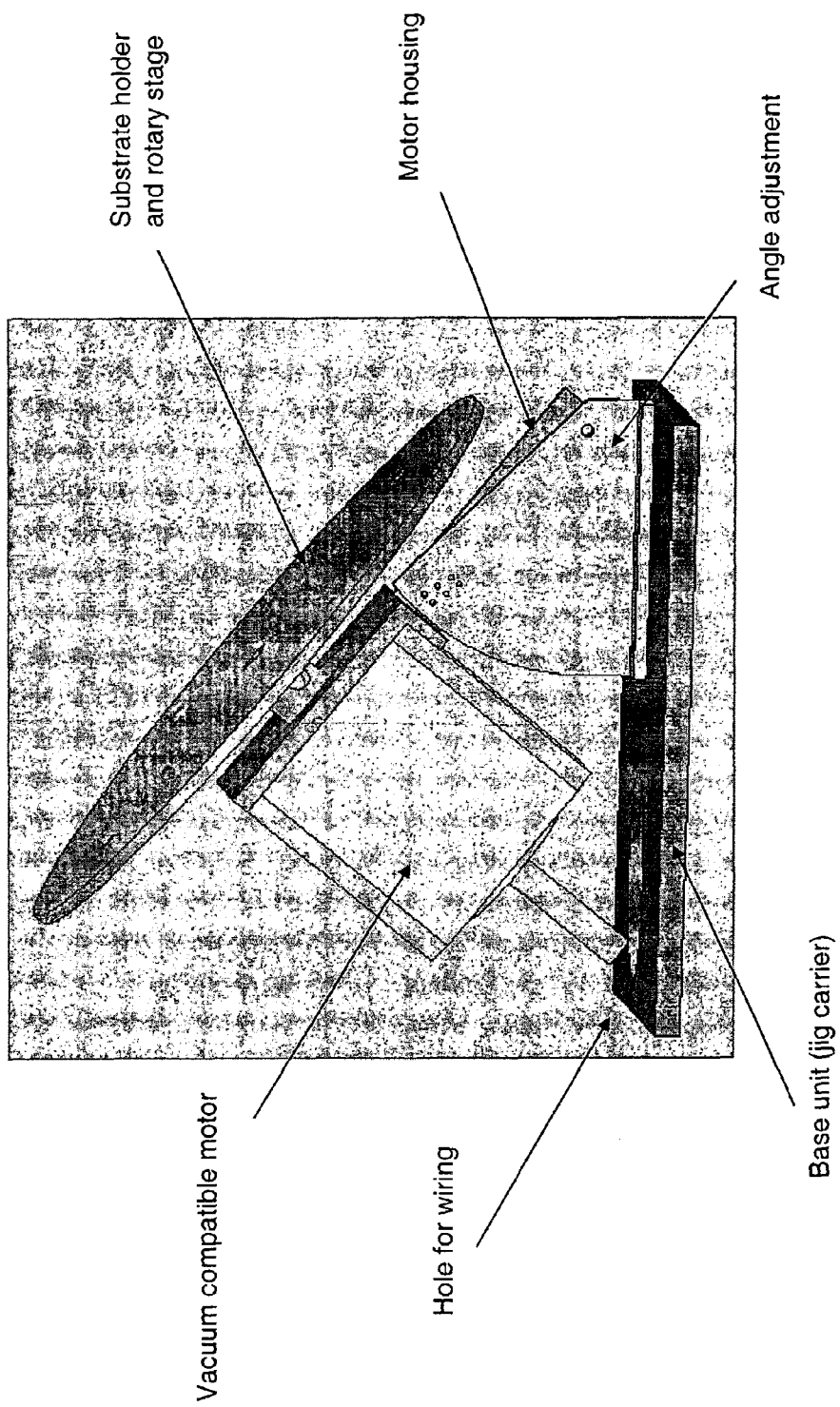
FIG. 15b illustrates the rotary and angled jig assembly.

In one embodiment, the process of angled metal deposition uses an angled jig and jig carrier assembly. FIG. 15a shows a side view of a fiber optic faceplate containing reaction chambers which is mounted onto the substrate carrier of a jig. The rotary and angled jig assembly is shown in FIG. 15b. The fiber optic faceplate is held at an angle (the "Tilt Angle") and rotated while a non-transparent coating e.g., a metal is evaporated from a source and deposited onto the sidewall and corner area of each reaction chamber nd the top surface of the array. The entire process can be carried out in a metal deposition chamber and the rotary disc can be driven by a vacuum compatible motor, which can rotate at less than 10 rpm.

C. Quality Control

After the coating process is complete, the quality of the resulting thin film coatings is evaluated using a number of different techniques. Both direct and functional methods are used to detect the presence of intact thin film coatings and to evaluate performance of the coated array. In one aspect of the invention, the coating on the array is uniform. Initially, a visual quality control inspection is performed which consists of visually inspecting each film coated array with a microscope in order to detect any gross defects. Small holes ("pin holes") in the coating indicate that the coating is of poor quality. In some embodiments, where the bottom is partially coated, the center of the reaction chamber bottom should be clear from any non-transparent coating to ensure that light can pass through the center of the chamber without any reduction in intensity. The diameter of the aperture formed on a partially coated bottom can be measured to determine whether the tilt angle used in the deposition process is correct. In one embodiment, diameter of the aperture formed by the partial coating on the bottom of the reaction chamber is about 28 microns. In another embodiment, the width of the ring formed when the coating is applied to the corner area is about 8.5 microns (FIG. 16b). In some embodiments, it is critical that the corner area of the reaction chamber is uniformly coated with the non-transparent coating so that light does not leak out to adjacent chambers. In one embodiment, the thickness of the non-transparent coating in the corner area of substantially all of the reaction chambers of the array is not less than 500 Angstroms (FIG. 16a)

Second, Scanning Electron Microscopy or "SEM" analysis is performed on the thin film coated array. SEM analysis is a key analysis method used to determine the quality of both transparent and non-transparent coatings. Typically, SEM images of both the thin film coated surface and a prepared cross-section are collected and analyzed. Surface images are analyzed for defects and coating damage as well as for overall morphology of the thin film coated surface, while cross-sections are measured for thickness. Select arrays are also evaluated for any potential effects by components used in a chemical reaction or bioassay and contained in the reaction chamber (e.g., the thin film coating is examined both before and after "mock" PCR conditions, See, Example 3). The thickness of the thin film coating can be measured. In one embodiment, SEM is used to determine thickness of the thin film coating. In another embodiment, the thickness of the thin film coating is measured by adding a sapphire coupon (Corion Division, Franklin, Mass.) to the batch, and determining the thin film (e.g. $SiO_2$) thickness after the coating process is complete by measuring the wavelength dependence on its light transmittance. The thickness of coatings is also followed by electroplating for thicker thin film deposition in order to produce additional features on the array.

The thin film coated arrays are also evaluated "functionally" regarding their performance for specific applications, e.g. DNA sequencing, to determine the effects of the thin film coating on PCR-induced sequencing background and overall quality of sequencing results. Such functional test can provide the advantage of single chamber resolution across the entire array surface. See, Example 4 and FIG. 4. A comparison of the light intensity generated during DNA sequencing reactions at two adjacent reaction chambers from coated and uncoated reaction chambers on the same array showed that a non-transparent coating can help to reduce optical bleeding between two adjacent chambers (see, Example 6 and FIGS. 24*a-b*).

5. Methods of Using Arrays

Thin film coated arrays can contain a number of different reactants and analytes in their reaction chambers. In one embodiment, each reaction chamber of the thin film coated array contains reagents for analyzing a nucleic acid or protein. Typically those reaction chambers that contain a nucleic acid (not all reaction chambers in the array are required to) contain only a single species of nucleic acid (i.e., a single sequence that is of interest). There may be a single copy of this species of nucleic acid in any particular reaction chamber, or there may be multiple copies. In one embodiment, a reaction chamber contains at least 100,000 copies of the nucleic acid template sequence. In another embodiment, the reaction chamber contains at least 1,000,000 copies. In further embodiment, the reaction chamber contains between 2,000,000 to 20,000,000 copies. In another embodiment, the reaction chamber contains between 5,000,000 to 15,000,000 copies of the nucleic acid. For example, if the apparatus of the invention is to be used for a pyrosequencing reaction, the ordinarily skilled artisan will appreciate that changes in the number of copies of a nucleic acid species in any one reaction chamber will affect the number of photons generated in a pyrosequencing reaction, and is routinely adjusted to provide more or less photon signal as is required. In one embodiment the nucleic acid species is amplified to provide the desired number of copies using PCR, RCA, ligase chain reaction, other isothermal amplification, or other conventional means of nucleic acid amplification. In one embodiment, the nucleic acid is single stranded.

The thin film coating provides an array with enhanced compatibility and functionality. One particular assay that has encountered problems due to array incompatibility is the analysis of nucleic acid molecules, specifically pyrophosphate sequencing (PPS) of PCR amplified nucleic acids. In one embodiment the thin film coated array is used to overcome a difficulty encountered in the PPS of PCR amplified nucleic acids. The PPS method used is according to the methods of U.S. patent application Ser. No. 10/767,779. See also, U.S. Pat. No. 4,863,849 and U.S. Pat. No. 4,971,903. When amplification is performed, followed by sequencing in the same reaction chamber, a "background" signal is observed. The source of this background is the released pyrophosphate (PPi) which remains strongly bound to the reaction chamber of the FOF such that it persists even after extensive washing. Therefore, a "background" assay was developed which involves performing solution phase PCR, washing the FOF, loading the FOF with Dynal sulforylase (S) and luciferase (L) beads (Fisher Scientific, Pittsburgh, Pa.), and measuring the signal (normalized to an earlier pyrophosphate flow). A reduction in the background noise in PPS would result in better sequencing results at a given signal level or allow equivalent sequencing result to be obtained at lower signal levels (Example 5).

Figure 4:
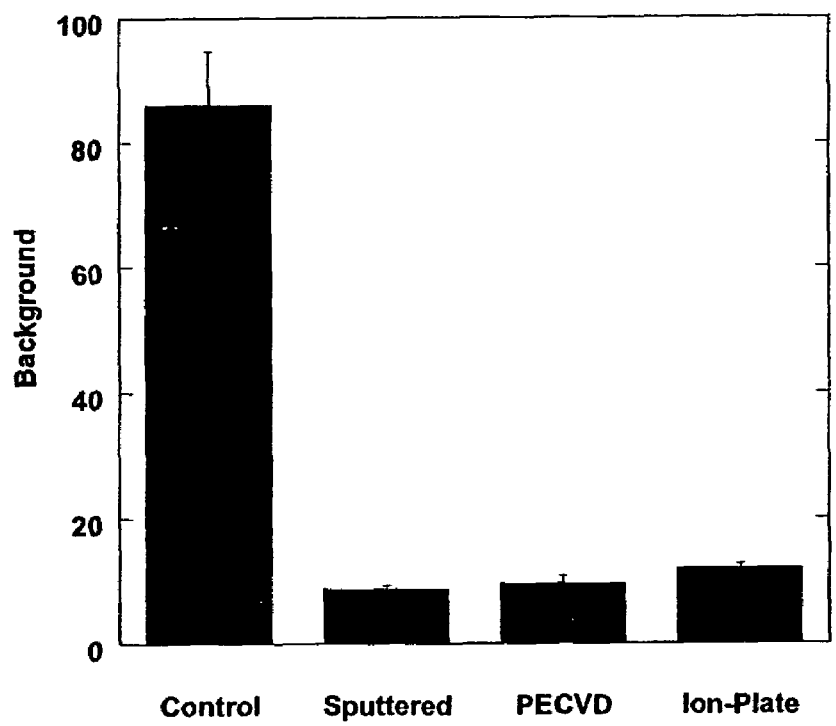
FIG. 4 is a bar graph showing PCR-induced sequencing backgrounds of $SiO_2$ coated and uncoated fiber optic faceplates comprising reaction chambers.
Figure 5:
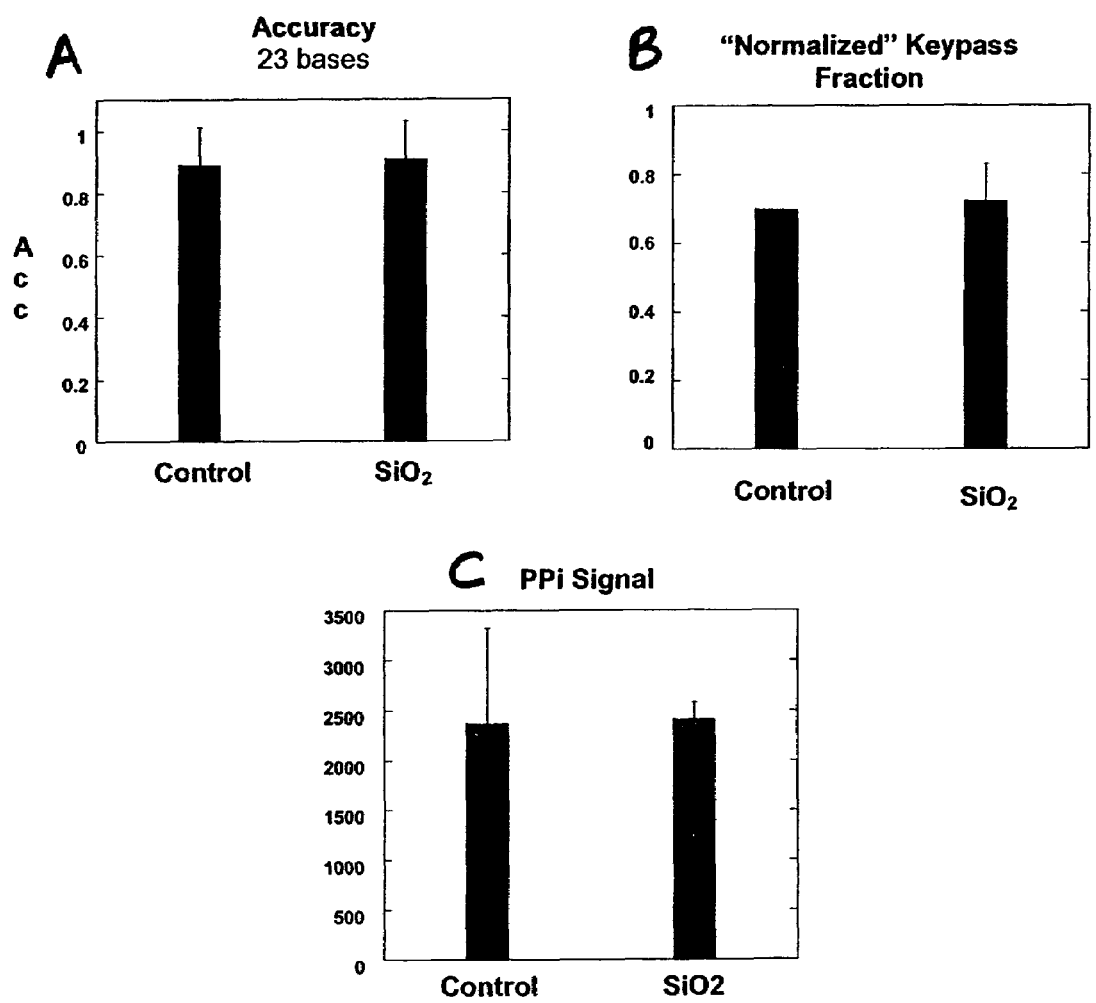
FIG. 5 is a series of graphs showing sequencing performance metrics of $SiO_2$ coated and uncoated fiber optic faceplates comprising reaction chambers for accuracy (FIG. 5a), "normalized" keypass fraction (FIG. 5b), and pyrophosphate (PPi) signal (FIG. 5c)

Thin film coatings on the reaction chamber of a microwell array can significantly reduce PCR-induced sequencing background as shown in FIG. 4. In one embodiment, a thin film coating of $SiO_2$ with a thickness of 0.1-5.0 microns on at least one or sidewall of substantially all of the reaction chambers or top surface of a FOF significantly reduces the PCR-induced sequencing background and provides for the same sequencing results as obtained in an uncoated array as shown in FIG. 5.

EXAMPLES

The following examples have been selected merely to further illustrate features, advantages, and other details of the invention. It is to be expressly understood, however, that while the examples serve this purpose, the particular conditions and details are not to be construed in a manner that would unduly limit the scope of this invention.

Example 1

General Etching Process and RER Cleaning Procedure

Figure 11A:
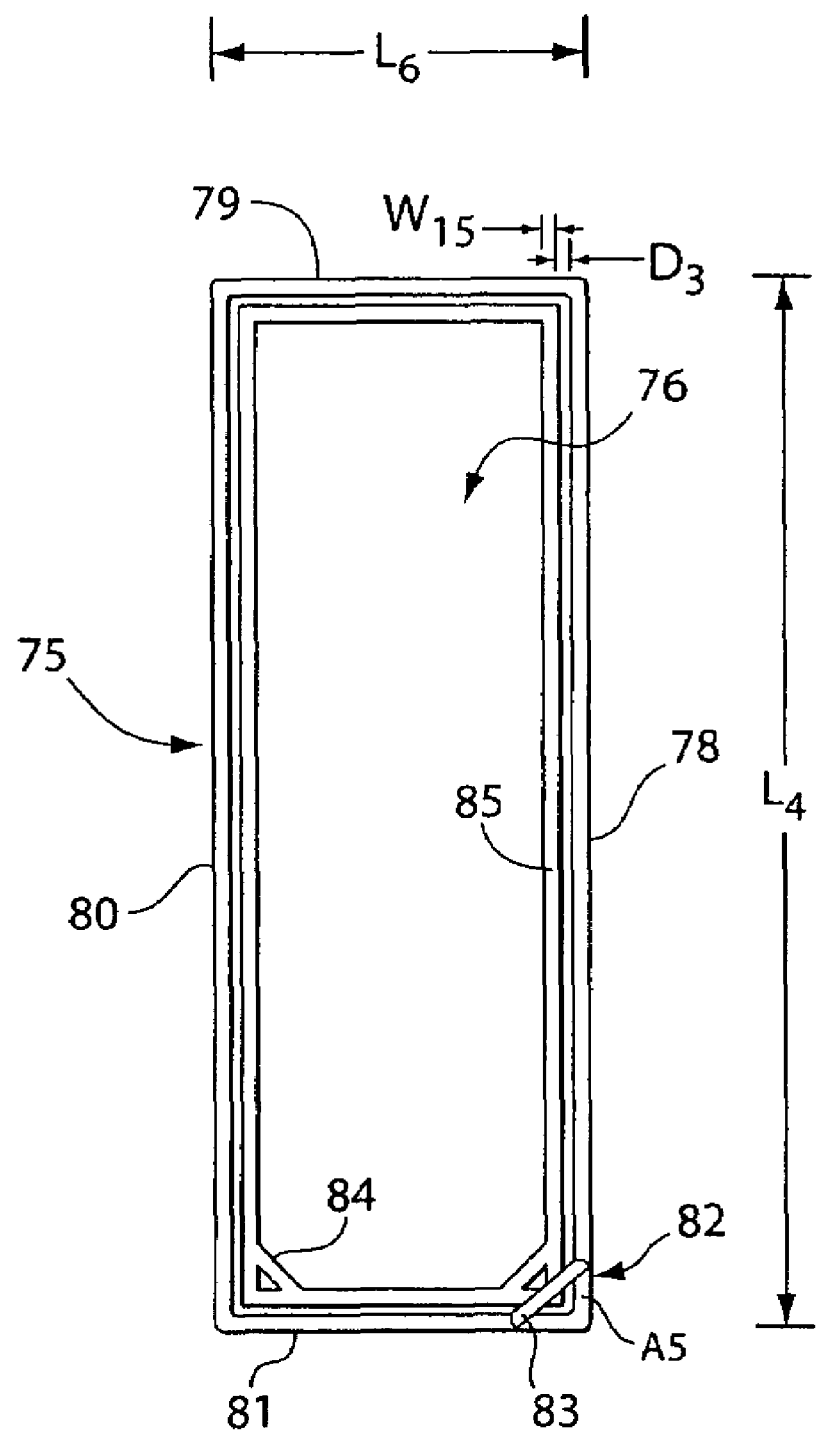
FIG. 11a is a drawing of an etch gasket (top view)
Figure 11B:
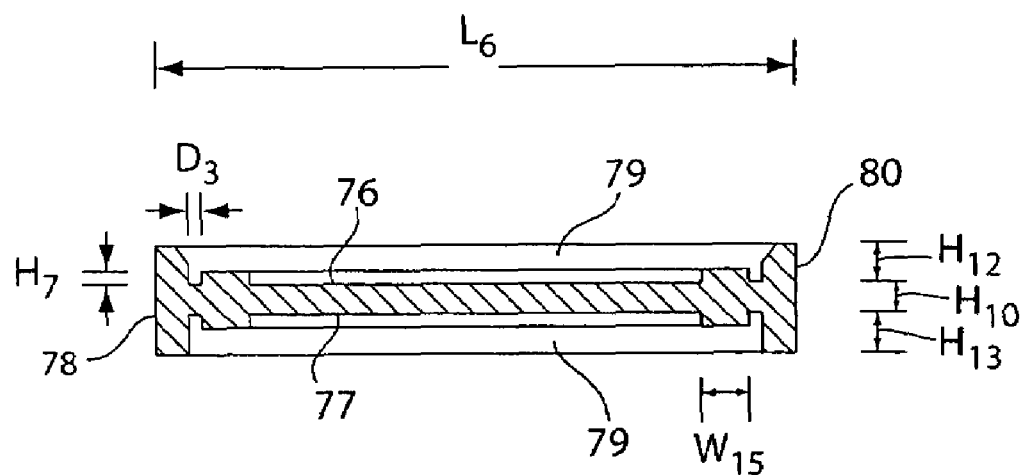
FIG. 11b is a drawing of an etch gasket (back end view)
Figure 11C:
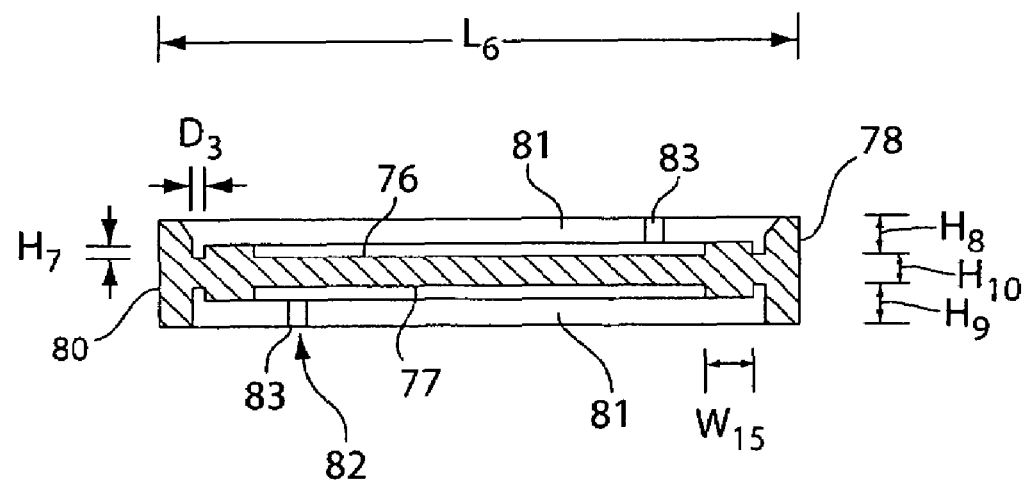
FIG. 11c is a drawing of an etch gasket (front end view)
Figure 11D:
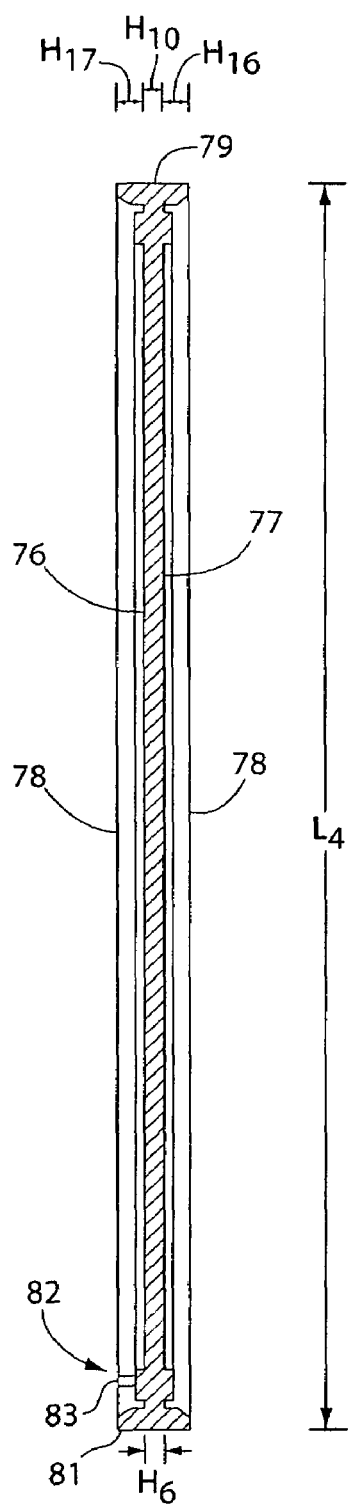
FIG. 11d is a drawing of an etch gasket (first side view)
Figure 11E:
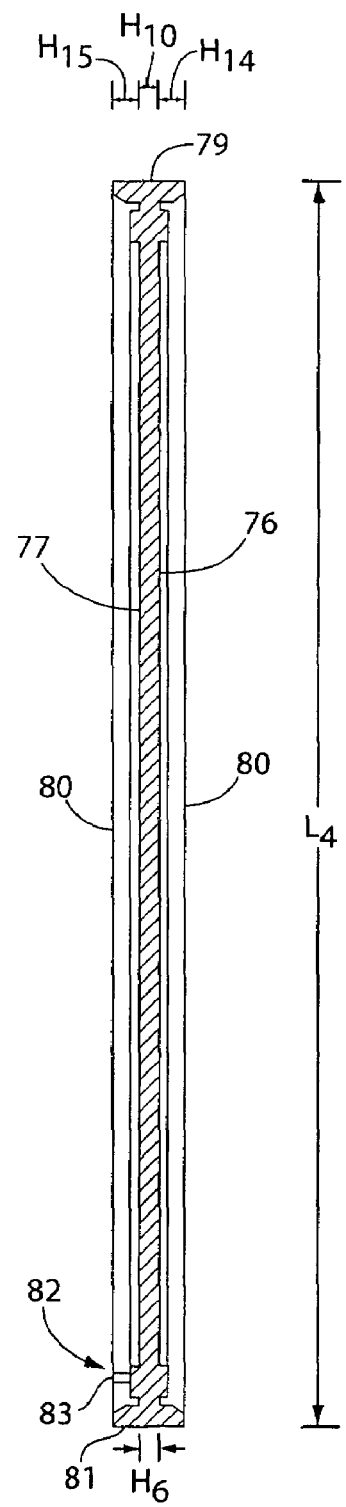
FIG. 11e is a drawing of an etch gasket (second side view)

This example describes the general single-sided etching process for FOFs (Incom Corporation, Charlton, Mass.) sizes 25×75 mm or 40×75 using silicon etch gaskets and PEEK (Poly Ether Ether Ketone) plastic clamps (FIGS. 11*a* and 11*b*). Distilled water for the Branson Ultrasonic bath (Fischer Scientific, Hampton, N.H.), from a PicoPure™ water purification unit ("PicoPure water"), was degassed for 10 minutes. The NesLab recirculator (Portsmouth, N.H.) was set to 57.2° C. (at this setting, water inside the ultrasonic bath was maintained at a constant temperature of 55° C.). Four stainless steel containers were covered and placed in the ultrasonic bath. Each container was charged with 1000 mL (for a 25×75 mm FOF) and 1200 mL (for a 40×75 mm FOF) of 20% $HNO_3$ and warmed to 55° C. Ninety-six unetched FOFs were loaded into each of the 96 positions of four etch trays. A designated FOF was selected and weighed. The difference in FOF weight before and after etching was plotted in order to correlate weight loss due to reaction chamber depth.

A pair of unetched FOFs was combined by positioning a silicon gasket (FIG. 13) in between the two FOFs and properly aligning each, such that the polished side of each FOF is facing the gasket and within the edge of the gasket. The corner notch of the FOF is aligned with the corner barrier on the gasket. The first PEEK clamp was affixed to hold the two FOFs and gasket together vertically and squeeze the plates together. The clamp was snapped on down the center of the long end of the FOFs starting with the bottom-most clip. The second PEEK clamp was applied. The finished "clamped sandwich" is shown in FIG. 12. The remaining unetched FOFs were combined and clamped as described above. Next, 12 clamped sandwiches were positioned into each of the four stainless steel racks. Once the temperature of the $HNO_3$ reached 55° C., the ultrasonic bath was turned on and the lids of the other 3 stainless steel containers removed. Each of the four stainless steel racks holding FOFs was transferred into the acid at 55° C. The FOFs were kept in the 55° C. acid bath. The etch rate of the FOFs was approximately 0.245 μm/min. The length of time that the FOFs remained in the bath depends on the desired reaction chamber depth. For example, an etch time of 3 hours and 44 minutes resulted in a reaction chamber depth of 55 μm.

The etched FOFs (i.e. FOFs) were removed from the acid bath and placed directly into stainless steel containers filled with 1.0 L of PicoPure water, and sonicated for 5 minutes. The water was discarded and the containers were filled with 1.0 L of PicoPure water, and sonicated for an additional 5 minutes.

The FOFs were removed from the rinse water and PEEK clamps and silicon gaskets were detached from each pair of FOFs.

To complete the post etch testing, the designated FOF was re-weighed and change in weight due to the etching was recorded. A count of the number of individual fibers with impaired optical transmission (a "dark fiber count") was preformed using a microscope.

A five step RER cleaning procedure using RCA cleaner, and ethylenediamine tetra-acetic acid (EDTA) ("RER cleaning procedure") for etched FOFs was conducted. "RCA" is the abbreviation for a solution of ammonium hydroxide ($NH_4OH$) and hydrogen peroxide ($H_2O_2$). To prepare RCA cleaner 1.0 L of $NH_4OH$ and 1.0 L of $H_2O_2$ were combined under a hood and the solution was mixed using a magnetic stir bar. Ninety-six (96) FOFs from the same lot were placed into the glass slide racks.

Step 1—First RCA Wash

RCA cleaner was prepared by combining a 1:1 solution of $NH_4OH$ and $H_2O_2$. For the 25×75 mm FOF, 200 mL of RCA cleaner was added to each of the glass staining dishes (Fisher Scientific, Pittsburgh, Pa.). For the 40×75 mm FOF, 200 mL of RCA cleaner was added to the polypropylene staining dishes. Six staining dishes were placed into the container of one rotator of an Ocelot Rotator (Boekel Scientific, Feasterville, Pa.) and the other dishes were placed on the other rotator. The shake speed was set at C. After 30 minutes, the RCA cleaner was disposed. Each set of 10 FOFs was rinsed 5 times with 200 mL of PicoPure water.

Step 2—First EDTA Wash

EDTA (200 mL) was added to each staining dish. The six dishes were placed into the container on one of the rotators and the other 4 dishes were placed into the container on the other rotator. The shake speed was set at C. After 30 minutes, the EDTA was disposed. Each set of 10 FOFs was rinsed with 200 mL of PicoPure water 5 times.

Step 3—Second RCA Wash

A fresh solution of RCA cleaner (1:1 $NH_4OH$ and $H_2O_2$) was prepared and 200 mL of RCA cleaner was added to each of the staining dishes. The six dishes were placed into the container on one of the rotators and the other 4 dishes were placed into the container on the other rotator. The shake speed was set at C. After 30 minutes, the RCA cleaner was disposed. Each set of 10 FOFs was rinsed with 200 mL of PicoPure water 5 times.

Step 4—Second EDTA Wash

EDTA (200 mL) was added to each staining dish. The six dishes were placed into the container on one of the rotators and the other 4 dishes were placed into the container on the other rotator. The shake speed was set at C. After 30 minutes, the EDTA was disposed. Each set of 10 FOFs was rinsed with 200 mL of PicoPure water 5 times.

Step 5—Sonicating the FOFs

The NesLab recirculator was charged with the appropriate amount of water and the temperature point was set to 40° C. with the low temperature alarm at 5° C. and the high temperature alarm at 100° C. The FOFs were placed into a stainless steel rack (Fisher Scientific, Pittsburgh, Pa.) loading the FOFs into every other slot to allow for good flow of the cleaning solution. The filled racks were placed into a polypropylene pan filled with a 5% Contrad® solution with the solution completely covering the FOFs. The 5% Contrad® solution was prepared by combining 1000 mL of deionized water with 50 mL of Contrad® (Fisher Scientific). The pans were then covered with a HDPE (high density polyethylene) cover. When the temperature of the recirculator reached 40° C., two polypropylene pans containing the FOFs were submerged in the water. The FOFs were sonicated for 90 minutes and then removed from the sonicator. The racks were removed from the pans and the Contrad® solution drained. The polypropylene pans were filled with PicoPure water. The stainless steel racks were placed back in the pan and the FOFs were rinsed 2 times. The pan was refilled a third time with PicoPure water and taken to the Ocelot Rotator and rotated on speed C. After 5 minutes, the FOFs were rinsed with water 2 times. The FOFs were covered with tin foil and allowed to dry in the stainless steel racks.

Example 2

FOF Coating Using Ion-Plating Deposition Method

FOFs were immediately cleaned prior to thin film coating. The detergent used was Contrad®. The Branson sonicator was set to 40° C. Two FOFs were placed back to back in a Falcon tube, and 40-45 mL of 5% Contrad® solution was added in the tube and the cap closed. The tube was loaded in the sonicator and sonicated for 90 min. FOFs were removed from the tube, rinsed thoroughly with fresh deionized water, and transferred to a new Falcon tube and filled with deionized water. The detergent solution was disposed in the sink and FOFs kept in de-ionized water at 4° C.

After cleaning, the ion-plating process for coating a chemically etched FOF with a thin film $SiO_2$ coating was performed. The FOF to be coated was placed on an electrically isolated holder in a vacuum chamber, along with an electrically isolated heated silicon target, an argon plasma source, and a source of oxygen. The argon plasma source was ignited, which generated an overall negative charge on the FOF. Silicon vapor was produced by evaporation of the heated target, and reacted with the argon plasma, as well as the oxygen to form positively charged $SiO_2$ species. These $SiO_2$ species attract to the negatively charged FOF, where they energetically condense, forming a glassy, unstructured $SiO_2$ film. The film morphology and homogeneity is a complex function of many process variables, but the film thickness was precisely controlled by the exposure time in the chamber. See FIGS. 1 and 2.

Example 3

Exposure of the Transparent Thin Film Coated FOF to "Mock" PCR Conditions

Transparent thin film coated, etched FOFs were tested for environmental robustness by exposing the etched FOF coated with $SiO_2$ to deionized water at temperatures (approximating PCR thermal exposure), and examining SEM images of both the surfaces and cross-sections for signs of coating damage according to the following procedure. One milliliter of 1×HiFi PCR buffer (Invitrogen, Carlsbad. CA) was prepared. The thin film, etched FOF was placed on top of tissues and using a cell scraper, the excess water was removed. Quickly, 400 μL of the buffer was added on top of the FOF surface and the solution was evenly spread out with a cell scraper. After 1 minute, the excess solution was removed. The procedure of adding 400 μL of the buffer followed by removing the solution was repeated. The FOF was immediately placed in an in-house amplification device (the "AMP jig") (454 Life Sciences, Branford, Conn.), covered with a silicon rubber plate and foam, and the AMP jig screws were tightened as described in Leamon et al., Electrophoresis 24: 3769-3777 (2003). The AMP jig was loaded into a Thermocycler MJ PTC 225 Tetrad (MJ Research, Waltham, Mass.) and the thermocycling program was run. The details of the temperature profile were as follows: total run time is 4.5 hours, 1) 40 short cycles: 94° C.: 15 sec; 58° C.: 15 sec; 68° C.: 15 sec; 2) 10 additional long cycles: 95° C.: 30 sec; 58° C.: 10 min. The procedure was repeated for a total of 80 cycles. After thermocycling, the FOF surface was rinsed with fresh water. The surface was dried with nitrogen flow and the $SiO_2$ coating was measured by optical microscopy and SEM analysis. Since SEM analysis is a destructive technique, "before" and "after" analysis of the same thin film etched FOF could not be performed. However, all thin film etched FOFs examined by SEM after the above "mock-PCR" procedure showed no apparent damage to the $SiO_2$ coating on the FOFs.

Example 4

Evaluation of PCR-Induced Sequencing Background

A 1 mL LuerLock® syringe (20G1) (Becton Dickinson, Franklin Lakes, N.J.) was charged with 525 μL of PCR solution (1× Platinum HiFi Buffer (Invitrogen, Carlsbad, Calif.), 2.5 mM MgSO4, 0.5% BSA, 1 mM dNTPs (MBI Fermentas, Hanover, Md.) and the syringe needle was connected to an in-house loading device (the "loading jig") (454 Life Sciences, Branford, Conn.). dNTP refers to the 4 deoxynucleotide triphosphates (dATP, dCTP, dGTP, and dTTP). An etched FOF coated with $SiO_2$ was removed from a deionized water bath, placed on the lab bench and using a cell scraper, excess water was removed from the FOF surface. The FOF was quickly assembled on the loading jig with 4 plastic clips. The fluid chamber was filled to the top with PCR solution by pushing the syringe forward. After 3 minutes, the solution had diffused into the reaction chambers.

The plunger was pulled back and the loading jig disassembled. The FOF was immediately placed in an AMP jig and covered with a silicon rubber plate and foam. Jig screws were put in place and tightened. The jig assembly was loaded in the Thermocycler and the thermocycling program was run. The details of the temperature profile were as follows: total run time is 4.5 hours, 1) 40 short cycles: 94° C.: 15 sec; 58° C.: 15 sec; 68° C.: 15 sec; 2) 10 additional long cycles: 95° C.: 30 sec; 58° C.: 10 min.

After thermocycling, the AMP jig was opened, the FOF was removed and placed in a 50 mL Falcon tube (Becton Dickinson, Franklin Lakes, N.J.) containing 50 mL of deionized water. The tube was then positioned on a Clay Adams® Nutator Mixer and nutated for 20 min to dissolve the PCR product. Nutation is a gentle orbital motion that can assure uniform mixing without foaming. The FOF was transferred into 50 mL of Assay Buffer ("AB") with BSA (bovine serum albumin). AB is a buffer solution containing tricine and magnesium acetate. The resulting solution was collected for the PCR sequencing analysis described in the following example (Example 5).

The bead mixture was prepared (Bangs beads 175 μL+Dynal beads 175 μL) and diluted with 700 μL of deionized water. Bangs beads are microspheres carrying immobilized sulfurylase and luciferase enzymes, and dynal beads are magnetic beads carrying the bound enzymes of luciferase and sulfurylase. Nineteen adhesive pads (3M VHS, St. Paul, Minn.) containing 13.2 μL of bead mixture each were used to seal the inlet holes. The FOF was then spun using an Allegra 6R Centrifuge (Beckman Coulter, Fullerton, Calif.) for 8 minutes at 2000 rpm. The background run was performed and total time was 24 min: 1) wash 5 min; 2) PPi 2 min; 3) wash 10 min; 4) PPi 2 min; and 5) wash 5 min). After the run, a trace analysis was performed using Kangaroo software (454 Life Sciences, Branford, Conn.). Adjusted counts were obtained by subtracting 500 from raw counts. The whole procedure was repeated for both uncoated and $SiO_2$ coated FOFs for background comparison.

Example 5

PCR Sequencing Results

For validation of PCR results, uncoated and $SiO_2$ coated FOFs were paired and tested simultaneously using the solution collected for analysis in Example 5. Each solution (for both $SiO_2$ coated and uncoated arrays) was doubled by dilution with deionized water. Then, the PCR product in each was quantitated using an iCycler® RealTime PCR unit (Bio-Rad, Hercules, Calif.). Using fluorescence measurements, the amount of amplified product was determined. Finally, the number of molecules per reaction chamber after PCR was calculated. Normal range of the number is $10^3$-$10^9$ order. The results are shown in Table 2 below and the results are in the range of $10^6$-$10^8$ and are acceptable. All of the $SiO_2$ coated FOFs produced equal level of the PCR product compared to the uncoated FOFs.

TABLE 2

Results of in-reaction chamber PCR

| Uncoated (Control) | | $SiO_2$-coated | |
|---|---|---|---|
| FOF Number | Molecules/Reaction Chamber | FOF Number | Molecules/Reaction Chamber |
| FOF #1 | $8.21 \times 10^7$ | FOF #3 | $1.70 \times 10^8$ |
| FOF #2 | $1.10 \times 10^8$ | FOF #4 | $3.98 \times 10^7$ |
| | | FOF #5 | $1.70 \times 10^8$ |
| | | FOF #6 | $4.40 \times 10^7$ |
| | | FOF #7 | $8.16 \times 10^7$ |
| | | FOF #8 | $6.04 \times 10^6$ |

Example 6

Comparison of Profile of Light Intensities in Adjacent Reaction Chamber

A FOF array (40×75 mm) was prepared, where the first half of the array was coated with two coatings, a non-transparent coating and a transparent coating, and the second half of the array was coated with only one transparent coating. DNA sequencing reactions were carried out in reaction chambers on both halves of the array and the light intensities generated were compared.

A non-transparent, aluminum metal coating was applied to the first half of the array and then a transparent $SiO_2$ coating was applied on top of the aluminum coating to the first half of the array. The aluminum coating was applied to the top surface of the array and the sidewall of the reaction chambers and partially applied to the corner area of the reaction chambers, such that the diameter formed by the metal coating near the center of the bottom was 28.77 microns. The thickness of the aluminum coating measured on the top surface of the array was 200 nm. While the metal coating was being applied the second half of the array was protected by a shadow mask. After the metal coating was applied, the transparent, $SiO_2$ coating was applied on the top surface of the array and the bottom and sidewall of the reaction chambers of both the first and second halves of the array.

Pyrophosphate sequencing analysis of PCR-amplified nucleic acids as described in U.S. patent application Ser. No.

Figure 24:
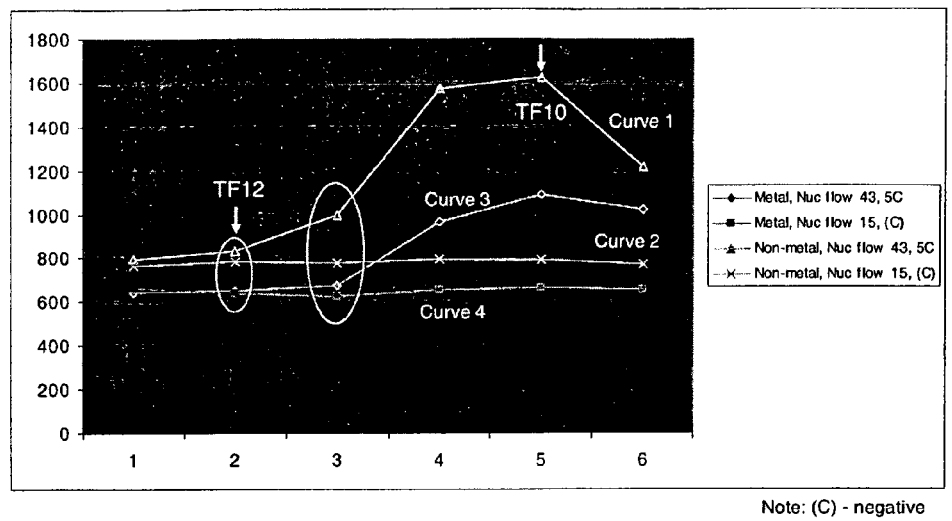
FIG. 24 A and B are graphs illustrating how a non-transparent, metal coating that is applied to the sidewall of the reaction chambers of an array can reduce optical bleeding between two adjacent chambers on an array. The two graphs represent two different nucleotide flow orders.
Figure 24:
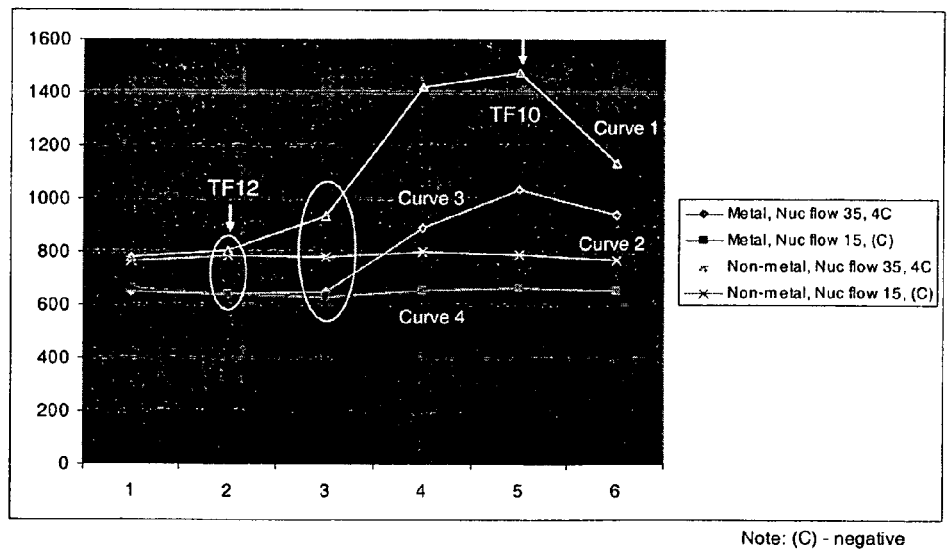
Figure 25A:
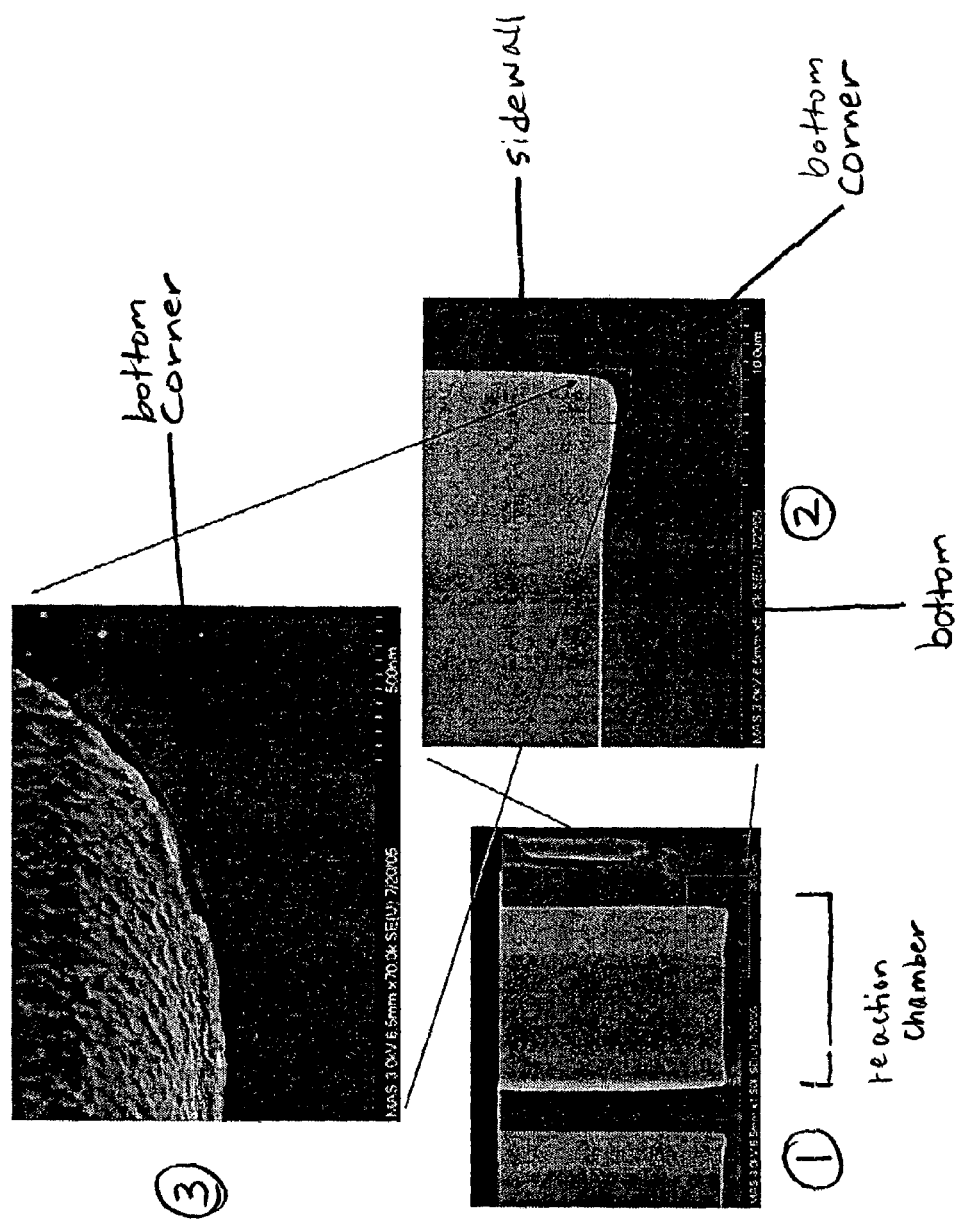
FIG. 25a shows three views of a silver coating on the corner of a reaction chamber of a fiber optic faceplate, the silver coating covers the bottom corner of the chamber. The thickness of the coating is such that it blocks light and shields photons from leaking into adjacent chambers. View 1 shows the entire reaction chamber. View 2 is a close-up of the corner of the chamber, and View 3 is a magnified view of this corner.
Figure 25B:
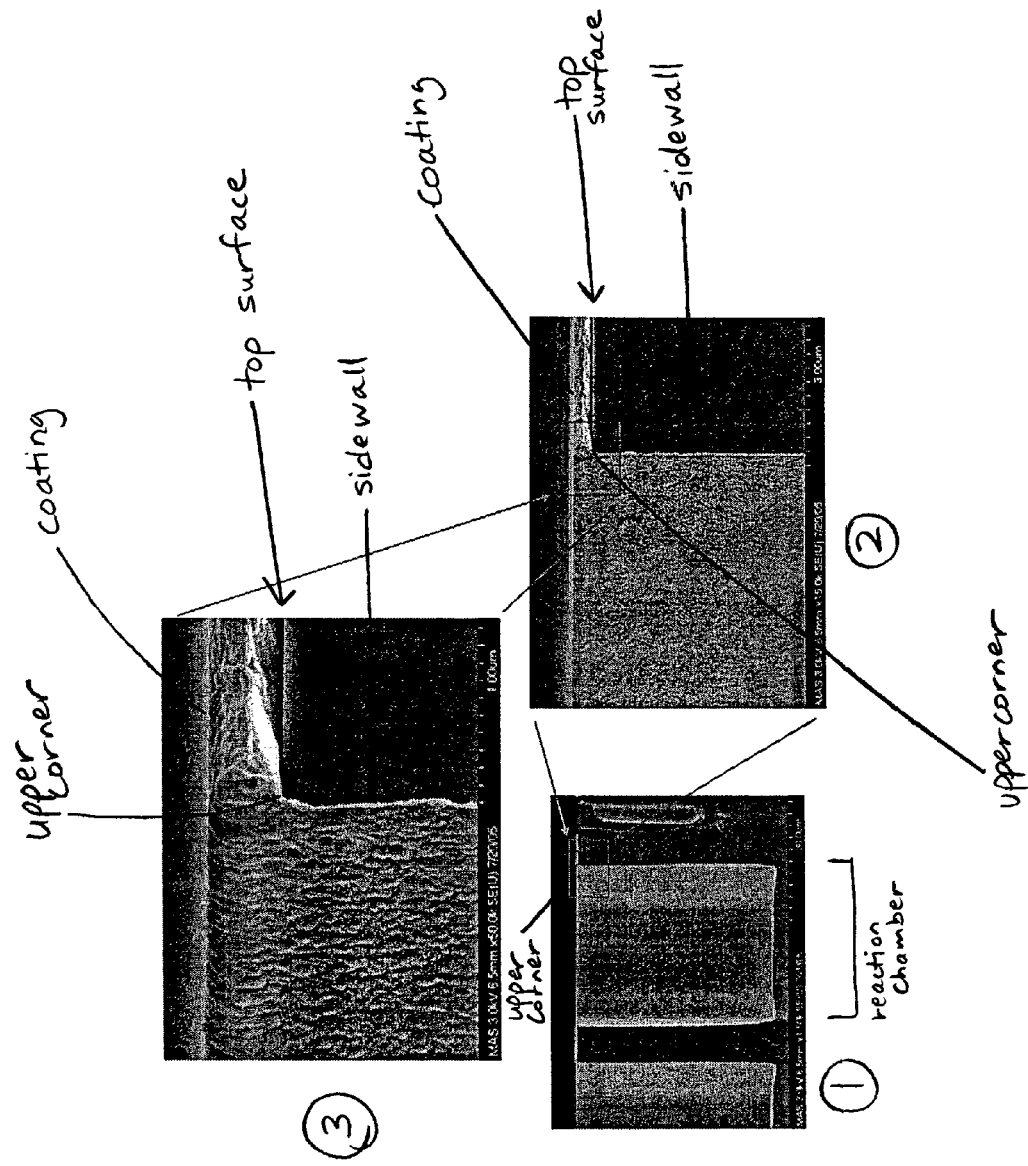
FIG. 25b shows three views of a silver coating on the upper corner of a reaction chamber and the top surface of a fiber optic faceplate, where the thickness of the coating on the sidewall is different from the thickness on the top surface of the cladding. This difference in thickness is due to the spinning of the substrate during the metal deposition process. View 1 shows the entire reaction chamber. View 2 is a close-up of the upper corner and the top of the reaction chamber, and the View 3 is a magnified view of this upper corner.

10/767,779 was conducted in reaction chambers located on both halves of the array. FIGS. 24a and 24b show the results of these experiments.

In FIG. 24a, the two arrows indicate the center points of two adjacent reaction chambers located on the second half of the array. The center points of these two adjacent chambers are at pixel No. 5 and pixel No. 2, respectively. One reaction chamber (pixel No. 5) contained Test Fragment 10 DNA ("TF10") and the other chamber (pixel No. 2) contained Test Fragment 12 DNA ("TF12"). The sequencing process was conducted at a nucleotide flow order of 43. The nucleotide flow order is defined as a specific nucleotide injection into a stream of a solution running through a DNA sequencing machine (e.g., a 454 Squencer 1.0). During the DNA sequencing process, a series of specific nucleotide solutions are injected into the solution stream and each injection is given a flow number. At a nucleotide flow order of 43, the TF10 DNA underwent 5 multiple DNA incorporations and produced a high intensity light in the chamber. At the same nucleotide flow order, the TF12 DNA underwent no incorporation of DNA and no high intensity light was produced.

Curve 1 shows a profile of six pixels (Nos. 1-6) which cross the center points of the two adjacent $SiO_2$ coated chambers. For example, Pixel No 1 is the first pixel which is offset one pixel from the center of the TF12 chamber in an upstream direction, Pixel No. 2 is one pixel to the right after Pixel No. 1 in the downstream direction. From Pixel No. 1 to Pixel No. 6, a scanning path can be drawn which passes the center points of the two chambers (TF10 and TF2) in a downstream direction. Pixel No. 3 is located inside the TF12 chamber and in theory the TF12 chamber in theory should not give any signal because there is no DNA incorporation in that chamber. However, an increased intensity of light was observed at pixel No. 3 in the TF12 chamber due to light from the adjacent TF10 chamber which bled photons over into the TF12 chamber.

For comparison, on the metal-coated first half of the array, sequencing reactions were conducted in two adjacent metal-coated chambers which contained the same TF10 and TF12 DNA fragments, one in each chamber, and the sequencing process was conducted at the same nucleotide flow order of 43. The signal observed at pixel No. 3 in the metal coated chambers as shown by curve 3 is non-linearly smaller than the signal measured in the $SiO_2$ coated chambers on the first half of the array, thus indicating that the metal coated, opaque sidewalls reduce optical bleeding of photons between two adjacent metal coated chambers.

FIG. 24b shows the results of the same experiment, but the sequencing reactions were conducted at a nucleotide flow order of 35. At this nucleotide flow order, TF10 underwent 4 DNA incorporations and again at pixel No. 3, there is less signal due to reduced optical bleeding on the metal coated first half of the array compared to the second half of the array.

Example 7

$SiO_2$ Thin Film Coated Microwell Array

In one embodiment, the array is formed from a commercial FOF (Incom, Charlton, Mass.) which has been chemically etched on a single side with acid to yield individual reaction chambers. Each reaction chamber formed by etching has a volume of about 75 pL. The FOF is cleaned prior to coating with a thin film. The preferred thin film coating is the non-metal oxide $SiO_2$ with a thickness measuring 0.1-5.0 microns thick. The $SiO_2$ coating is optically transparent and impermeable to water. The thin film coating is applied using an ion-plating vapor deposition method. The use of thin film coated reaction chambers on a FOF surface serves several purposes; i) delayed diffusion of the luminescence from emitting light in a different region of the array, ii) isolation of reaction chambers that contain components of the assay solution or reaction mixture protected from any deleterious effects of the array substrate material, and iii) prevention of any leaching of substrate materials into the chamber solution, and iv) very efficient, high numerical aperture optical coupling to the CCD. Finally, the larger the amount of reactant (e.g. immobilized sequencing template) or analyte within a reaction mixture or assay solution, the more optical signal one is able to achieve.

Example 8

Metal Thin Film Coated Microwell Array

The array is formed from a commercial FOF (Incom, Charlton, Mass.) which has been chemically etched on a single side with acid to yield individual reaction chambers. Substantially all of the reaction chambers formed by the etch process have a volume of about 75 pL and a depth of between 50-55 µm. The FOF is cleaned prior to coating with a non-transparent thin film coating. The non-transparent thin film coating is chromium with a thickness measuring about 200-300 nm on the top surface of the array and 60-120 nm on the sidewall and no less than 50 nm on the corner area of substantially all of the reaction chambers. The coating is opaque. The thin film coating is applied using a ion-deposition method. The use of an opaque thin film coated reaction chambers on a FOF surface provides an array with several advantages. Optical problems such as optical bleeding, light scattering, and interference between neighboring reaction chambers are eliminated and light is concentrated. Bead loading efficiency is maximized to close to 100%.

Example 9

Metal and $SiO_2$ Thin Film Coated Microwell Array

The array apparatus for nucleic acid sequencing is formed from a commercial FOF (Incom, Charlton, Mass.) which has been chemically etched on a single side with acid to yield individual reaction chambers. The apparatus used to etch an FOF includes two PEEK clamps and a silicone etch gasket. Substantially all of the reaction chambers formed by the etch process have a volume of about 75 pL and a depth of between 50-55 µm. The FOF is cleaned prior to coating with a non-transparent thin film coating. The non-transparent thin film coating is chromium with a thickness measuring about 200-300 nm on the top surface of the array, 60-120 nm on the sidewall and no less than 50 nm on the corner area of substantially all of the reaction chambers of the array. The coating is opaque. The thin film coating is applied using an ion-deposition method. After the non-transparent thin film coating is applied, a transparent thin film coating is applied. The transparent thin film coating is $SiO_2$ with a thickness measuring about 200-400 nm on the top surface of the array, 50-100 nm on the sidewall and no less than 50 nm on the corner area of substantially all of the reaction chambers. An array with reaction chambers coated with first, a non-transparent film coating and second, a transparent thin film coating provides an array with several advantages. Optical problems such as optical bleeding, light scattering, and interference between neighboring reaction chambers are eliminated, and the transparent SiO$_2$ coating applied on top of the non-transparent coating also protects the chromium coating from erosion.

What is claimed:

1. An array comprising: a fiber optic faceplate substrate that comprises a planar top surface comprising a plurality of etched reaction chambers and a polished optically conductive planar bottom surface; wherein, each reaction chamber comprises an interior bottom surface and an interior sidewall surface; further wherein the top surface of the array and the interior sidewall surface of substantially all of the reaction chambers is coated with a non-transparent thin film coating and the interior bottom surface of substantially all of the reaction chambers does not have a non-transparent coating, wherein the non-transparent coating is opaque; and at least one of the interior bottom surface or interior sidewall surface of substantially all of the reaction chambers or top surface is coated with a transparent thin film coating, which differs from the non-transparent coating and wherein the non-transparent coating is positioned underneath the transparent coating, and wherein the transparent coating is optically transparent, 0.1-5.0 microns thick, and is impermeable to water.

2. The array of claim 1, wherein the transparent coating is silicon dioxide.

3. The array of claim 1, wherein, the thickness of the transparent coating is about 200-400 nm on the top surface, 50-100 nm on the sidewall, and 100-300 nm on the bottom.

4. The array of claim 1, wherein, the thickness of the non-transparent coating is about 200-300 nm on the top surface, 60-120 nm on the sidewall, and no less than 50 nm on the corner area.

5. The array of claim 1, wherein the non-transparent coating is selected from an organic compound, an inorganic compound, and a non-metal oxide.

6. The array of claim 5, wherein the inorganic compound is a metal.

7. The array of claim 6, wherein the metal is selected from chromium, gold, silver, titanium, platinum and aluminum.

8. The array of claim 1, wherein the interior sidewall surface of substantially all of the reaction chambers is coated with the transparent coating.

9. The array of claim 1, wherein the top surface is coated with the transparent coating.

10. The array of claim 1, wherein the interior bottom surface of substantially all of the reaction chambers is coated with the transparent coating.

11. The array of claim 1, wherein each one of the interior sidewall surface and the interior bottom surface of substantially all of the reaction chambers and top surface is coated with the transparent coating.

12. The array of claim 1, wherein the interior bottom surface of substantially all of the reaction chambers are partially coated with the non-transparent coating, such that the non-transparent coating covers a corner area formed at the junction between the interior bottom surface and the interior sidewall surface of the reaction chamber and is absent from the center of the interior bottom surface of the reaction chamber which forms an aperture near the center of the interior bottom surface.

13. The array of claim 12, wherein the diameter of the aperture is 28 microns and a ring formed around the aperture by the non-transparent coating has a width of 8.5 microns.

14. The array of claim 1, wherein the top surface and the interior bottom surface of substantially all of the reaction chambers are coated with the transparent coating.

15. The array of claim 1, wherein the interior bottom surface of substantially all of the reaction chambers is coated with the transparent coating, and the top surface is not coated.

16. The array of claim 1, wherein the transparent coating comprises at least a first and second transparent coating.

17. The array of claim 1, wherein the non-transparent coating comprises at least a first and second non-transparent coating.

18. The array of claim 1, wherein an enzyme is immobilized on the transparent coating.

19. The array of claim 1, wherein the number of reaction chambers is greater than 10,000.

20. The array of claim 11, wherein the metal is titanium.

* * * * *

UNITED STATES PATENT AND TRADEMARK OFFICE
CERTIFICATE OF CORRECTION

| | | |
|---|---|---|
| PATENT NO. | : 7,682,816 B2 | Page 1 of 1 |
| APPLICATION NO. | : 11/215458 | |
| DATED | : March 23, 2010 | |
| INVENTOR(S) | : Jong-Bum Kim et al. | |

It is certified that error appears in the above-identified patent and that said Letters Patent is hereby corrected as shown below:

At Column 52, Line 40, Claim 20

"20. The array of claim 11, wherein the metal is titanium."

should read

--20. The array of claim 7, wherein the metal is titanium.--

Signed and Sealed this

Fifteenth Day of June, 2010

David J. Kappos
*Director of the United States Patent and Trademark Office*